US009039639B2

(12) United States Patent
George et al.

(10) Patent No.: US 9,039,639 B2
(45) Date of Patent: *May 26, 2015

(54) EXTERNAL EAR CANAL PRESSURE REGULATION SYSTEM

(71) Applicant: GBS Ventures LLC, Phoenix, AZ (US)

(72) Inventors: David George, Scottsdale, AZ (US); George Buckler, Phoenix, AZ (US); David Brice Sullivan, Mechanicsburg, PA (US)

(73) Assignee: GBS Ventures LLC, Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/316,668

(22) Filed: Jun. 26, 2014

(65) Prior Publication Data

US 2015/0003644 A1 Jan. 1, 2015

Related U.S. Application Data

(63) Continuation-in-part of application No. 14/292,469, filed on May 30, 2014.

(60) Provisional application No. 61/983,865, filed on Apr. 24, 2014, provisional application No. 61/863,317, filed on Aug. 7, 2013, provisional application No. 61/841,111, filed on Jun. 28, 2013.

(51) Int. Cl.
*A61F 11/00* (2006.01)
*H04R 1/42* (2006.01)

(52) U.S. Cl.
CPC ........................................ *H04R 1/42* (2013.01)

(58) Field of Classification Search
CPC ........ H04R 1/42; A61F 11/00; A61H 9/0071; A61H 21/00; A61H 2205/0257; A61H 2201/5005
USPC ........... 601/46, 48, 55, 76, 77, 79, 84, 88, 89, 601/96, 148; 604/21, 26, 275; 381/165, 329
See application file for complete search history.

(56) References Cited

U.S. PATENT DOCUMENTS 2,437,490 A 3/1948 Watson et al.
3,757,769 A 9/1973 Arguimbau et al.
(Continued)

FOREIGN PATENT DOCUMENTS

AU 2004/238090 11/2004
CA 1136751 11/1982
(Continued)

OTHER PUBLICATIONS

Cadwell. Sierra Wave. Website, http://www.cadwell.com, originally downloaded Feb. 27, 2014, 1page.
(Continued)

*Primary Examiner* — Quang D Thanh
(74) *Attorney, Agent, or Firm* — Craig R. Miles; CR Miles P.C.

(57) ABSTRACT

An external ear canal pressure regulation device including a fluid flow generator and an earpiece having a first axial earpiece conduit fluidicly coupled to the fluid flow generator, whereby the earpiece has a compliant earpiece external surface configured to sealably engage an external ear canal as a barrier between an external ear canal pressure and an ambient pressure.

22 Claims, 27 Drawing Sheets

(56) References Cited

U.S. PATENT DOCUMENTS

| | | | |
|---|---|---|---|
| 3,872,559 A | 3/1975 | Leight | |
| 4,002,161 A | 1/1977 | Klar et al. | |
| 4,133,984 A | 1/1979 | Akijama | |
| 4,160,449 A | 7/1979 | Wade | |
| 4,206,756 A | 6/1980 | Grossan | |
| 4,289,143 A | 9/1981 | Canavesio et al. | |
| 4,349,083 A | 9/1982 | Bennett | |
| 4,472,342 A | 9/1984 | Carr | |
| 4,552,137 A | 11/1985 | Strauss | |
| 4,632,104 A | 12/1986 | Conrow | |
| 4,688,582 A | 8/1987 | Heller et al. | |
| 4,775,370 A | 10/1988 | Berry | |
| 4,809,708 A | 3/1989 | Geisler et al. | |
| 4,896,380 A | 1/1990 | Kamitani | |
| 4,896,679 A | 1/1990 | St. Pierre | |
| 4,964,769 A | 10/1990 | Hass | |
| 4,984,579 A | 1/1991 | Burgert et al. | |
| 5,024,612 A * | 6/1991 | van den Honert et al. | 604/36 |
| 5,105,822 A | 4/1992 | Stevens et al. | |
| 5,131,411 A | 7/1992 | Casali et al. | |
| 5,476,446 A | 12/1995 | Arenburg | |
| 5,483,027 A | 1/1996 | Krause | |
| 5,483,975 A | 1/1996 | Hirschenbain | |
| 5,488,961 A | 2/1996 | Adams | |
| 5,631,965 A | 5/1997 | Chang et al. | |
| 5,699,809 A | 12/1997 | Combs et al. | |
| 5,740,258 A | 4/1998 | Goodwin-Johansson | |
| 5,755,234 A | 5/1998 | Mobley et al. | |
| 5,769,891 A | 6/1998 | Clayton | |
| 5,776,179 A | 7/1998 | Ren et al. | |
| 5,819,745 A | 10/1998 | Mobley et al. | |
| 5,865,183 A | 2/1999 | Hirschebain | |
| 5,868,682 A | 2/1999 | Combe et al. | |
| 5,944,711 A | 8/1999 | Pender | |
| 6,004,274 A | 12/1999 | Nolan et al. | |
| 6,024,726 A | 2/2000 | Hill | |
| 6,129,174 A | 10/2000 | Brown et al. | |
| 6,139,507 A | 10/2000 | Jeng | |
| 6,159,171 A | 12/2000 | Densert et al. | |
| 6,186,959 B1 | 2/2001 | Canfield et al. | |
| 6,258,067 B1 | 7/2001 | Hill | |
| 6,359,993 B2 | 3/2002 | Brimhall | |
| 6,629,938 B1 | 10/2003 | Engvall et al. | |
| 6,725,568 B2 | 4/2004 | Gronka | |
| 6,800,062 B2 | 10/2004 | Epley | |
| 6,820,717 B2 | 11/2004 | Fleming et al. | |
| 6,878,128 B2 | 4/2005 | MacMahon et al. | |
| 6,958,043 B2 | 10/2005 | Hissong | |
| 6,981,569 B2 | 1/2006 | Stilp | |
| 7,022,090 B1 | 4/2006 | Engvall et al. | |
| 7,162,039 B1 | 1/2007 | Callahan | |
| 7,179,238 B2 | 2/2007 | Hissong | |
| 7,268,466 B2 | 9/2007 | Rasmussen | |
| 7,352,871 B1 | 4/2008 | Mozo | |
| 7,766,858 B2 | 8/2010 | Franz et al. | |
| 7,779,844 B2 | 8/2010 | Purcell et al. | |
| 7,785,346 B2 | 8/2010 | Blumberg | |
| 7,797,042 B2 | 9/2010 | Dietrich et al. | |
| 7,833,282 B2 | 11/2010 | Mandpe | |
| 7,892,180 B2 | 2/2011 | Epley | |
| 7,959,597 B2 | 6/2011 | Baker et al. | |
| 7,988,657 B2 | 8/2011 | Shapiro et al. | |
| 8,020,563 B2 | 9/2011 | Pfanstiehl | |
| 8,047,207 B2 | 11/2011 | Perez et al. | |
| 8,052,693 B2 | 11/2011 | Shahoian | |
| 8,199,919 B2 | 6/2012 | Goldstein et al. | |
| 8,241,224 B2 | 8/2012 | Keefe | |
| 8,249,285 B2 | 8/2012 | Killion et al. | |
| 8,251,925 B2 | 8/2012 | Keady et al. | |
| 8,262,717 B2 | 9/2012 | Rogers et al. | |
| 8,328,830 B1 | 12/2012 | Pandit | |
| 8,398,562 B2 | 3/2013 | Keller | |
| 8,414,521 B2 | 4/2013 | Baker et al. | |
| 8,506,469 B2 | 8/2013 | Dietrich et al. | |
| 8,515,552 B2 | 8/2013 | Englehart | |
| 8,550,206 B2 | 10/2013 | Keady et al. | |
| 8,625,833 B1 | 1/2014 | Armwood | |
| 8,666,502 B2 | 3/2014 | Hartlep et al. | |
| 8,688,239 B2 | 4/2014 | Hartlep et al. | |
| 2002/0069883 A1 | 6/2002 | Hirchenbain | |
| 2003/0195588 A1 | 10/2003 | Fischell et al. | |
| 2003/0220536 A1 | 11/2003 | Hissong | |
| 2004/0097839 A1 | 5/2004 | Epley | |
| 2004/0163882 A1 | 8/2004 | Fleming et al. | |
| 2005/0065585 A1 | 3/2005 | Salas | |
| 2005/0209516 A1 | 9/2005 | Fraden | |
| 2006/0100681 A1 | 5/2006 | Salas Carpizo | |
| 2006/0197412 A1 | 9/2006 | Rasmussen | |
| 2006/0253087 A1 | 11/2006 | Vlodaver et al. | |
| 2006/0272650 A1 | 12/2006 | Hoogenakker et al. | |
| 2007/0299362 A1 | 12/2007 | Epley et al. | |
| 2008/0011308 A1 | 1/2008 | Fleming | |
| 2008/0154183 A1 | 6/2008 | Baker et al. | |
| 2008/0208100 A1 | 8/2008 | Wolff | |
| 2008/0212787 A1 | 9/2008 | Goldstein et al. | |
| 2009/0173353 A1 | 7/2009 | Pursell et al. | |
| 2009/0228103 A1 | 9/2009 | Clayton | |
| 2010/0002897 A1 | 1/2010 | Keady | |
| 2010/0030131 A1 | 2/2010 | Morriss et al. | |
| 2010/0071707 A1 | 3/2010 | Wohl | |
| 2010/0071708 A1 | 3/2010 | Lenhardt | |
| 2010/0179490 A1 | 7/2010 | Connelly et al. | |
| 2011/0079227 A1 | 4/2011 | Turcot et al. | |
| 2011/0098551 A1 | 4/2011 | Zhang | |
| 2011/0130786 A1 | 6/2011 | Clayton et al. | |
| 2011/0184341 A1 | 7/2011 | Baker et al. | |
| 2011/0224493 A1 | 9/2011 | Oyadiran et al. | |
| 2011/0245902 A1 | 10/2011 | Katz | |
| 2012/0046607 A1 | 2/2012 | Syk | |
| 2012/0265093 A1 | 10/2012 | Allen et al. | |
| 2012/0296268 A1 | 11/2012 | Vlodavaer et al. | |
| 2012/0302859 A1 | 11/2012 | Keefe | |
| 2013/0123889 A1 | 5/2013 | Katz et al. | |
| 2013/0136285 A1 | 5/2013 | Naumann | |
| 2013/0152949 A1 | 6/2013 | Simon | |
| 2013/0177179 A1 | 7/2013 | Ambrose et al. | |
| 2013/0304103 A1 | 11/2013 | Burres | |
| 2013/0324932 A1 | 12/2013 | Cogley | |

FOREIGN PATENT DOCUMENTS

| | | |
|---|---|---|
| CA | 1222464 | 6/1987 |
| CA | 1241152 | 8/1988 |
| CA | 2003452 | 6/1990 |
| CA | 2275057 | 10/1999 |
| CA | 2429560 | 1/2004 |
| CN | 2418864 | 2/2001 |
| CN | 2530645 | 1/2003 |
| CN | 2912525 | 6/2007 |
| CN | 201143258 | 11/2008 |
| CN | 201164541 | 12/2008 |
| CN | 101668497 | 3/2010 |
| CN | 201524178 | 7/2010 |
| CN | 201558360 | 8/2010 |
| CN | 201870809 | 6/2011 |
| CN | 202036187 | 11/2011 |
| CN | 202185057 | 4/2012 |
| CN | 102551957 | 7/2012 |
| CN | 202313927 | 7/2012 |
| CN | 202477966 | 10/2012 |
| CN | 202505833 | 10/2012 |
| CN | 102986250 | 3/2013 |
| DE | 102011008802 | 7/2012 |
| EP | 0026247 | 4/1981 |
| EP | 0400900 | 12/1990 |
| EP | 1027863 | 8/2000 |
| EP | 2207366 | 7/2010 |
| GB | 1522031 | 8/1978 |
| GB | 2185688 | 7/1987 |
| GB | 2343263 | 5/2000 |
| GB | 2479891 | 11/2011 |
| IT | 1214840 | 1/1990 |
| JP | 2006345903 | 12/2006 |
| JP | 2009022699 | 2/2009 |

(56) References Cited

FOREIGN PATENT DOCUMENTS

| | | |
|---|---|---|
| JP | 2010233643 | 10/2010 |
| JP | 2010233643 | 12/2010 |
| JP | 2011217986 | 11/2011 |
| JP | 2013068448 | 4/2013 |
| JP | 2013102784 | 5/2013 |
| MX | 9705652 | 7/1998 |
| MX | PA03005598 | 10/2004 |
| MX | 2010014470 | 2/2011 |
| MX | 2011006854 | 8/2011 |
| MX | 2012007726 | 8/2012 |
| WO | WO 94/22372 | 10/1994 |
| WO | WO 00/10627 | 3/2000 |
| WO | WO 03/075761 | 9/2003 |
| WO | WO 2004/064672 | 8/2004 |
| WO | WO 2004/100844 | 11/2004 |
| WO | WO 2006/009545 | 1/2006 |
| WO | WO 2007/084674 | 7/2007 |
| WO | WO 2007/118092 | 10/2007 |
| WO | WO 2007/145853 | 12/2007 |
| WO | WO 2008/036368 | 3/2008 |
| WO | WO 2008/064230 | 5/2008 |
| WO | WO 2008/086187 | 7/2008 |
| WO | WO 2008/128173 | 10/2008 |
| WO | WO 2008/153588 | 12/2008 |
| WO | WO 2009/050306 | 4/2009 |
| WO | WO 2009/077902 | 6/2009 |
| WO | WO 2009/077902 | 10/2009 |
| WO | WO 2010/005899 | 1/2010 |
| WO | WO 2010/016925 | 2/2010 |
| WO | WO 2010/085196 | 7/2010 |
| WO | 2012/007193 | 1/2012 |
| WO | WO 2013/075255 | 5/2013 |
| ZA | 200509787 | 1/2009 |

OTHER PUBLICATIONS

Ferrotec. Thermal Solutions. Website, https://thermal.ferrotec.com, originally downloaded Feb. 27, 2014, 1page.
Ferrotec. Thermoelectric Technical Reference—Installation of Thermoelectric Modules. Website, https://thermal.ferrotec.com, originally downloaded May 21, 2014, 4 total pages.
Ferrotec. Thermoelectric Technical Reference—Introduction to Thermoelectric Cooling. Website, https://www.ferrotec.com, originally downloaded Feb. 27, 2014, 2total pages.
Kolev. How caloric vestibular irrigation influences migraine attacks. Cephalalgia. Aug. 1990, vol. 10, Issue 4, pp. 167-169 (abstract only).
Lifting the Burden. The Global Campaign Against Headache. Website, http://www.l-t-b.org, originally downloaded Feb. 27, 2014, 1 page.
Liszewski. Ear Pressure Equalizer. Website, http://www.ohgizmo.com, originally downloaded Dec. 18, 2013, 1 page.
Long Island News12.Com. Long Island Naturally: Migraines. Website video, http://longisland.news12.com/multimedia/long-island-naturally-migraines-1.6501113, Nov. 26, 2013, 3 total.
Medscape. Peripheral Nerve Stimulator—Train of Four Monitoring. Website, http://emedicine.medscape.com, originally downloaded Feb. 27, 2014, 2 total pages.
Medtronic. Meniett Device for Meniere's Disease. Meniett Low-Pressure Pulse Generator device. Website, http://www.medtronic.com, originally downloaded Feb. 27, 2014, 2 total page.
New York Health Solutions. Migraine Headaches. Website, http://www.nyhealthsolutions.com, originally downloaded May 23, 2014, 2 total pages.
Pietrobon. Migraine: new molecular mechanisms. Neuroscientist. Aug. 2005, vol. 11, Issue 4, pp. 373-386 (abstract only).
Saunders. Tympanic membrane sensation. Brain. Jun. 1985, vol. 108, Issue 6, pp. 387-404 (abstract only).
Sheftell, F, Steiner, TJ, Thomas, H. Harry Potter and the Curse of Headache. Headache: The Journal of Head and Face Pain. Jun. 2007, vol. 47, Issue 6, pp. 911-916 (abstract on.
Smartproducts. Series 100—Cartridge Specialty Check Valves and Pressure Relief Valves. Online catalog, www.smartproducts.coom, originally downloaded Mar. 28, 2014, 2 tota.
Stovner, LJ, et al. The global burden of headache: a documentation of headache prevalence and disability worldwide. Cephalalgia, 2007. vol. 27, pp. 193-210.
Sullivan. Ear Insufflation as a Novel Therapy Which Produces Rapid Relief of Migraine Headache. Funct Neurol Rehabil Egon 2013; vol. 3, Issue 1, pp. 93-107.
Sullivan. Ear Insufflation Produces Rapid and Significant Relief of Trigeminal Neuraliga. Funct Neurol Rehabil Egon 2013; vol. 3, Issue 4, pp. 1-6.
Ultimate Ears. Ultimate Ears Custom In-Ear Monitors. Website, http://pro.ultimateears.com, originally downloaded Feb. 27, 2014, 3 total pages.
Westone. Occupational Earpieces. Website, http://www.westone.com, originally downloaded Feb. 27, 2014, 2 total pages.
Wikipedia. Microcurrent electrical neuromuscular stimulator. Website, http://en.wikipedia.org, originally downloaded Feb. 27, 2014, 3 total pages.
Wikipedia. Somatosensory evoked potential. Website, http://en.wikipedia.org, originally downloaded Feb. 27, 2014, 5 total pages.
Wikipedia. Transcutaneous electrical nerve stimulation. Website, http://en.wikipedia.org, originally downloaded Feb. 27, 2014, 5 total pages.
World Health Organization. Headache disorders. Website, http://www.who.int, originally downloaded Feb. 27, 2014, 4 total pages.
U.S. Appl. No. 61/983,865, filed Apr. 24, 2014.
U.S. Appl. No. 61/863,317, filed Aug. 7, 2013.
U.S. Appl. No. 61/841,111, filed Jun. 28, 2013.
Patent Cooperation Treaty Patent Application No. PCT/US14/44159, filed Jun. 25, 2014.
U.S. Appl. No. 14/292,469, filed May 30, 2014.
Breathometer. Breathometer—The World's First Smartphone Breathalyzer. Website, http://www.breathometer.com, originally downloaded Jun. 19, 2014, 8 total pages.
Medtronic. The Meniett Device for Meniere's Disease. On-line article, http://www.medtronic.com, originally downloaded Mar. 13, 2015, 2 total pages.
Baguley et al. Does caloric vestibular stimulation modulate tinnitus? Neuroscience Letters, Mar. 2011, 492(1), pp. 52-54.
Baier et al. Vestibular-Evoked Myogenic Potentials in "Vestibular Migraine" and Meniere's Disease. Ann. N.Y. Acad. Sci., May 2009, 1164, pp. 324-327.
Becker. Weather and migraine: Can so many patients be wrong? Cephalalgia, Mar. 2011, 31(4), pp. 387-390.
Bolay et al. Does Low Atmospheric Pressure Independently Trigger Migraine? Headache, Oct. 2011, 51(9), pp. 1426-1430.
Dirckx et al. Human tympanic membrane deformation under static pressure. Hearing Research, Jan. 1991, 51(1), pp. 93-105.
Fasold et al. Human Vestibular Cortex as Identified with Caloric Stimulation in Functional Magnetic Resonance Imaging. NeuroImage, Nov. 2002, 17(3), pp. 1384-1393.
Job et al. Cortical Representation of Tympanic Membrane Movements due to Pressure Variation: An fMRI Study. Human Brain Mapping, May 2011, 32(5), pp. 744-749.
Klingner et al. Components of vestibular cortical function. Behavioral Brain Research, Jan. 2013, 236(1), pp. 194-199.
McGeoch et al. Vestibular stimulation can relieve central pain of spinal origin. Spinal Cord, Nov. 2008, 46(11), pp. 756-757.
Nagai et al. Encapsulated nerve corpuscles in the human tympanic membrane. Archives of Otorhinolaryngology, 1989, 246(3), pp. 169-172.
Nihashi et al. Representation of the ear in human primary somatosensory cortex. NeuroImage, Feb. 2001, 13(2), pp. 295-304 (abstract only).
Porta-Etessam et al. Neuro-otological symptoms in patients with migraine. Neurologia, Mar. 2011, 26(2), pp. 100-104.
Ramachandran et al. Rapid Relief of Thalamic Pain Syndrome Induced by Vestibular Caloric Stimulation. Neurocase, Jun. 2007, 13(3), pp. 185-188.
Sakata et al. Air pressure-sensing ability of the middle ear—Investigation of sensing regions and appropriate measurement conditions. Auris Nasus Larynx, Aug. 2009, 36(4), pp. 393-399.
Schulman. Breath-Holding, Head Pressure, and Hot Water: An Effective Treatment for Migraine Headache. Headache, Nov.-Dec. 2002, 42(10), pp. 1048-1050.

* cited by examiner

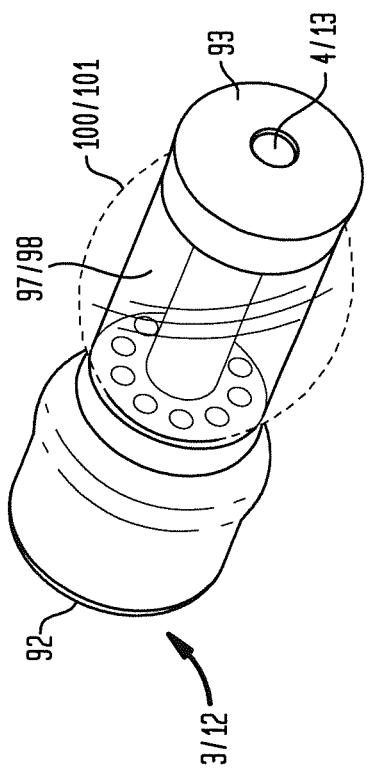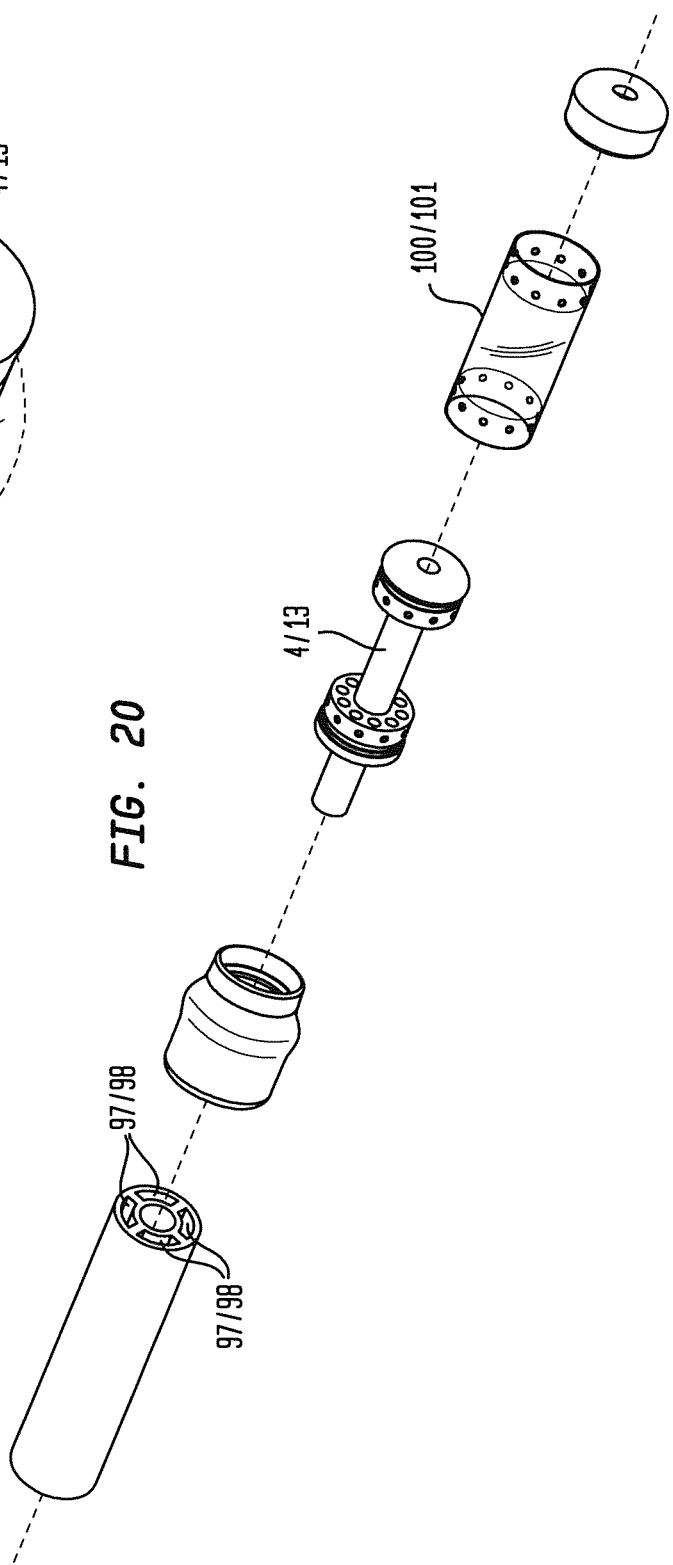

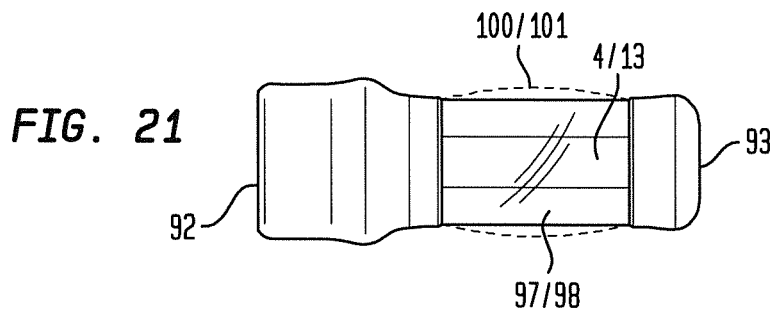
FIG. 21
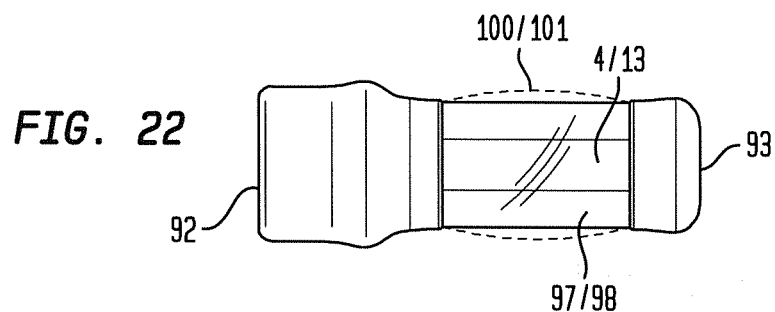
FIG. 22
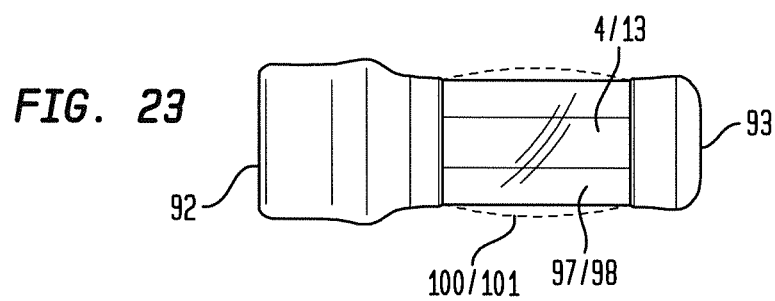
FIG. 23
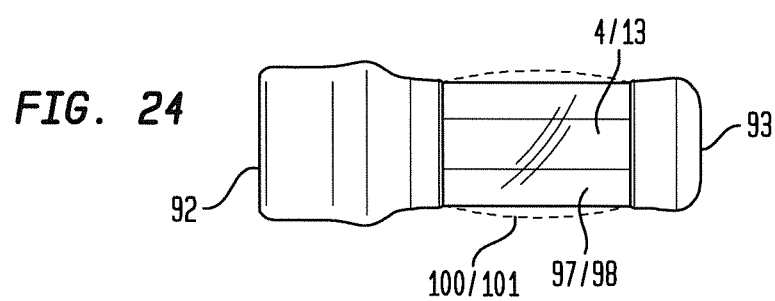
FIG. 24
FIG. 25
FIG. 26
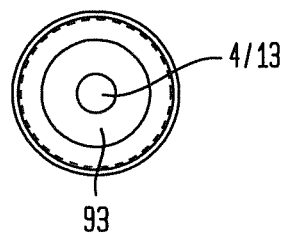
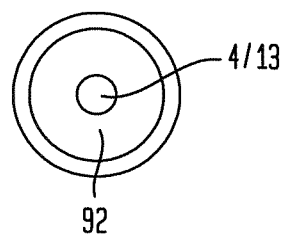

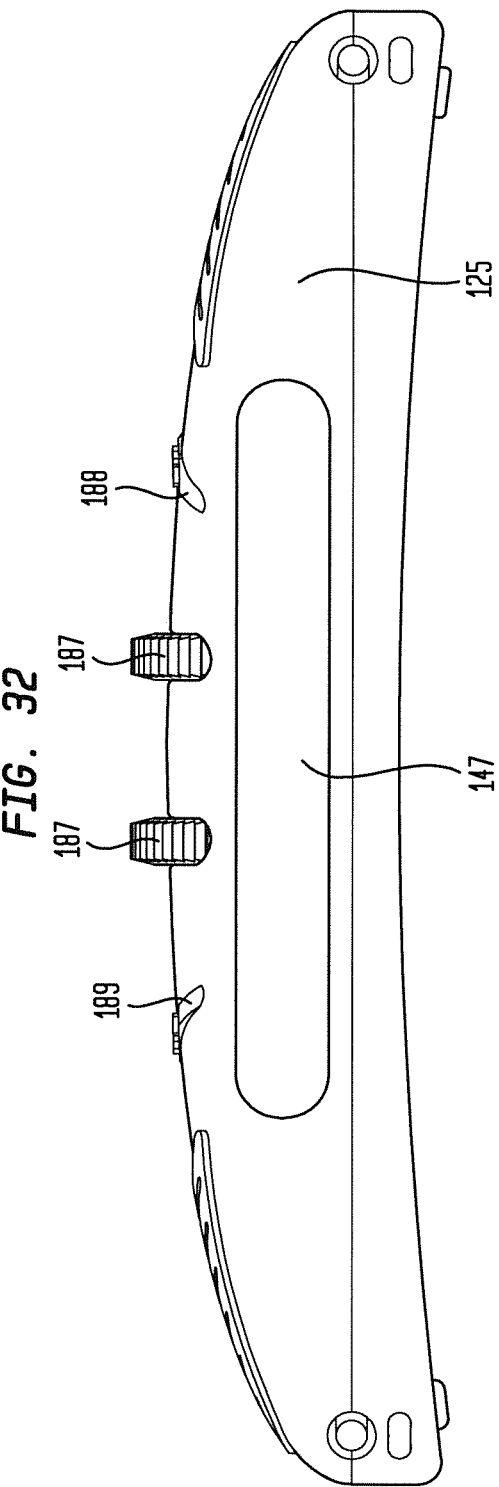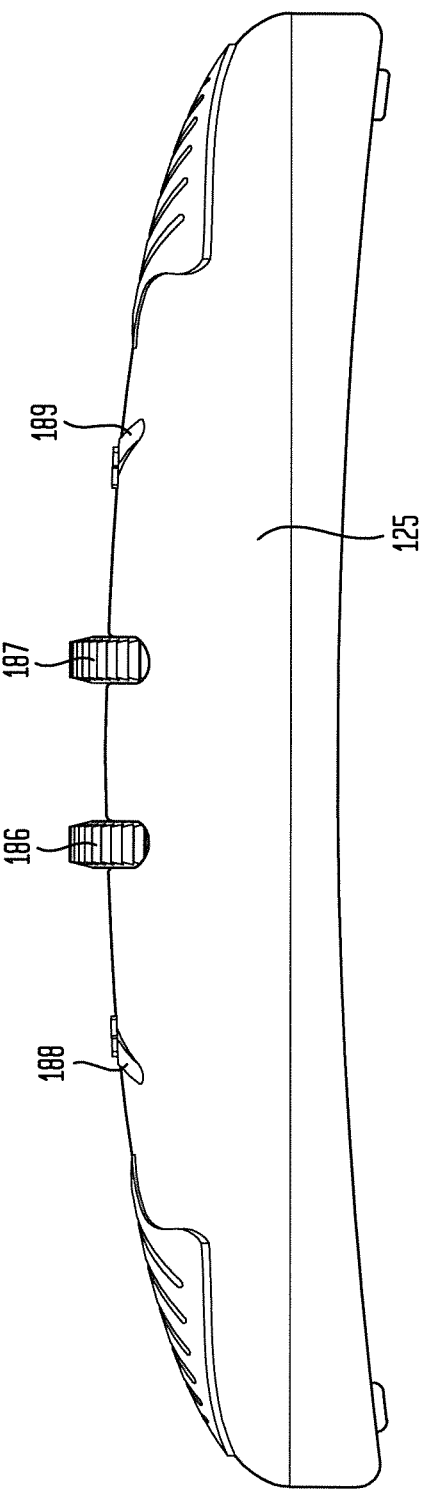

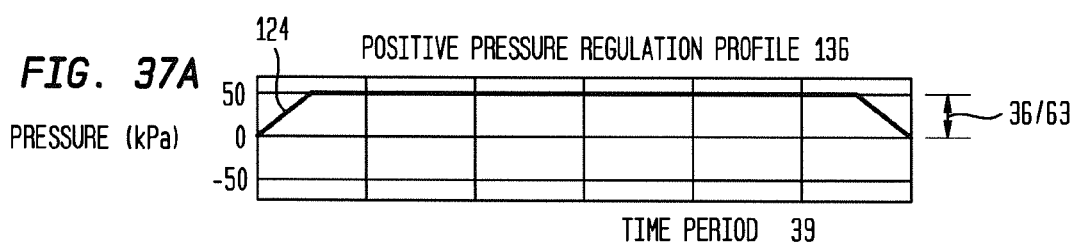
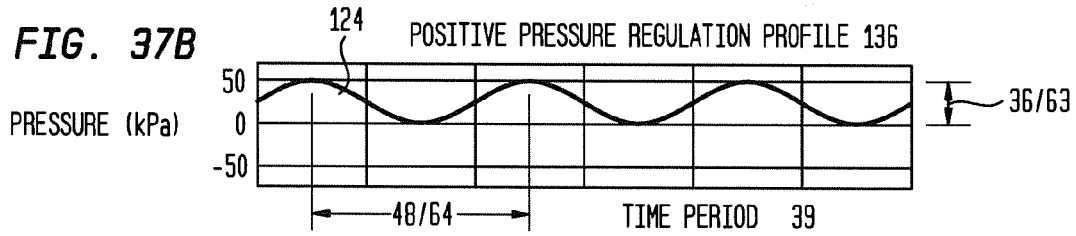
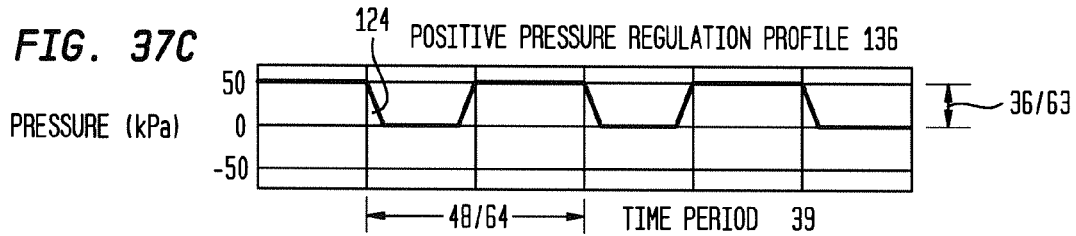
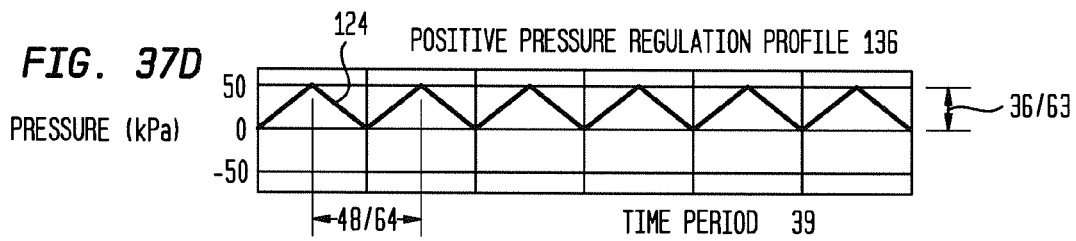
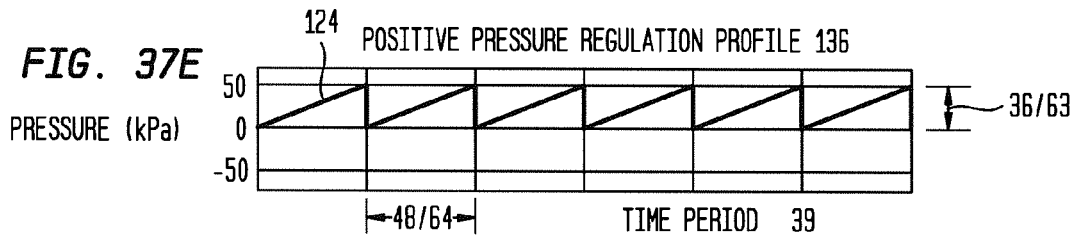
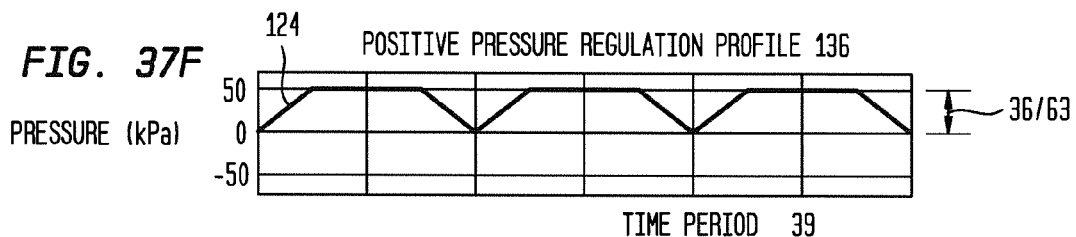
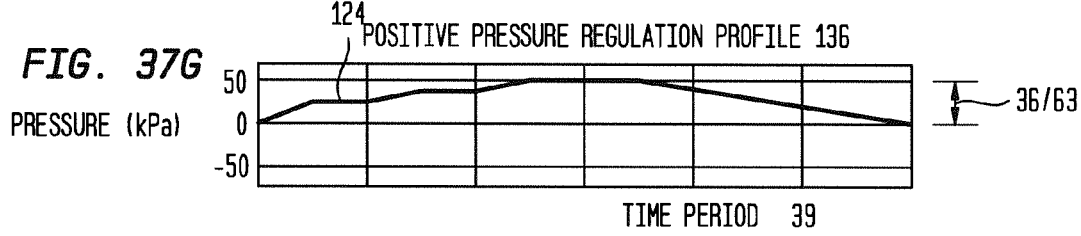

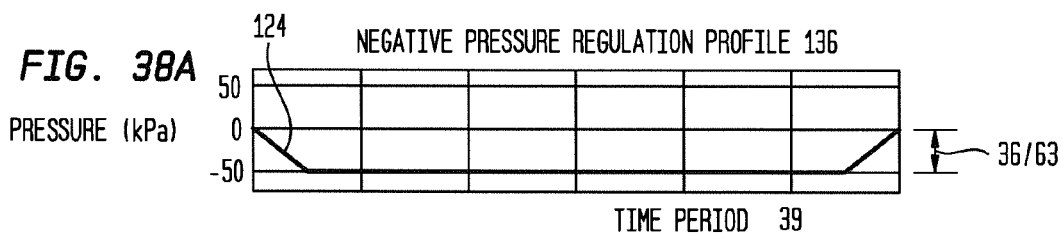
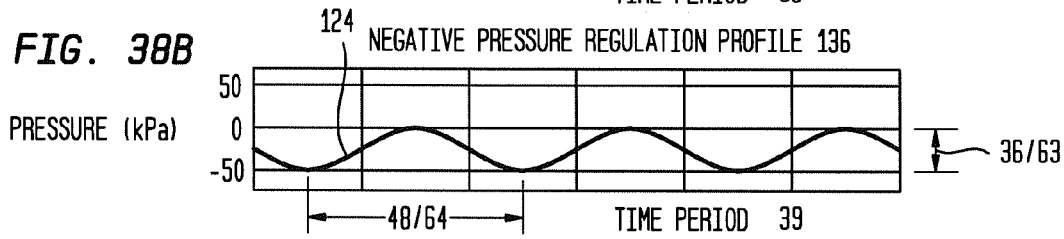
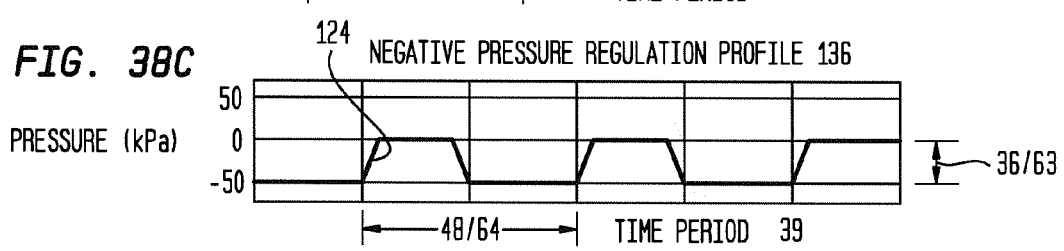
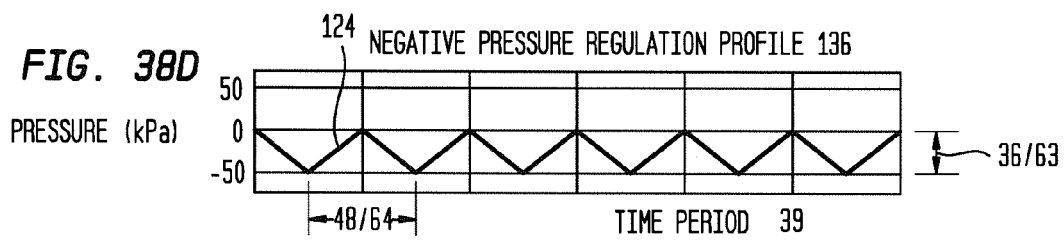
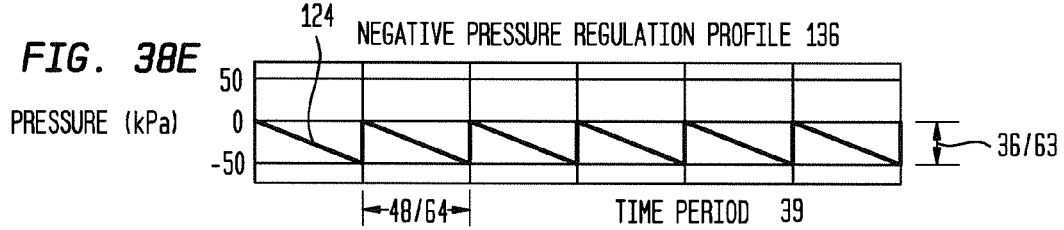
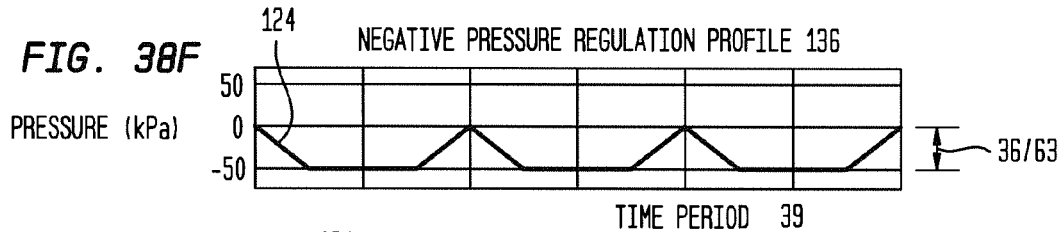
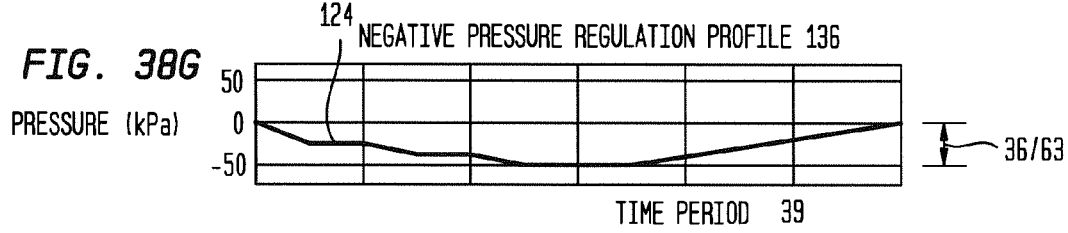

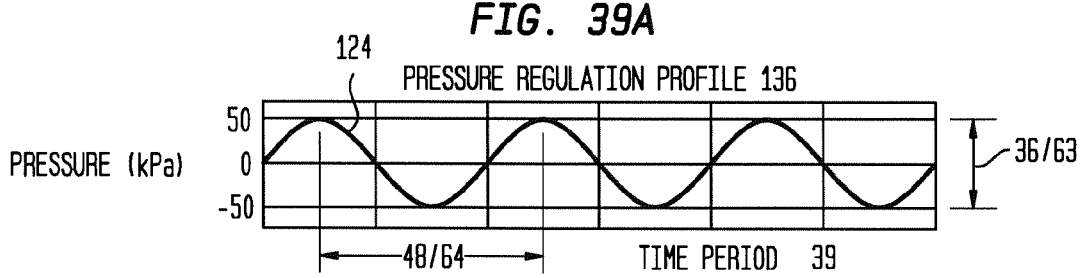
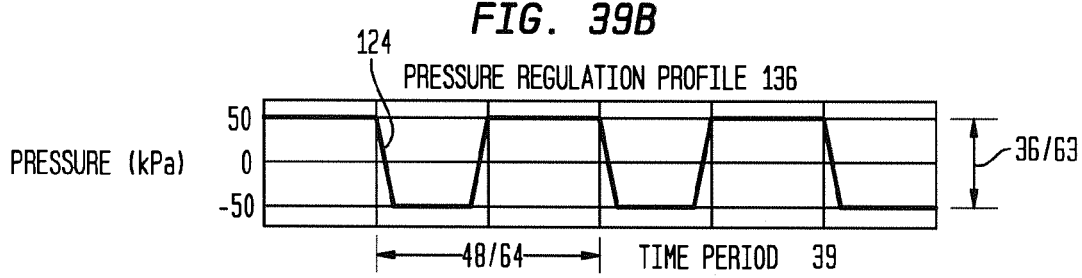
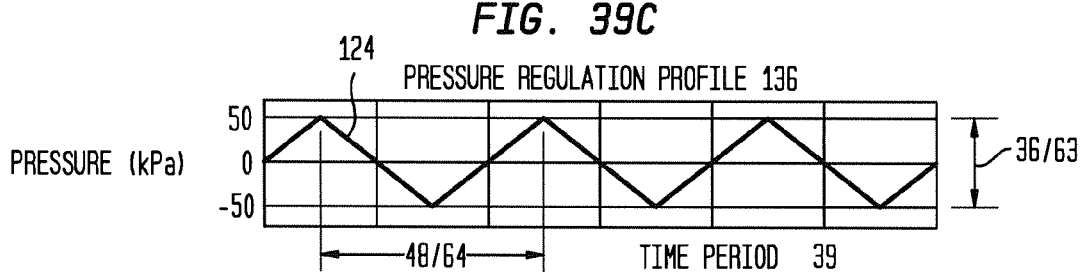
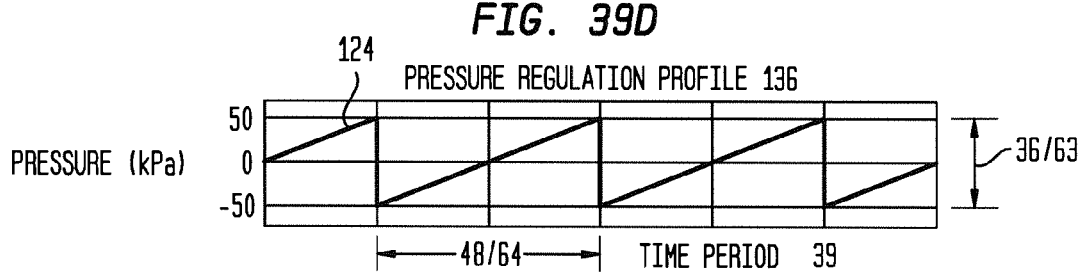
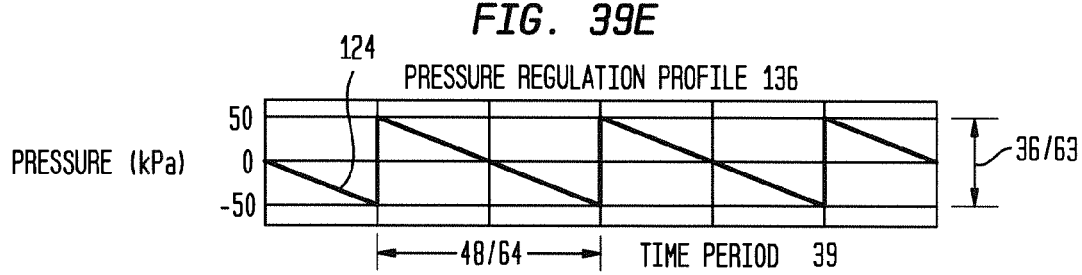

FIG. 40

| MODE | OPEN | CLOSED |
|---|---|---|
| INSUFFLATE L & R | V1-V2-V3L-V3R-V4-V5 | V6-IL-IR |
| INSUFFLATE L ONLY | V1-V3L-V4 | V2-V3R-V5-V6-IL-IR |
| INSUFFLATE R ONLY | V2-V3R-V5 | V1-V3L-V4-V6-IL-IR |
| INSUFFLATE L & IRRIGATE R | V1-V3L-V3R-V4-IR | V2-V5-V6-IL |
| INSUFFLATE R & IRRIGATE L | V2-V3R-V3L-V5-IL | V1-V4-V6-IR |
| IRRIGATE L & R | V3L-V3R-IL-IR-V6 | V1-V2-V4-V5 |
| IRRIGATE L ONLY | V3L-IL-V6 | V1-V2-V3R-V4-V5-IR |
| IRRIGATE R ONLY | V3R-IR-V6 | V1-V2-V3L-V4-V5-IL |
| EMERGENCY DEFLATION | V6 | V1-V2-V3L-V3R-V4-V5-IL-IR |

EXTERNAL EAR CANAL PRESSURE REGULATION SYSTEM

This United States Non-Provisional Patent Application is a continuation-in-part of U.S. Non-Provisional patent application Ser. No. 14/292,469, filed May 30, 2014, and claims the benefit of U.S. Provisional Patent Application No. 61/983,865, filed Apr. 24, 2014, U.S. Provisional Patent Application No. 61/863,317, filed Aug. 7, 2013, and U.S. Provisional Patent Application No. 61/841,111, filed Jun. 28, 2013, each hereby incorporated by reference herein.

I. BACKGROUND OF THE INVENTION

Pain or discomfort associated with a disorder, including neurologically-mediated disorders such as craniofacial pain syndromes or headache syndromes, may negatively impact the quality of life of the sufferer. In addition to the burden upon the individual, chronic neurological conditions may be a significant strain upon family members, employers, and the healthcare system.

Regarding migraine headaches, concomitant symptoms such as pain, nausea, aura, photophobia, dysesthesias, dizziness, vertigo, and dysequilibrium may represent a significant burden to the population. Epidemiological studies indicate that, in the United States, approximately 18% of women and 6% of men experience frequent migraine headaches and 2% of the general population suffer from chronic migraine headaches. Additionally, persons suffering with chronic migraine headaches or other headaches of similar severity and disability may be at a significantly greater risk for depression and attempted suicide. Thus, it is prudent for clinicians and researchers to continue searching for effective devices and methods to alleviate the symptoms associated with these disorders or to treat the disorders.

Standard pharmaceutical therapies for migraine headaches may generally be prescribed to prevent pain or to relieve pain. The various agents which fall under these two broad categories may exhibit a wide range of effectiveness and also incur varying degrees of side effects. From the perspective of economics, the expense of these medications may be a major source of financial burden on the consumer. Moreover, advanced interventions such as botulinum toxin injections, nerve blockades, neurosurgical alterations, and implanted electrical stimulators may significantly increase costs associated with treatment, while subjecting patients to potential changes in their anatomy and physiology, with no guarantee of complete or permanent symptomatic relief or disorder resolution.

There is a burgeoning field of understanding and applications within the neurosciences which seek to affect positive physiological changes in the nervous system through non-pharmaceutical and non-surgical applications. This field of 'functional neurology' views the human nervous system as a receptor driven system, which may be activated and stimulated in specific ways to produce adaptive, long-term changes through the process of neuroplasticity. This approach to neurorehabilitation utilizes, but not necessarily exclusively includes, various forms and patterns of receptor activation or deactivation to promote positive neurophysiological adaptations within the central nervous system, including the brain, brainstem, and spinal cord, which may promote physiological function of associated tissues, organs, and systems.

There would be a substantial advantage in providing a device or methods which can generate one or more stimuli which can alleviate one or more symptoms associated with a disorder, such as craniofacial pain syndromes or headache syndromes, or treat one or more disorders.

II. SUMMARY OF THE INVENTION

A broad object of particular embodiments of the invention can be to provide an external ear canal pressure regulation device including a fluid flow generator capable of generating a fluid flow and an earpiece having an axial earpiece conduit which communicates between an earpiece first end and an earpiece second end, the axial earpiece conduit fluidically coupled to the fluid flow generator, the earpiece having a complaint earpiece external surface configured to sealably engage an external ear canal of an ear as a barrier between an external ear canal pressure and an ambient pressure.

Another broad object of particular embodiments of the invention can be to provide an external ear canal pressure regulation device having the fluid flow generator capable of generating a pressure differential between the external ear canal and the ambient pressure.

Another broad object of particular embodiments of the invention can be to provide an external ear canal pressure regulation device having the fluid flow generator capable of generating a pressure differential amplitude oscillation which reciprocally drives the fluid flow between a fluid flow first direction and a fluid flow second direction in the axial earpiece conduit.

Another broad object of particular embodiments of the invention can be to provide an external ear canal pressure regulation device including a fluid flow temperature regulator fluidically coupled between the fluid flow generator and the axial earpiece conduit, the fluid flow temperature regulator operable to regulate a fluid flow temperature of the fluid flow.

Another broad object of particular embodiments of the invention can be to provide an external ear canal pressure regulation device including a fluid flow generator capable of generating a fluid flow and a plurality of earpieces, each having an axial earpiece conduit which communicates between an earpiece first end and an earpiece second end, each axial earpiece conduit fluidically coupled to the fluid flow generator, each earpiece having a complaint earpiece external surface configured to sealably engage an external ear canal of an ear as a barrier between an external ear canal pressure and an ambient pressure.

Another broad object of particular embodiments of the invention can be to provide an external ear canal pressure regulation device including a plurality of fluid flow generators capable of generating a corresponding plurality of fluid flows and a plurality of earpieces, each having an axial earpiece conduit which communicates between an earpiece first end and an earpiece second end, each axial earpiece conduit fluidically coupled to a fluid flow generator, each earpiece having a complaint earpiece external surface configured to sealably engage an external ear canal of an ear as a barrier between an external ear canal pressure and an ambient pressure.

Another broad object of particular embodiments of the invention can be to provide an external ear canal pressure regulation device including a memory element and a processor in communication with the memory element, the memory element containing a computer code executable to regulate operation of one or more fluid flow generators.

Another broad object of particular embodiments of the invention can be to provide an external ear canal pressure regulation device having computer code executable to provide a transceiver controller which communicates with a transceiver capable of wireless connection with a controller device discrete from the external ear canal pressure regulation device.

Naturally, further objects of the invention are disclosed throughout other areas of the specification, drawings, and claims.

III. BRIEF DESCRIPTION OF THE DRAWINGS

FIG. 19 is a perspective view of a particular embodiment of an earpiece of an external ear canal pressure regulation device.

FIG. 20 is an exploded view of the particular embodiment of the earpiece of the external ear canal pressure regulation device shown in FIG. 18.

FIG. 21 is a first side view of a particular embodiment of an earpiece of an external ear canal pressure regulation device.

FIG. 22 is a second side view of a particular embodiment of an earpiece of an external ear canal pressure regulation device.

FIG. 23 is a top view of a particular embodiment of an earpiece of an external ear canal pressure regulation device.

FIG. 24 is a bottom view of a particular embodiment of an earpiece of an external ear canal pressure regulation device.

FIG. 25 is a first end view of a particular embodiment of an earpiece of an external ear canal pressure regulation device.

FIG. 26 is a second end view of a particular embodiment of an earpiece of an external ear canal pressure regulation device.

FIG. 32 is a first side view of a particular embodiment of an external ear canal pressure regulation device.

FIG. 33 is a second side view of a particular embodiment of an external ear canal pressure regulation device.

FIG. 37A is a positive pressure regulation profile which can be generated by a particular embodiment of an external ear canal pressure regulation device.

FIG. 37B is a positive pressure regulation profile which can be generated by a particular embodiment of an external ear canal pressure regulation device.

FIG. 37C is a positive pressure regulation profile which can be generated by a particular embodiment of an external ear canal pressure regulation device.

FIG. 37D is a positive pressure regulation profile which can be generated by a particular embodiment of an external ear canal pressure regulation device.

FIG. 37E is a positive pressure regulation profile which can be generated by a particular embodiment of an external ear canal pressure regulation device.

FIG. 37F is a positive pressure regulation profile which can be generated by a particular embodiment of an external ear canal pressure regulation device.

FIG. 37G is a positive pressure regulation profile which can be generated by a particular embodiment of an external ear canal pressure regulation device.

FIG. 38A is a negative pressure regulation profile which can be generated by a particular embodiment of an external ear canal pressure regulation device.

FIG. 38B is a negative pressure regulation profile which can be generated by a particular embodiment of an external ear canal pressure regulation device.

FIG. 38C is a negative pressure regulation profile which can be generated by a particular embodiment of an external ear canal pressure regulation device.

FIG. 38D is a negative pressure regulation profile which can be generated by a particular embodiment of an external ear canal pressure regulation device.

FIG. 38E is a negative pressure regulation profile which can be generated by a particular embodiment of an external ear canal pressure regulation device.

FIG. 38F is a negative pressure regulation profile which can be generated by a particular embodiment of an external ear canal pressure regulation device.

FIG. 38G is a negative pressure regulation profile which can be generated by a particular embodiment of an external ear canal pressure regulation device.

FIG. 39A is a pressure regulation profile which can be generated by a particular embodiment of an external ear canal pressure regulation device.

FIG. 39B is a pressure regulation profile which can be generated by a particular embodiment of an external ear canal pressure regulation device.

FIG. 39C is a pressure regulation profile which can be generated by a particular embodiment of an external ear canal pressure regulation device.

FIG. 39D is a pressure regulation profile which can be generated by a particular embodiment of an external ear canal pressure regulation device.

FIG. 39E is a pressure regulation profile which can be generated by a particular embodiment of an external ear canal pressure regulation device.

FIG. 40 is a valve position schedule for the particular embodiment of the invention shown in FIG. 28.

IV. DETAILED DESCRIPTION OF THE INVENTION

Figure 1:
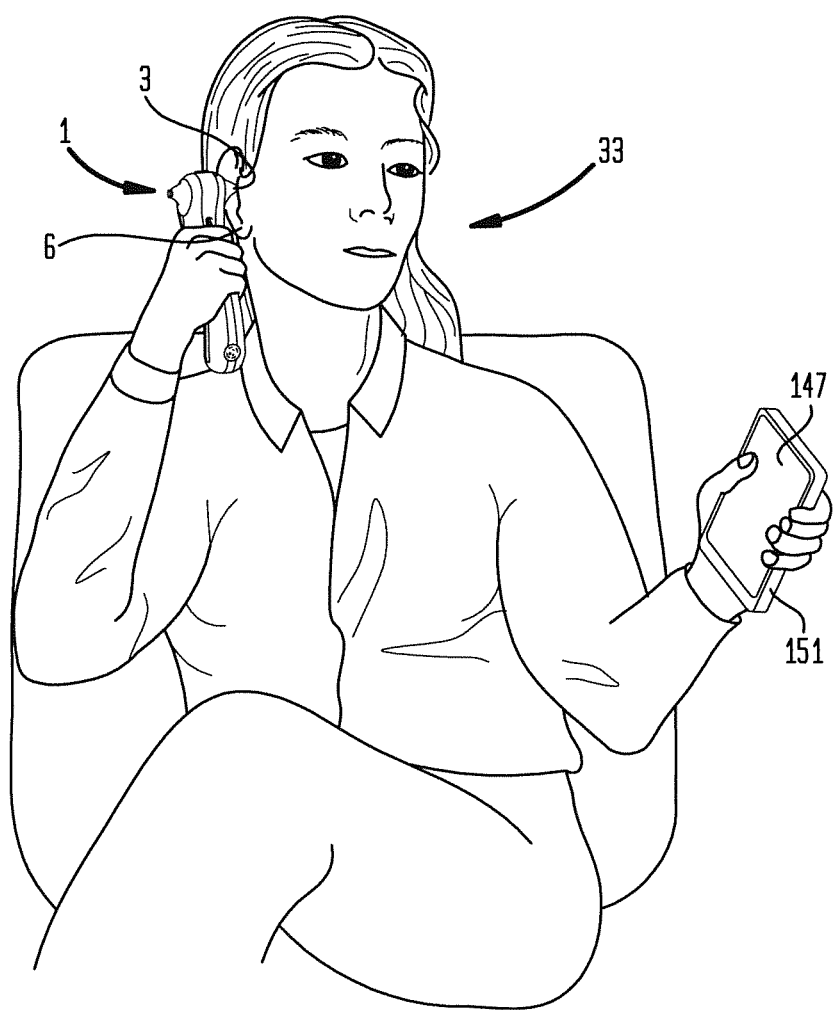
FIG. 1 is an illustration of a method of using a particular embodiment of the external ear canal pressure regulation device.

Now referring primarily to FIG. 1, FIG. 4, FIG. 5A, and FIG. 8, which illustrate a particular method of using an external ear canal pressure regulation device (1) including a first fluid flow generator (2) and a first earpiece (3) having a first axial earpiece conduit (4) fluidicly coupled to the first fluid flow generator (2). A particular method of use can include sealably engaging a first external ear canal (5) of a first ear (6) with a first earpiece external surface (7) of the first earpiece (3), generating a first fluid flow (8) between the first fluid flow generator (2) and the first axial earpiece conduit (4), and regulating a first pressure differential (9) between a first external ear canal pressure (10) of a first ear (6) and an ambient pressure (11). The first pressure differential (9) can be effective to alleviate one or more disorder symptoms or to treat one or more disorders.

Now referring primarily to FIG. 2, FIG. 5A, FIG. 5B, and FIG. 8, which illustrate a particular method of using an external ear canal pressure regulation device (1) including a first fluid flow generator (2), a first earpiece (3), and a second earpiece (12), each of the first and second earpieces (3)(12) having corresponding first and second axial earpiece conduits (4)(13) fluidicly coupled to the first fluid flow generator (2). The method of use can include sealably engaging a first external ear canal (5) of a first ear (6) with a first earpiece external surface (7) of the first earpiece (3), sealably engaging a second external ear canal (14) of a second ear (15) with a second earpiece external surface (16) of the second earpiece (12), generating a first fluid flow (8) between the first fluid flow generator (2) and the first and second axial earpiece conduits (4)(13), regulating a first pressure differential (9) between a first external ear canal pressure (10) of the first ear (6) and an ambient pressure (11), and regulating a second pressure differential (17) between a second external ear canal pressure (18) of the second ear (15) and an ambient pressure (11) effective to alleviate one or more disorder symptoms or treat one or more disorders.

Now referring primarily to FIG. 3, FIG. 5A, FIG. 5B, and FIG. 28, which illustrate a particular method of using an external ear canal pressure regulation device (1) including a first fluid flow generator (2), a first earpiece (3) having a first axial earpiece conduit (4) fluidicly coupled to the first fluid flow generator (2), a second fluid flow generator (19), and a second earpiece (12) having a second axial earpiece conduit (13) fluidicly coupled to the second fluid flow generator (19). The method of use can include sealably engaging a first external ear canal (5) of a first ear (6) with a first earpiece external surface (7) of the first earpiece (3), sealably engaging a second external ear canal (14) of the second ear (15) with a second earpiece external surface (16) of the second earpiece (12), generating a first fluid flow (8) between the first fluid flow generator (2) and the first axial earpiece conduit (4), regulating a first pressure differential (9) between a first external ear canal pressure (10) of the first ear (6) and an ambient pressure (11), generating a second fluid flow (20) between the second fluid flow generator (19) and the second axial earpiece conduit (13), and regulating a second pressure differential (17) between a second external ear canal pressure (8) of the second ear (15) and the ambient pressure (11) effective to alleviate one or more disorder symptoms or treat one or more disorders.

The term "pressure differential" for the purposes of this invention means the difference in pressure between two locations.

The term "pressure differential amplitude" for the purposes of this invention means the numerical value of the difference in pressure between two locations. The pressure differential amplitude can be expressed as a number without a sign (positive or negative), regardless of whether the pressure is lesser or greater in the first location relative to the second location. As an illustrative example, a first or second external ear canal pressure (10)(18) of +50 kilopascals above the ambient pressure (11) and a first or second external ear canal pressure (10)(18) of −50 kilopascals below the ambient pressure (11) can both have a first or second pressure differential amplitude (9)(17) of 50 kilopascals.

The term "external ear canal pressure" for the purposes of this invention means forces exerted within the first or second external ear canal (5)(14) and, without limitation to the breadth of the foregoing, means forces exerted within the first or second external ear canal (5)(14) by a fluid volume (21), a pre-selected fluid volume (22) of a first or second fluid flow (8)(20) delivered to or generated in the first or second external ear canal (5)(14) by operation of the external ear canal pressure regulation device (1).

The term "pre-selected" for the purposes of this invention means a parameter which has been prior selected for delivery to, generation in, or administration to the first or second external ear canal (5)(14) by interaction with the external ear canal pressure regulation device (1) and subsequently delivered to, generated in, or administered to a first or second external ear canal (5)(14) by operation of the external ear canal pressure regulation device (1). For example, a preselected fluid volume (22) of 10 milliliters can be prior selected for delivery to the first or second external ear canal (5)(14) by interaction with the external ear canal pressure regulation device (1) and subsequently, a fluid volume (21) of 10 milliliters can be delivered to the first or second external ear canal (5)(14) by operation of the external ear canal pressure regulation device (1).

The term "ambient pressure" for the purposes of this invention means forces exerted external to the first or second external ear canal (5)(14) in the ambient environment and, without limitation to the breadth of the foregoing, means forces exerted on a first or second earpiece (3)(12) on the ambient side of the corresponding first or second barrier (102)(103) created by having the corresponding first or second earpiece external surface (7)(16) sealably engaged with the corresponding first or second external ear canal (5)(14), as herein described.

The term "sealably engaged" for the purposes of this invention means a seal between an earpiece external surface and an external ear canal capable of maintaining a pressure differential, a pressure differential amplitude, or pre-selected pressure differential amplitude over a time period or a pre-selected time period, or pressure regulation profile effective to alleviate one or more disorder symptoms or treat one or more disorders.

The term "symptom" for the purposes of this invention means any discomfort or combination of discomforts associated with a disorder. Without limiting the breadth of the foregoing, symptoms can include: dizziness; vertigo; nausea; imbalance; paresthesia; dysesthesia; sensitivity to light; sensitivity to odor; sensitivity to sound; anxiety; sleeplessness; irritability; fatigue; loss of appetite; blurred vision; gut disturbances; acute pain or chronic pain of varying characteristics including but not limited to throbbing, tearing, sharp, dull, deep, lancinating, burning, aching, stabbing, intense, lightning-like, sense of swelling, or tingling; or the like; or combinations thereof.

The term "disorder" for the purposes of this invention means a physical or mental condition which may not be normal or healthy. Without limiting the breadth of the foregoing, a disorder can include: neuropathic craniofacial pain syndromes such as neuralgias, for example trigeminal neuralgia; temporomandibular joint syndrome; headache syndromes such as migraine headaches, chronic daily headaches, cluster headaches, muscle tension headaches, post-traumatic headaches, or chronic paroxysmal hemicranias; endolymphatic hydrops; vertigo; tinnitus; syndromes resulting from brain injury; syndromes resulting from impaired neurologic function, including cognitive disorders such as attention deficit disorder, emotional disorders such as anxiety disorders, or seizure disorders; phantom limb; middle ear disorders; inner ear disorders; or the like, or combinations thereof.

Now referring primarily to FIG. 8, FIG. 9A, FIG. 9B, FIG. 28, FIG. 29A, and FIG. 29B, particular embodiments of the external ear canal pressure regulation device (1) can include a first fluid flow generator (2), which can have any of a numerous and wide variety of configurations capable of generating a first fluid flow (8) between the first fluid flow generator (2) and a first axial earpiece conduit (4) of a first earpiece (3). As to particular embodiments, the first fluid flow generator (2) can include a volumetrically adjustable element (23) capable of operation between a greater volume and a lesser volume. As an illustrative example, operating the volumetrically adjustable element (23) from a greater volume to a lesser volume can generate a first fluid flow (8) away from the first fluid flow generator (2) whereas operating the volumetrically adjustable element (23) from a lesser volume to a greater volume can generate a first fluid flow (8) toward the first fluid flow generator (2).

As to particular embodiments, the first fluid flow generator (2) can include a positive displacement pump (24), which can be configured as a rotary positive displacement pump, such as a gear pump, a screw pump, or a rotary vane pump; a reciprocating positive displacement pump, such as a plunger pump, a diaphragm pump, or a piston pump; or any pump configuration capable of moving a fluid volume (21) or generating a first fluid flow (8) between the first fluid flow generator (2) and the first axial earpiece conduit (4). As an illustrative example, a positive displacement pump (24) which may be useful in particular embodiments of the external ear canal pressure regulation device (1) may be the SP 100 EC or the SP 100 EC-LC, which can be obtained from Schwarzer Precision GmbH+Co., Am Lichtbogen 7, 45141 Essen, Germany. As an illustrative example, an axial earpiece conduit (4)(13) which may be useful in particular embodiments of the external ear canal pressure regulation device (1) to fluidicly couple to a positive displace pump (24) may be multi-lumen micro-extruded tubing, such multi-lumen micro-extruded tubing which can be obtained from Microspec Corporation, 327 Jaffrey Road, Peterborough, N.H., 03458, USA.

Figure 8:
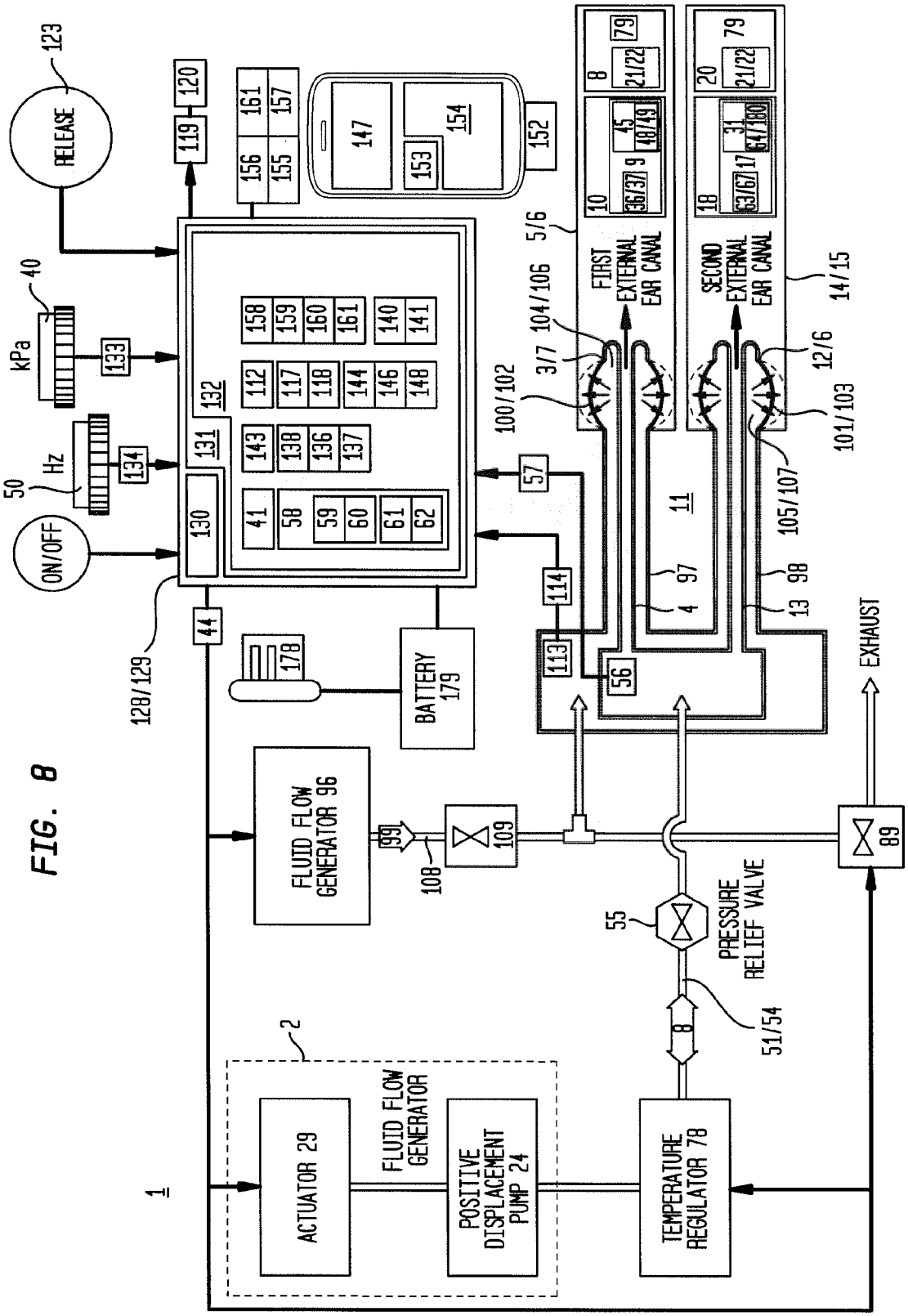
FIG. 8 is a schematic block diagram of the particular embodiment of an external ear canal pressure regulation device shown in FIG. 7 operable to achieve a pressure differential between an external ear canal pressure and an ambient pressure.

Now referring primarily to FIG. 8, FIG. 9A, and FIG. 9B, the first fluid flow generator (2) can be configured as a piston pump (25) in which a piston (26) reciprocally operates in a barrel (27) to adjust a barrel internal volume (28) between a greater volume and a lesser volume. As an illustrative example, the piston (26) can operate to decrease a barrel internal volume (28), thereby generating a first fluid flow (8) away from the first fluid flow generator (2) toward the first axial earpiece conduit (4). As to particular embodiments having the first earpiece external surface (7) sealably engaged with the first external ear canal (5) (as shown in the illustrative examples of FIG. 4 and FIG. 5A), the first fluid flow (8) can egress from the first axial earpiece conduit (4) toward the first external ear canal (5), which can generate a first external ear canal pressure (10) greater than the ambient pressure (11). Conversely, the piston (26) can operate to increase the barrel internal volume (28), thereby generating a first fluid flow (8) from the first axial earpiece conduit (4) toward the first fluid flow generator (2). As to particular embodiments having the first earpiece external surface (7) sealably engaged with the first external ear canal (5), the first fluid flow (8) can ingress to the first axial earpiece conduit (4) from the first external ear canal (5), which can generate a first external ear canal pressure (10) lesser than the ambient pressure (11).

Now referring primarily to FIG. 8 and FIG. 9B, as to particular embodiments, the piston (26) can be operatively coupled to an actuator (29), which can function to move the piston (26) within the barrel (27) to generate a first fluid flow (8) between the first fluid flow generator (2) and the first axial earpiece conduit (4). As to particular embodiments, the actuator (29) can be configured as a linear actuator (30), including a mechanical actuator, a hydraulic actuator, a pneumatic actuator, a piezoelectric actuator, an electro-mechanical actuator, a linear motor, a telescoping linear actuator, or any linear actuator configuration capable of generating linear motion. As an illustrative example, a linear actuator (30) which may be useful in particular embodiments of the external ear canal pressure regulation device (1) may be the miniature linear actuator AS-03, which can be obtained from Lunematic. As to particular embodiments, the linear actuator (30) can be configured as threaded shaft which upon rotation moves linearly. The linear actuator (30) can be disposed adjacent the barrel (27) of the first fluid flow generator (2). The linear motion of the threaded shaft can be coupled to the motion of the piston (26) of the first fluid flow generator (2) by a connector (32), whereby linear motion of the threaded shaft causes linear motion of the piston (26) within the barrel (27) to adjust the barrel internal volume (28), generating a first fluid flow (8) between the first fluid flow generator (2) and the first axial earpiece conduit (4).

As to other particular embodiments, the first fluid flow generator (2) can be configured as a diaphragm pump, which can include a diaphragm having a resiliently flexible wall bounding a chamber volume. The resiliently flexible wall in a deformed condition can decrease the chamber volume, thereby generating a first fluid flow (8) away from the first fluid flow generator (2) toward the first axial earpiece conduit (4). As to particular embodiments having the first earpiece external surface (7) sealably engaged with the first external ear canal (5), the first fluid flow (8) can egress from the first axial earpiece conduit (4) toward the first external ear canal (5), which can generate a first external ear canal pressure (10) greater than the ambient pressure (11). Conversely, the resiliently flexible wall can return toward a non-deformed condition from the deformed condition, increasing the chamber volume and thereby generating a first fluid flow (8) toward the first fluid flow generator (2) from the first axial earpiece conduit (4). As to particular embodiments having the first earpiece external surface (7) sealably engaged with the first external ear canal (5), the first fluid flow (8) can ingress to the first axial earpiece conduit (4) from the first external ear canal (5), which can generate a first external ear canal pressure (10) lesser than the ambient pressure (11).

As to particular embodiments, the diaphragm can be a piezoelectric diaphragm, having a resiliently flexible wall which vibrates upon the application of a sine wave voltage. The vibrations can generate a first fluid flow (8), with the first fluid flow (8) having flow rates of up to 0.8 liters per minute and typical amounts of pressure up to 1.5 kilopascals capable of being achieved by a 15 Vp-p 25 kHz signal. The piezoelectric diaphragm can be operated above the normal audible range by a 24-25 kHz signal.

Figure 4:
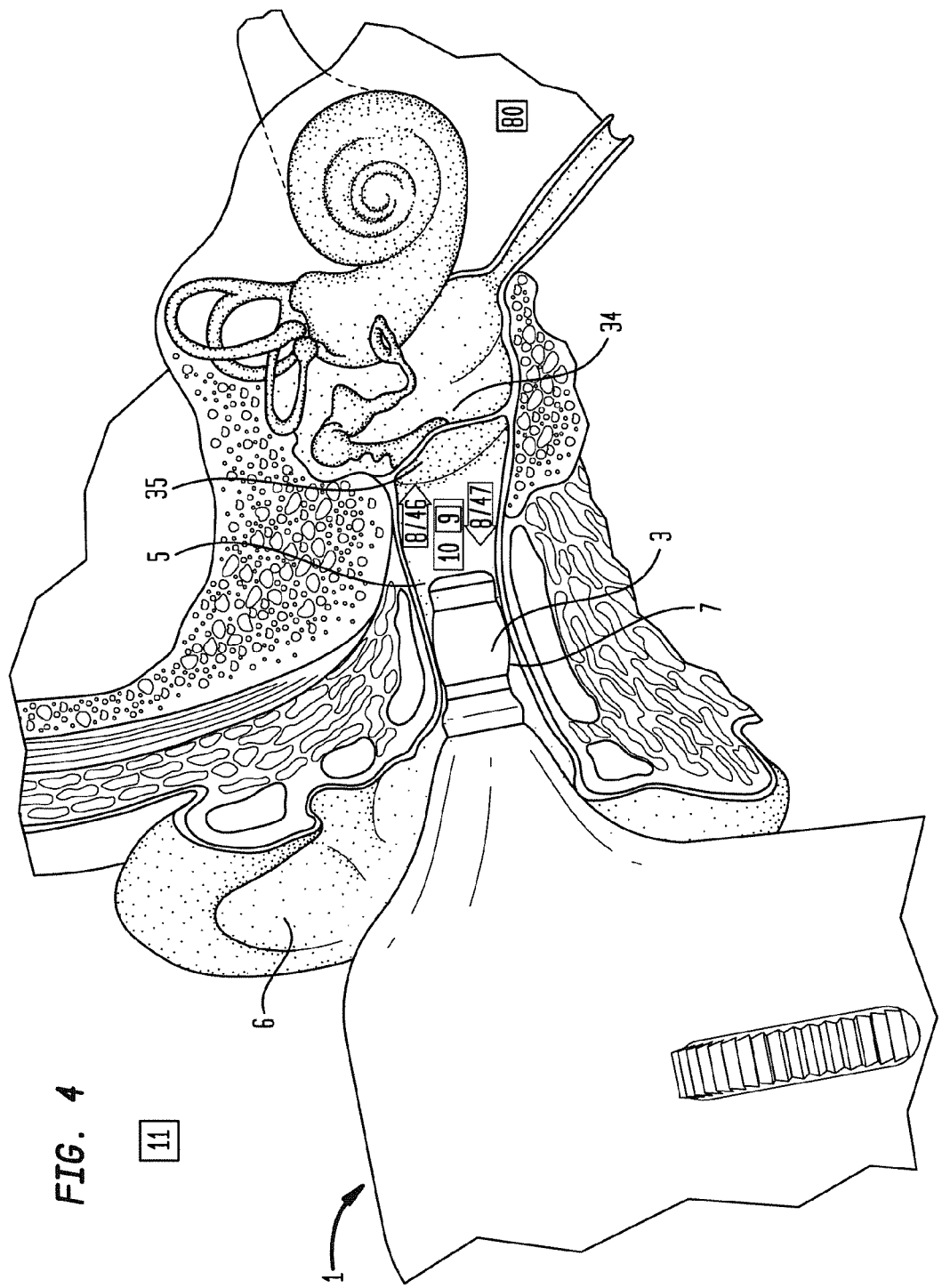
FIG. 4 is an illustration of a particular embodiment of an external ear canal pressure regulation device sealably engaged with the external ear canal.
Figure 5A:
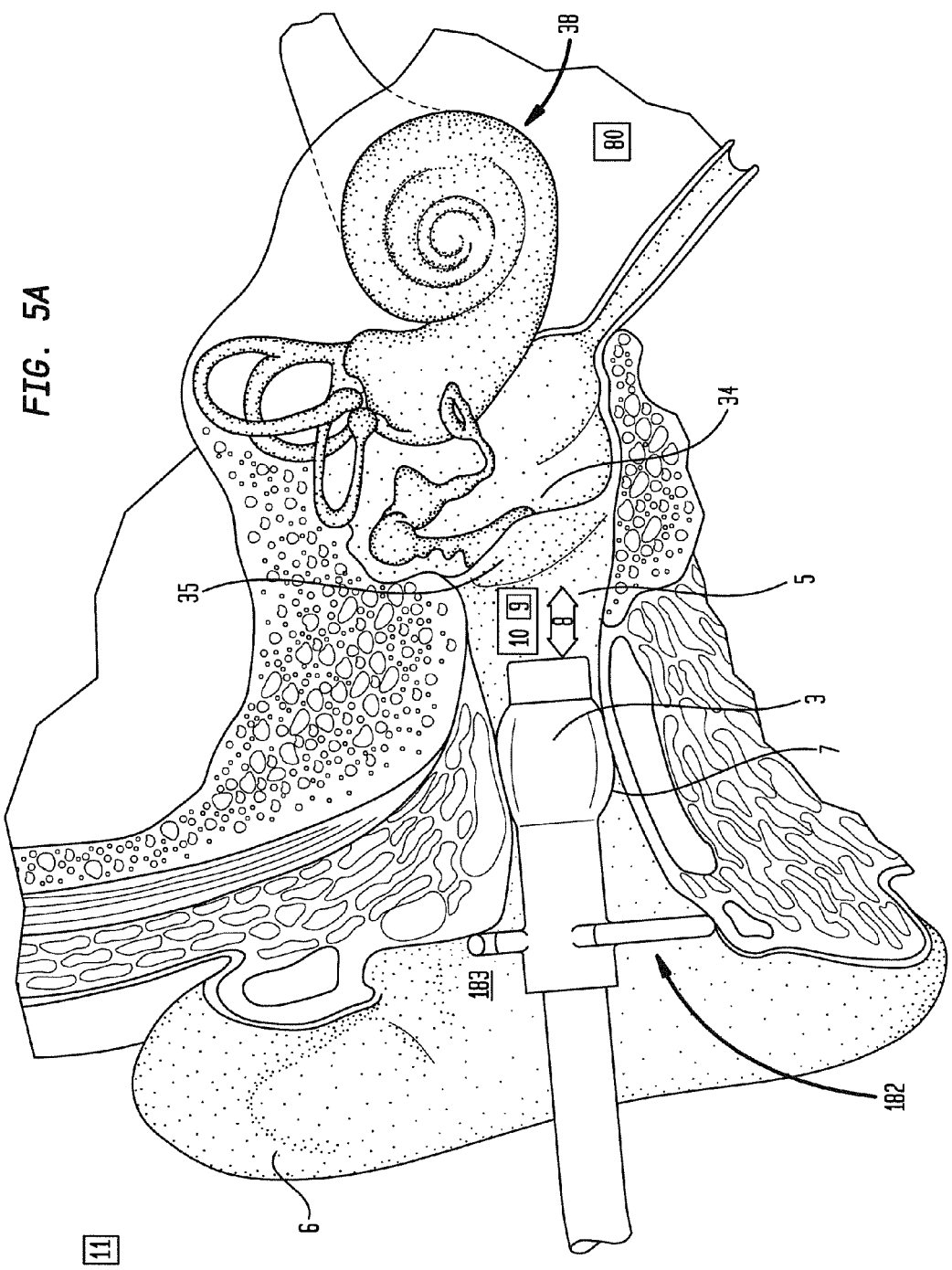
FIG. 5A is an illustration of a particular embodiment of an external ear canal pressure regulation device sealably engaged with a first external ear canal.
Figure 5B:
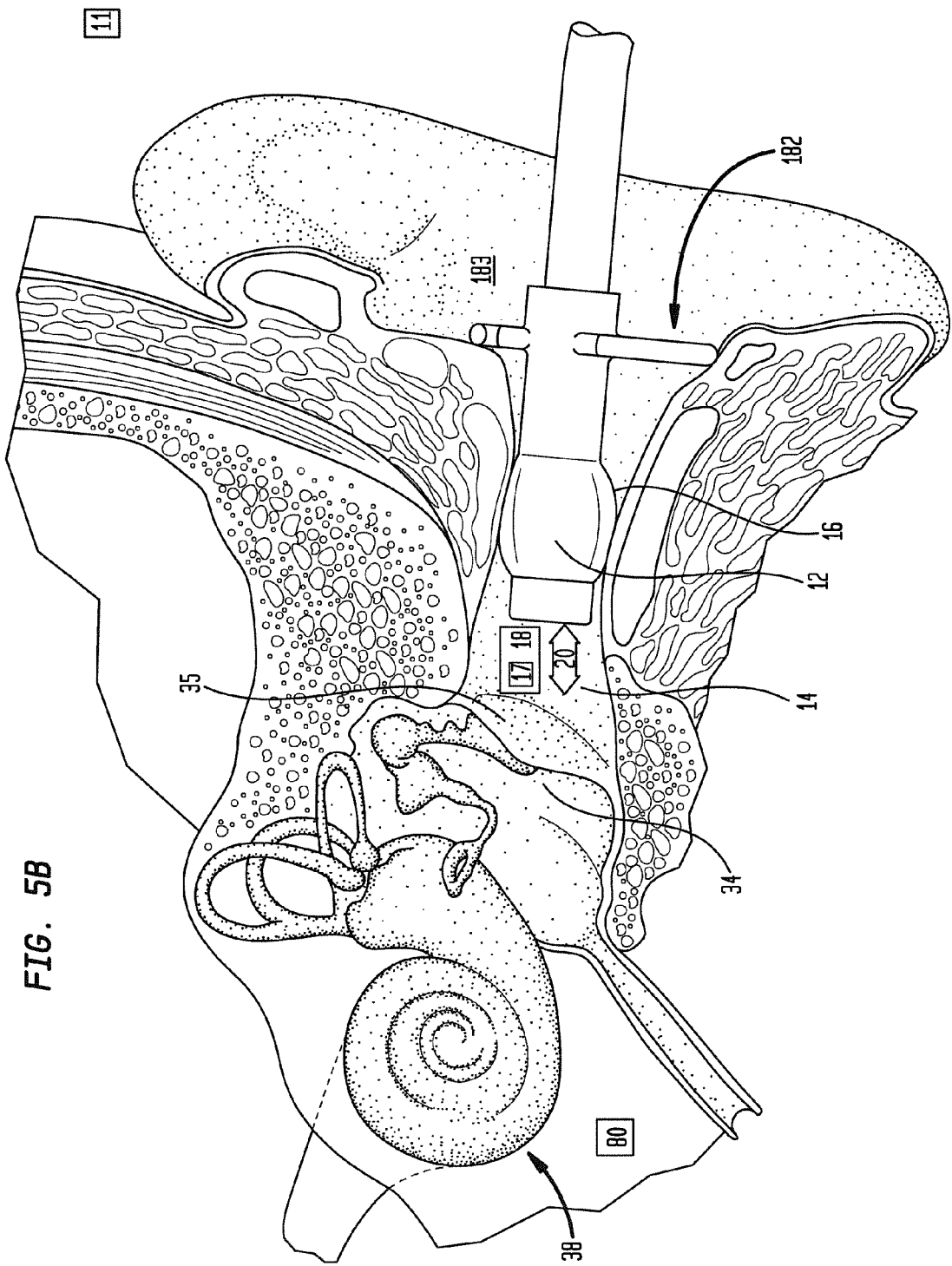
FIG. 5B is an illustration of a particular embodiment of an external ear canal pressure regulation device sealably engaged with a second external ear canal.
Figure 6:
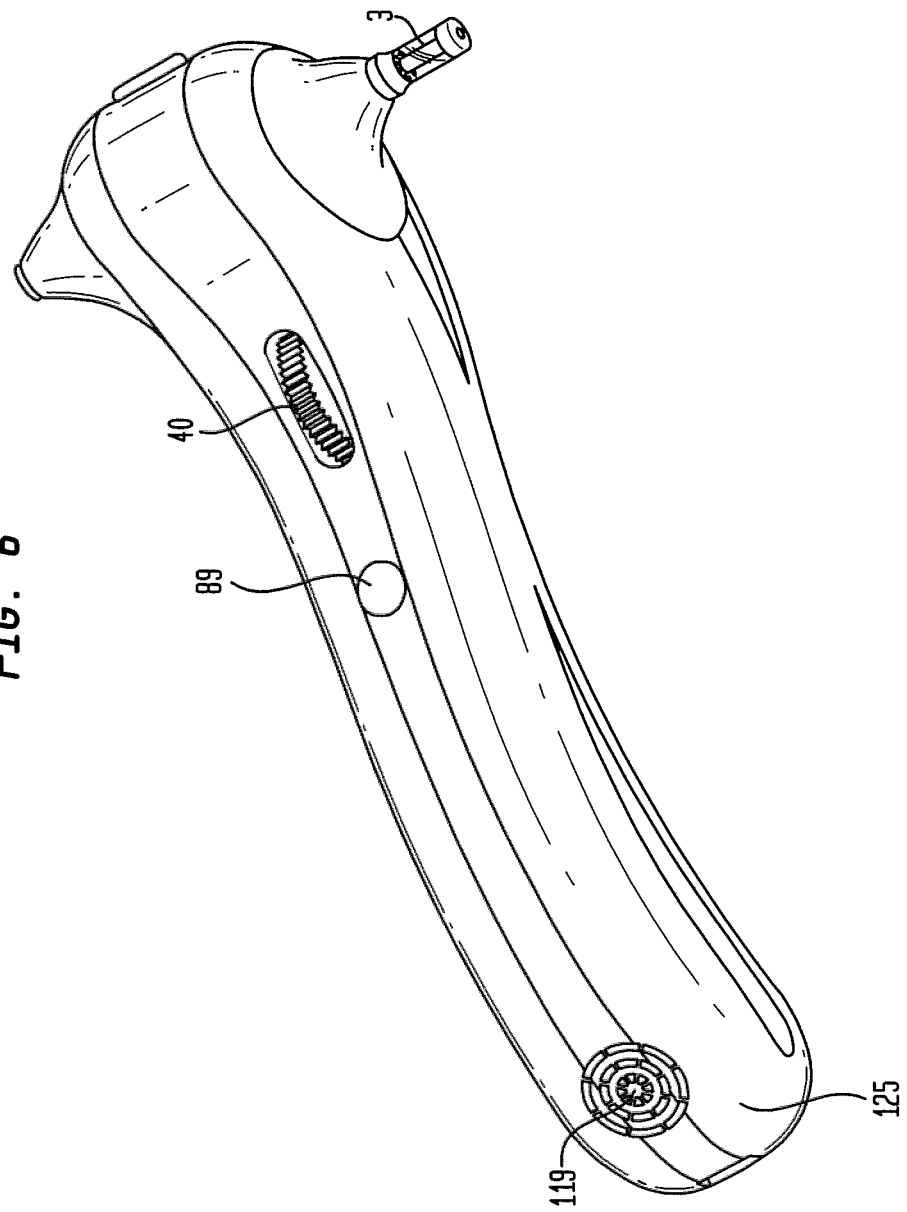
FIG. 6 is a perspective view of a particular embodiment of an external ear canal pressure regulation device.
Figure 7:
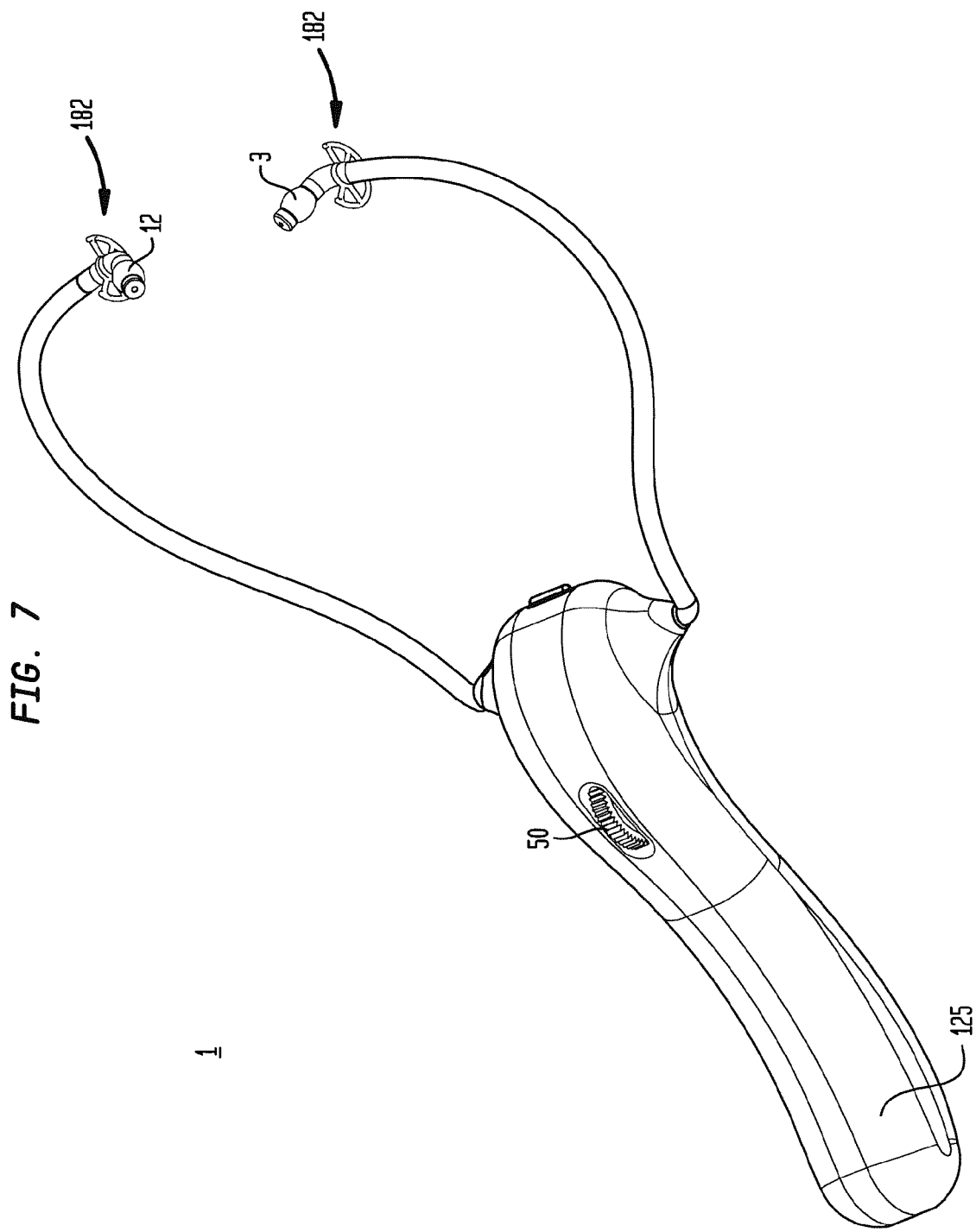
FIG. 7 is a perspective view of a particular embodiment of an external ear canal pressure regulation device.

Now referring primarily to FIG. 4 and FIG. 5A, the first fluid flow generator (2) can be configured to generate a first fluid flow (8) between the first fluid flow generator (2) and the first axial earpiece conduit (4) having fluid volume (21) typically in a range of between 0 milliliters to about 20 milliliters; however, embodiments can have a lesser or greater fluid volume (21) depending upon the application. As to particular embodiments, the fluid volume (21), or a pre-selected fluid volume (22), can selected from one or more of the group including or consisting of: between 0 milliliters to about 2 milliliters, between about 1 milliliter to about 3 milliliters, between about 2 milliliters to about 4 milliliters, between about 3 milliliters to about 5 milliliters, between about 4 milliliters to about 6 milliliters, between about 5 milliliters to about 7 milliliters, between about 6 milliliters to about 8 milliliters, between about 7 milliliters to about 9 milliliters, between about 8 milliliters to about 10 milliliters, between about 9 milliliters to about 11 milliliters, between about 10 milliliters to about 12 milliliters, between about 11 milliliters to about 13 milliliters, between about 12 milliliters to about 14 milliliters, between about 13 milliliters to about 15 milliliters, between about 14 milliliters to about 16 milliliters, between about 15 milliliters to about 17 milliliters, between about 16 milliliters to about 18 milliliters, between about 17 milliliters to about 19 milliliters, and between about 18 milliliters to about 20 milliliters.

One or a plurality fluid volumes (21) (or pre-selected fluid volumes (22)) can be generated with the external ear canal pressure regulation device (1) depending upon the method of use, which can be further influenced by factors such as user (33) anatomy, physiology, or biochemistry of an auditory meatus (34); disorder symptom targeted for alleviation; disorder targeted for treatment; observable effect(s) of using one or a plurality of fluid volumes (21) (or pre-selected fluid volumes (22)) in a particular method of using the external ear canal pressure regulation device (1); or the like; or combinations thereof; whereby the one or the plurality of fluid volumes (21) (or pre-selected fluid volumes (22)) can administered effective to alleviate one or more disorder symptoms or treat one or more disorders, but not so much as to cause discomfort to the user (33) or injury to the auditory meatus (34) or a tympanic membrane (35).

Again referring primarily to FIG. 4 and FIG. 5A, the first fluid flow generator (2) can be capable of generating a first pressure differential (9) between the first external ear canal pressure (10) and the ambient pressure (11). As to particular embodiments, the external ear canal pressure regulation device (1) can be operated to achieve a first external ear canal pressure (10) which can be lesser or greater than the ambient pressure (11). The effective range of the first external ear canal pressure (10) can be from just above or below the ambient pressure (11) increasing to a first external ear canal pressure (10), above or below the ambient pressure (11), just short of causing discomfort to the user (33) or injury to the auditory meatus (34) or the tympanic membrane (35). While authorities vary on the first external ear canal pressure (10) that may result in discomfort to a user (33) or injury to the auditory meatus (34) or the tympanic membrane (35), typically embodiments of the external ear canal pressure regulation device (1) would not be configured to operate in excess of about −50 kilopascals below the ambient pressure (11) or about +50 kilopascals above the ambient pressure (11).

Accordingly, the first fluid flow generator (2) can be capable of generating a first pressure differential (9) having a first pressure differential amplitude (36) in a range of between 0 kilopascals to about 50 kilopascals; however, embodiments can generate a lesser or greater first pressure differential amplitude (36) depending upon the application. As to particular embodiments, the first pressure differential amplitude (36), or a first pre-selected pressure differential amplitude (37), can be selected from one or more of the group including of consisting of: between 0 kilopascals to about 5 kilopascals, between about 2.5 kilopascals to about 7.5 kilopascals, between about 5 kilopascals to about 10 kilopascals, between about 7.5 kilopascals to about 12.5 kilopascals, between about 10 kilopascals to about 15 kilopascals, between about 12.5 kilopascals to about 17.5 kilopascals, between about 15 kilopascals to about 20 kilopascals, between about 17.5 kilopascals to about 22.5 kilopascals, between about 20 kilopascals to about 25 kilopascals, between about 22.5 kilopascals to about 27.5 kilopascals, between about 25 kilopascals to about 30 kilopascals, between about 27.5 kilopascals to about 32.5 kilopascals, between about 30 kilopascals to about 35 kilopascals, between about 32.5 kilopascals to about 37.5 kilopascals, between about 35 kilopascals to about 40 kilopascals, between about 37.5 kilopascals to about 42.5 kilopascals, between about 40 kilopascals to about 45 kilopascals, between about 42.5 kilopascals to about 47.5 kilopascals, and between about 45 kilopascals to about 50 kilopascals.

One or a plurality of first pressure differential amplitudes (36) (or first pre-selected pressure differential amplitudes (37)) can be generated with the external ear canal pressure regulation device (1) depending upon the method of use, which can be further influenced by factors such as user (33) anatomy, physiology, or biochemistry of the auditory meatus (34); disorder symptom targeted for alleviation; disorder targeted for treatment; observable effect(s) of using one or more first pressure differential amplitudes (36) (or first pre-selected pressure differential amplitudes (37)) in a particular method of using the external ear external canal pressure regulation device (1); or the like; or combinations thereof; whereby the one or the plurality of first pressure differential amplitudes (36) (or first pre-selected pressure differential amplitudes (37)) can be administered effective to alleviate one or more disorder symptoms or treat one or more disorders, but not so much as to cause discomfort to the user (33) or injury to the auditory meatus (34) or a tympanic membrane (35).

As to particular embodiments, the first fluid pressure differential (9) generated by the first fluid flow generator (2) can be capable of moving a tympanic membrane (35), which lies across the first external ear canal (5) to separate the first external ear canal (5) from a middle ear (38), effective to alleviate one or more disorder symptoms or treat one or more disorders. The tympanic membrane (35) comprises three layers, including an intermediate layer (lamina propria) which is disposed between an external epidermal layer and an internal mucosal layer. The intermediate layer includes modified mechanioreceptive vaterpacinian corpuscles ("mechanoreceptors"), which can be sensitive to deformation or stretch of the tympanic membrane (35). As such, these mechanoreceptors can function as baroreceptors and transmit afferent signals to the central nervous system associated with inward ("toward the middle ear") or outward ("away from the middle ear") movement of the tympanic membrane (35).

The mechanoreceptors can transmit the afferent signals to the auriculotemporal nerve via A-β pseudounipolar fibers, which subsequently merges with the mandibular nerve. The mandibular nerve converges with the maxillary nerve and the ophthalmic nerve to form the trigeminal ganglion, where the cell bodies of the primary afferent pressure-conveying fibers reside. The afferent fibers are conveyed through the sensory root of the trigeminal nerve to the ventrolateral aspect of the midbelly of the pons. In this way, the trigeminal nerve can transmit sensory signals including nociceptive signals ("pain signals") from the cranium and face to the central nervous system. The afferent fibers then enter the brainstem and synapse on various parts of the trigeminal nuclear system, including the deep lamina of the Trigeminal Nucleus Caudalis, where the afferent fibers can induce GABAergic interneurons to hyperpolarize nociceptive fibers and interneurons in the superficial laminae to block nociceptive transmission.

The first or second pressure differentials (9)(17) between the corresponding first or second external ear canal pressures (10)(18) and the ambient pressure (11) generated by the first fluid flow generator (2) can induce an anti-nociceptive barrage of mechanoreceptor-derived neural impulses such that the various related nuclei of the brainstem pain matrix can become attenuated and resume normal, steady-state activity. Also, parasympathetically-induced intracranial vasodilation can cease, restoring resting vascular flow and tone within the cranial vasculature, a portion of which can be associated with the trigeminal nerve and trigeminal nerve fibers as part of the trigeminal system. In addition to modulating vascular dynamics, biochemical alterations can be induced, such as a down-regulation of inflammatory cytokines or other pain-promoting compounds within or around the cranial vascular beds, whereby the vascular normalization can lead to further quiescence of trigeminal nociceptive afferentation which can culminate in the alleviation of one or more disorder symptoms or treatment of one or more disorders Now referring primarily to FIG. 4 and FIG. 5A, as to particular embodiments of the external ear canal pressure regulation device (1), the first fluid flow (8) in the first external ear canal (5) of the first ear (6) can generate a first external ear canal pressure (10) greater than ambient pressure (11) which causes a corresponding movement of the tympanic membrane (35) toward the middle ear (38), thus increasing the concavity of the tympanic membrane (35). Similarly, the first fluid flow (8) in the first external ear canal (5) of the first ear (6) can generate a first external ear canal pressure (10) lesser than the ambient pressure (11) which causes corresponding movement of the tympanic membrane (35) away from the middle ear (38), thus decreasing the concavity of the tympanic membrane (35). As to particular embodiments or methods, the first or second pressure differentials (9)(17) generated by the first fluid flow generator (2) can move the tympanic membrane (35) toward or away from the middle ear (38) one or a plurality of times within a time period (39).

Movement of the tympanic membrane (35) can stimulate the mechanoreceptors, which can alleviate one or more disorder symptoms or treat one or more disorders. As an illustrative example, tympanic membrane (35) movement can generate a nerve signal which can decrease transmission of a nociceptive signal to the central nervous system, which can result in analgesic stimulation of the central nervous system. As an additional illustrative example, movement of the tympanic membrane (35) can counteract central nervous system habituation.

Now referring primarily to FIG. 8 and FIG. 9B, the external ear canal pressure regulation device (1) can further include a first pressure differential amplitude selection element (40) and a first fluid flow generator controller (41) responsive to operation of the first pressure differential amplitude selection element (40) to regulate operation of the first fluid flow generator (2) to achieve a first pre-selected pressure differential amplitude (37). As an illustrative example, the first pressure differential amplitude selection element (40) can be configured as a variable resistor (42), such as a rheostatically-controlled element (43), which can regulate an electric current by adjusting the resistance of a circuit (current being inversely proportional to resistance for a particular voltage). As such, the rheostatically-controlled element (43) can be used to adjust an electric current to control operation of the first fluid flow generator (2)(whether directly by varying current to the fluid flow generator (2) or indirectly by analyzing variation in current within the circuit to correspondingly generate a fluid flow generator drive signal (44)) to achieve the pre-selected pressure differential amplitude (37). As to particular embodiments, the rheostatically-controlled element (43) can be operated to increase the resistance of the circuit coupled to the first fluid flow generator (2), which can decrease the first pre-selected pressure differential amplitude (37). Conversely, the rheostatically-controlled element (43) can be operated to decrease the resistance of the circuit coupled to the first fluid flow generator (2), which can increase the first pre-selected pressure differential amplitude (37). As to particular embodiments, the rheostatically-controlled element (43) can include a linear rheostat having a linear conductive coil or rotary rheostat having a conductive coil configured as a torus to reduce volume.

Now referring primarily to FIG. 4, the first fluid flow generator (2) can be capable of generating a first pressure differential amplitude oscillation (45), which can reciprocally drive the first fluid flow (8) between a first fluid flow first direction (46) and a first fluid flow second direction (47) in the first axial earpiece conduit (4). As to particular embodiments, the first pressure differential amplitude oscillation (45) can have a first pressure differential amplitude oscillation frequency (48) in a range of between 0 Hertz to about 10 Hertz; however, embodiments can generate a lesser or greater a first pressure differential amplitude oscillation frequency (48) depending upon the application. As to particular embodiments, the first pressure differential amplitude oscillation frequency (48), or a first pre-selected pressure differential amplitude oscillation frequency (49), can be selected from one or more of the group including of consisting of: between 0 Hertz to about 1 Hertz, between about 0.5 Hertz to about 1.5 Hertz, between about 1 Hertz to about 2 Hertz, between about 1.5 Hertz to about 2.5 Hertz, between about 2 Hertz to about 3 Hertz, between about 2.5 Hertz to about 3.5 Hertz, between about 3 Hertz to about 4 Hertz, between about 3.5 Hertz to about 4.5 Hertz, between about 4 Hertz to about 5 Hertz, between about 4.5 Hertz to about 5.5 Hertz, between about 5 Hertz to about 6 Hertz, between about 5.5 Hertz to about 6.5 Hertz, between about 6 Hertz to about 7 Hertz, between about 6.5 Hertz to about 7.5 Hertz, between about 7 Hertz to about 8 Hertz, between about 7.5 Hertz to about 8.5 Hertz, between about 8 Hertz to about 9 Hertz, between about 8.5 Hertz to about 9.5 Hertz, and between about 9 Hertz to about 10 Hertz.

One or a plurality of first pressure differential amplitude oscillation frequencies (48) (or first pre-selected pressure differential amplitude oscillation frequencies (49)) can be generated with the external ear canal pressure regulation device (1) depending upon the method of use, which can be further influenced by factors such as user (33) anatomy, physiology, or biochemistry of the auditory meatus (34); disorder symptom targeted for alleviation; disorder targeted for treatment; observable effect(s) of using one or more first pressure differential amplitude oscillation frequencies (48) (or first pre-selected pressure differential amplitude oscillation frequencies (49)) in a particular method of using the external ear canal pressure regulation device (1); or the like; or combinations thereof; whereby the one or the plurality of first pressure differential amplitude oscillation frequencies (48) (or first pre-selected pressure differential amplitude oscillation frequencies (49)) can be administered effective to alleviate one or more disorder symptoms or treat one or more disorders, but not so much as to cause discomfort to the user (33) or injury to the auditory meatus (34) or a tympanic membrane (35).

Again referring primarily to FIG. 8 and FIG. 9B, the external ear canal pressure regulation device (1) can further include a first pressure differential amplitude oscillation frequency selection element (50). The first fluid flow generator controller (41) can be responsive to operation of the first pressure differential amplitude oscillation frequency selection element (50) to regulate operation of the first fluid flow generator (2) to achieve the first pre-selected pressure differential amplitude oscillation frequency (49). As an illustrative example, the first pressure differential amplitude oscillation frequency selection element (50) can be configured as a variable resistor (42), such as rheostatically-controlled element (43) which can have a similar configuration to the rheostatically-controlled element (43) as described above for the first pressure differential amplitude selection element (40). The variation in current in the circuit can be analyzed to generate a correspondingly varied fluid flow generator drive signal (44) to alter the first pressure differential amplitude oscillation frequency (48) of the first fluid flow (8). Accordingly, as one illustrative example, the rheostatically-controlled element (43) can be operated to increase the resistance of the circuit coupled to the first fluid flow generator (2), which can decrease the first pre-selected pressure differential amplitude oscillation frequency (49). Conversely, the rheostatically-controlled element (43) can be operated to decrease the resistance of the circuit coupled to the first fluid flow generator (2), which can increase the first pre-selected pressure differential amplitude oscillation frequency (49).

Now referring primarily to FIG. 8, FIG. 9B, FIG. 28, FIG. 29A, and FIG. 29B, the external ear canal pressure regulation device (1) can further include a fluid flow manifold (51) interruptible by operation of one or more valves (52) to correspondingly alter the configuration of a manifold fluid flow path (54) within the fluid flow manifold (51) to regulate the first fluid flow (8) (or the second fluid flow (20)) within the fluid flow manifold (51). As an illustrative example, a valve (52) which may be useful in particular embodiments of the external ear canal pressure regulation device (1) may be a solenoid valve such as Lee's High Density Interface (LHD Series) Solenoid Valves, which can be obtained from The Lee Company, 2 Pettipaug Road, Westbrook, Conn., 06498, USA.

While the figures schematically illustrate particular configurations of the fluid flow manifold (51) which correspondingly define particular configurations of the manifold fluid flow path (54), these embodiments need not be so limited in regard to the configuration of the fluid flow manifold (51) or the manifold fluid flow path (54) and embodiments can include any of a wide variety of numerous configurations which can fluidicly couple the first fluid flow generator (2) with the first axial earpiece conduit (4) (or the second fluid flow generator (19) with the second axial earpiece conduit (13)), whether as a plurality of discrete conduits, a one-piece manifold, or defined by a housing (125) whether formed, molded, three-dimensionally printed, or otherwise fabricated as a one-piece construct or assembled from a plurality of pieces into which one or more valves (52) can be disposed, assembled, or otherwise coupled to generate a fluid flow manifold (51) interruptible by operation of one or more valves (52).

A valve (52) can have any type of valve configuration capable of operating between a closed condition and an open condition to unidirectionally regulate the first fluid flow (8) or the second fluid flow (20). A valve (52) can operate between the closed condition, which can be substantially leak-tight to backward flow and substantially leak-tight to forward first fluid flow (8) or second fluid flow (20) on opposed sides of the valve (52), and the open condition, which can have a forward flow in the range of about 0.2 milliliters per second to about 10 milliliters per second, with respect to the first fluid flow (8) or the second fluid flow (20). As to particular embodiments, the pressure differential between opposed sides of the valve (52) or the forward first fluid flow (8) or second fluid flow (20) in the open condition of the valve (52) can be adjusted by the configuration of the valve (52), the unrestricted cross-sectional area of the manifold fluid flow path (54), or the like, or combinations thereof. Additionally, while examples of the external ear canal pressure regulation device (1) disclosed can generate a first pressure differential amplitude (36) of up to about 50 kilopascals in the first external ear canal (5) or a second pressure differential amplitude (63) of up to about 50 kilopascals in the second external ear canal (14), these examples are not intended to teach or suggest that all embodiments of the external ear canal pressure regulation device (1) necessarily achieve this amount of first or second pressure differential amplitudes (36)(63). Rather, certain embodiments of the external ear canal pressure regulation device (1) can be configured to achieve a lesser or greater first or second pressure differential amplitude (36)(63) effective to alleviate one or more disorder symptoms or treat one or more disorders.

Again referring primarily to FIG. 8, FIG. 9B, FIG. 28, and FIG. 29A, the external ear canal pressure regulation device (1) can further include a first pressure relief valve (55) fluidicly coupled to the first axial earpiece conduit (4). The first pressure relief valve (55) in the open condition allows the first external ear canal pressure (10) to return toward the ambient pressure (11), whether from a first external ear canal pressure (10) greater than the ambient pressure (11) or a first external ear canal pressure (10) lesser than the ambient pressure (11). By operating to relieve the first pressure differential (9) when the first pressure differential amplitude (36) exceeds a first pre-selected pressure differential amplitude (37), there can be a reduced risk of discomfort to a user (33) or injury to the auditory meatus (34) or the tympanic membrane (35) when using the external ear canal pressure regulation device (1).

Figure 28:
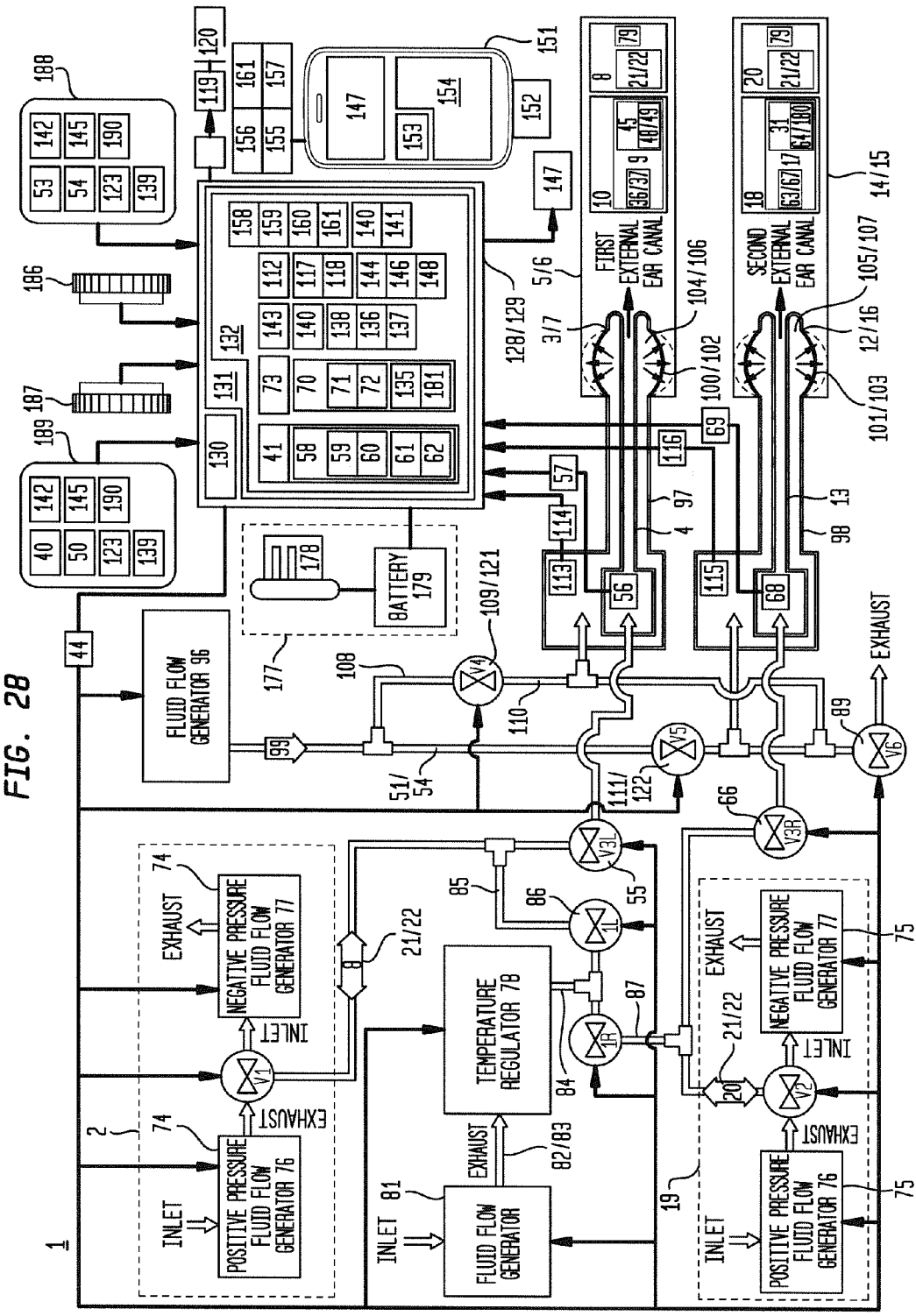
FIG. 28 is a schematic block diagram of the particular embodiment of an external ear canal pressure regulation device shown in FIG. 27 operable to achieve a pressure differential between an external ear canal pressure and an ambient pressure.

Now referring primarily to FIG. 8 and FIG. 28, the external ear canal pressure regulation device (1) can further include a first pressure sensor (56) which can generate a first pressure sensor signal (57) which can vary based upon change in the first pressure differential amplitude (36). As to particular embodiments, a pressure sensor (56) which may be useful in particular embodiments of the external ear canal pressure regulation device (1) may be an EPB small pressure probe sensor, which can be obtained from Measurement Specialties, 45738 Northport Loop West, Fremont, Calif., 94538, USA.

The first pressure sensor signal (57) can be transmitted to a first pressure sensor signal analyzer (58) including a first pressure differential amplitude comparator (59) which functions to compare the first pre-selected pressure differential amplitude (37) to the first pressure differential amplitude (36) actually generated in the first external ear canal (5). As an illustrative example, a user (33) can select a first pre-selected pressure differential amplitude (37) of about 25 kilopascals using the first pressure differential amplitude selection element ( ), as described above. The first pressure differential amplitude comparator (59) can function to compare the first pre-selected pressure differential amplitude (37) of about 25 kilopascals to the first pressure differential amplitude (36) actually generated in the first external ear canal (5). When operation of the first fluid flow generator (2) results in a first pressure differential amplitude (36) in the first external ear canal (5) of about 25 kilopascals within a margin of error, operation of the first fluid flow generator (2) can be curtailed for so long as the first pre-selected pressure differential amplitude (37) can be maintained for the selected time period (39).

As to particular embodiments, the first pressure sensor signal analyzer (58) can further function to generate a first pressure differential amplitude compensation signal (60). For example, when operation of the first fluid flow generator (2) results in a first pressure differential amplitude (36) which varies from the first pre-selected pressure differential amplitude (37), the first pressure sensor signal analyzer (58) can generate a first pressure differential amplitude compensation signal (60) to which the first fluid flow generator controller (41) can be responsive to achieve the first pre-selected pressure differential amplitude (37). As an illustrative example, a user (33) can select a first pre-selected pressure differential amplitude (37) of about 25 kilopascals using the first pressure differential amplitude selection element (40) as described above. Operation of the first fluid flow generator (2) can result in a first pressure differential amplitude (36) of about 20 kilopascals within the first external ear canal (5) due, for example, to improper sealed engagement of the first earpiece external surface (7) with the first external ear canal (5). The first pressure differential amplitude comparator (59) can function to compare the first pre-selected pressure differential amplitude (37) of about 25 kilopascals to the sensed first pressure differential amplitude (36) of about 20 kilopascals. When operation of the first fluid flow generator (2) results in a first pressure differential amplitude (36) which varies from the first pre-selected pressure differential amplitude (37), this instance of 5 kilopascals, the first pressure sensor signal analyzer (58) can generate a first pressure differential amplitude compensation signal (60) which correspondingly drives the first fluid flow generator (2) at a rate which increases the sensed first pressure differential amplitude (36) by about 5 kilopascals to achieve the first pre-selected pressure differential amplitude (37) of about 25 kilopascals.

Again referring primarily to FIG. 8 and FIG. 28, the first pressure sensor signal analyzer (58) can further include a first pressure differential amplitude oscillation frequency comparator (61) which can function to compare the first pre-selected pressure differential amplitude oscillation frequency (49) to the first pressure differential amplitude oscillation frequency (48) sensed by the first pressure sensor (56) in the first external ear canal (5). As an illustrative example, a user (33) can select a first pre-selected pressure differential amplitude oscillation frequency (49) of about 5 Hertz using the first pressure differential amplitude oscillation frequency selection element (50), as described above. The first fluid flow generator controller (2) can be responsive to operation of the first pressure differential amplitude oscillation frequency selection element (50) to regulate operation of the first fluid flow generator (2) to generate a first fluid flow (8) having a first pressure differential amplitude oscillation frequency (48) of about 5 Hertz. The first pressure differential amplitude oscillation frequency comparator (61) can function to compare the first pre-selected pressure differential amplitude oscillation frequency (49) of about 5 Hertz to the first pressure differential amplitude oscillation frequency (48) of about 5 Hertz generated in the first external ear canal (5). When operation of the first fluid flow generator (2) results in a first pressure differential amplitude oscillation frequency (48) corresponding to the first pre-selected pressure differential amplitude oscillation frequency (49) within a margin of error, operation of the first fluid flow generator (2) can be continued without compensation for so long as the sensed first pressure differential amplitude oscillation frequency (48) corresponds to the first pre-selected pressure differential amplitude oscillation frequency (49).

As to particular embodiments, the first pressure sensor signal analyzer (58) can further function to generate a first pressure differential amplitude oscillation frequency compensation signal (62). For example, if operation of the first fluid flow generator (2) results in a first pressure differential amplitude oscillation frequency (48) within the first external ear canal (5) which varies from the first pre-selected pressure differential amplitude oscillation frequency (49), the first pressure sensor signal analyzer (58) can generate a first pressure differential amplitude oscillation frequency compensation signal (62) to control the first fluid flow generator (2) to achieve the first pre-selected pressure differential amplitude oscillation frequency (49).

As an illustrative example, a user (33) can establish a first pre-selected pressure differential amplitude oscillation frequency (49) of about 5 Hertz using the first pressure differential amplitude oscillation frequency selection element (50), as described above. Operation of the first fluid flow generator (2) can result in a first pressure differential amplitude oscillation frequency (48) of about 2.5 Hertz within the first external ear canal (5), due, for example, to improper sealed engagement the first earpiece external surface (7) with the first external ear canal (5). The first pressure differential amplitude oscillation frequency comparator (61) can function to compare the first pre-selected pressure differential amplitude oscillation frequency (49) of about 5 Hertz to the sensed first pressure differential amplitude oscillation frequency (48) of about 2.5 Hertz. If operation of the first fluid flow generator (2) results in a first pressure differential amplitude oscillation frequency (48) which varies from the first pre-selected pressure differential amplitude oscillation frequency (49), in this instance 2.5 Hertz, the first pressure sensor signal analyzer (58) generates a first pressure differential amplitude oscillation frequency compensation signal (62) which drives the first fluid flow generator (2) to increase the first pressure differential amplitude oscillation frequency (48) to achieve the first pre-selected pressure differential amplitude oscillation frequency (49) of about 5 Hertz. When operation of the first fluid flow generator (2) results in a first pressure differential amplitude oscillation frequency (48) which corresponds to the first pre-selected pressure differential amplitude oscillation frequency (49) within a margin of error, operation of the first fluid flow generator (2) can be continued without further generation of a first pressure differential amplitude oscillation frequency compensation signal (62).

Now referring primarily to FIG. 2, FIG. 3, FIG. 5B, FIG. 7, FIG. 8, and FIG. 27 through FIG. 29B, the external ear canal pressure regulation device (1) can further include a second earpiece (12) having a second earpiece external surface (16) configured to sealably engage a second external ear canal (14) of a second ear (15) as a barrier between a second external ear canal pressure (18) and the ambient pressure (11). The second earpiece (12) can include a second axial earpiece conduit (13). The second earpiece (12) can be configured as above described for the first earpiece (3).

Figure 9:
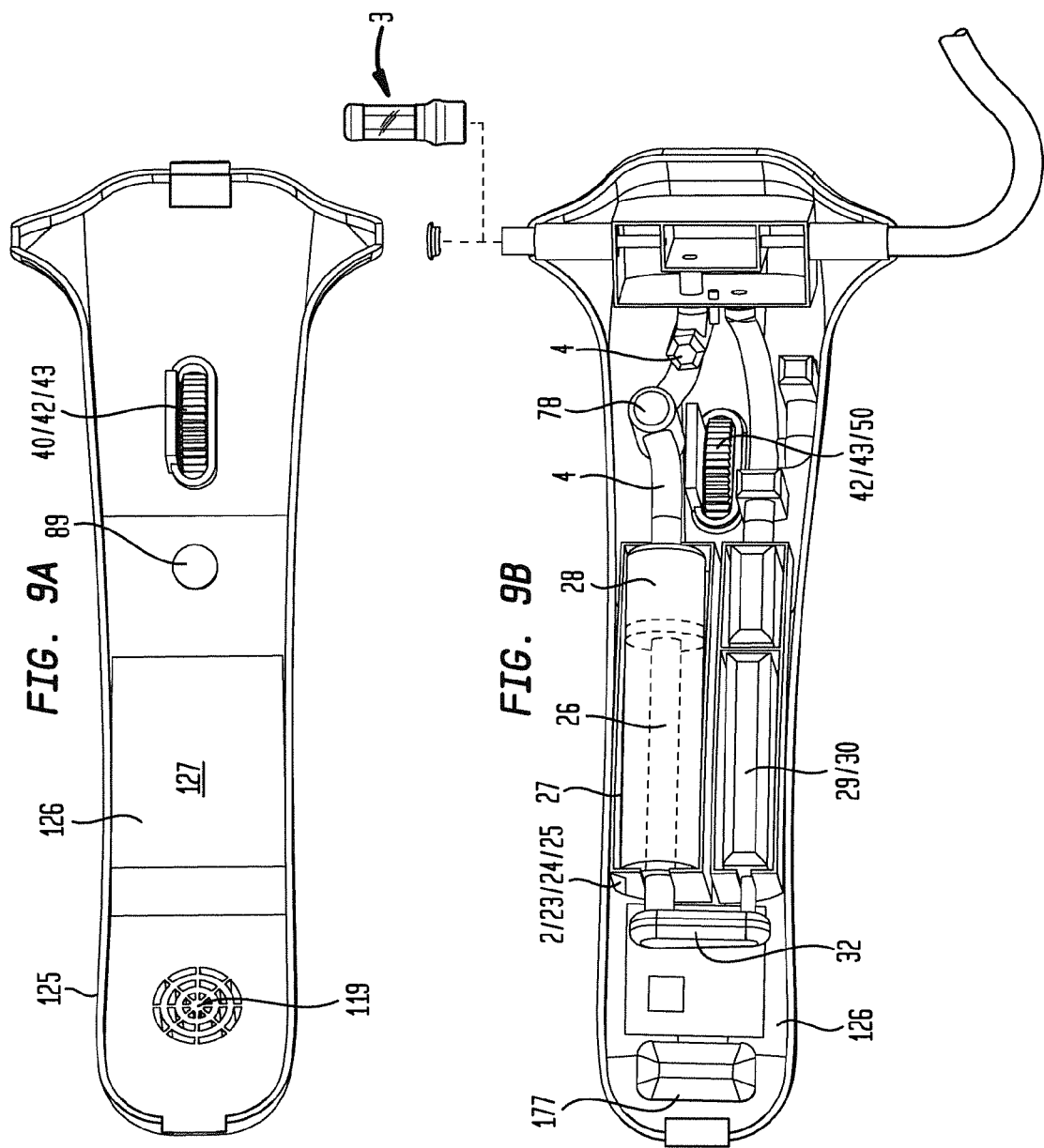
FIG. 9A is a first interior plan view of a particular embodiment of an external ear canal pressure regulation device.
FIG. 9B is a second interior plan view of the particular embodiment of the external ear canal pressure regulation device shown in FIG. 9A.
Figure 10:
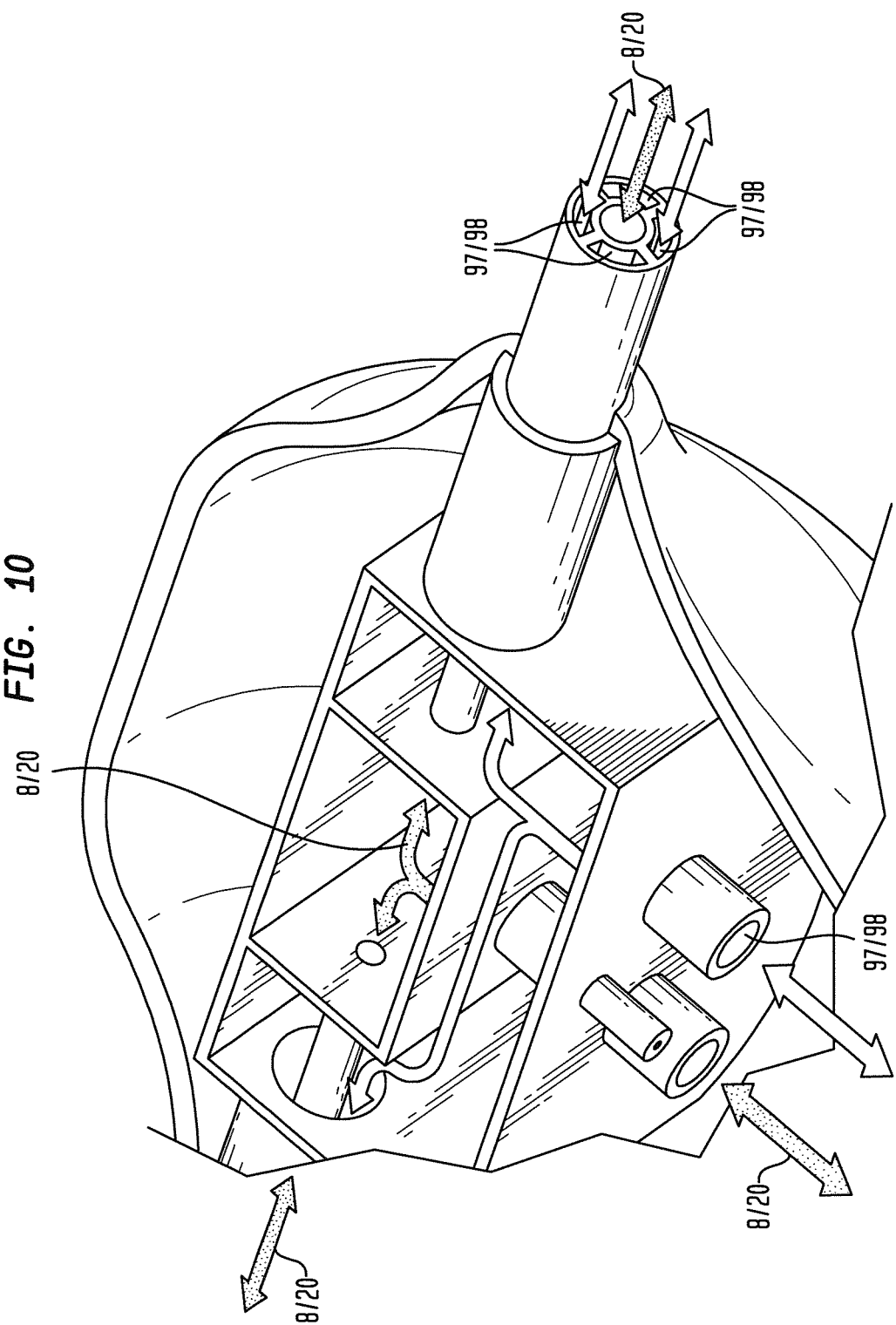
FIG. 10 is an enlarged perspective interior view of the particular embodiment of the external ear canal pressure regulation device shown in FIG. 9B.
Figure 11:
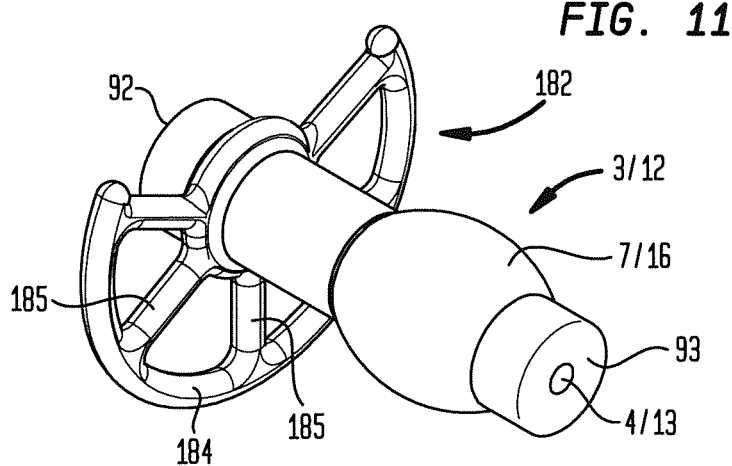
FIG. 11 is a perspective view of a particular embodiment of an earpiece of an external ear canal pressure regulation device.
Figure 12:
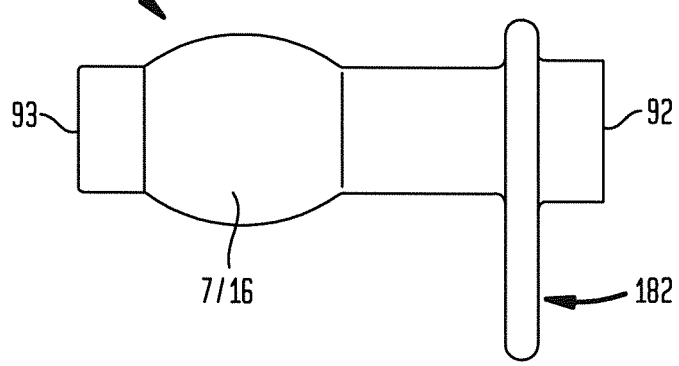
FIG. 12 is a first side view of a particular embodiment of an earpiece of an external ear canal pressure regulation device.
Figure 13:
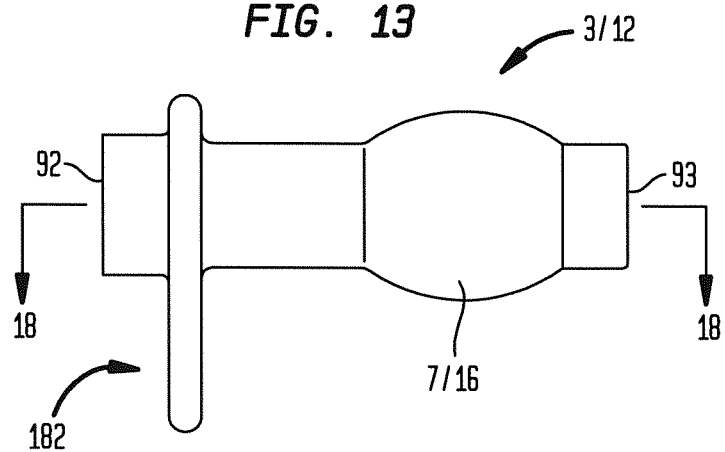
FIG. 13 is a second side view of a particular embodiment of an earpiece of an external ear canal pressure regulation device.
Figure 14:
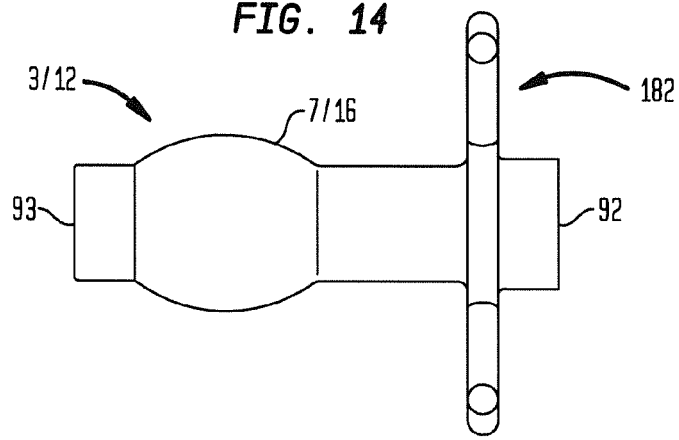
FIG. 14 is a top view of a particular embodiment of an earpiece of an external ear canal pressure regulation device.
Figure 15:
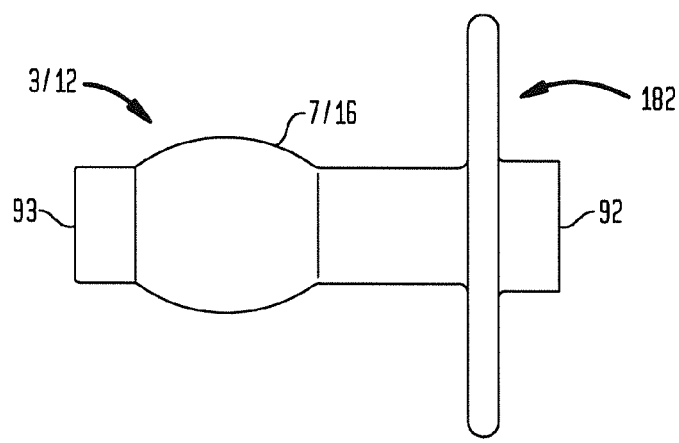
FIG. 15 is a bottom view of a particular embodiment of an earpiece of an external ear canal pressure regulation device.
Figure 16:
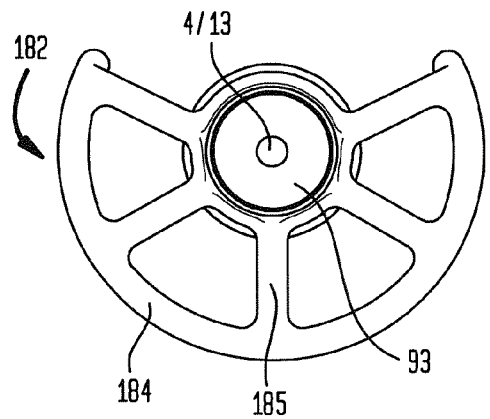
FIG. 16 is a first end view of a particular embodiment of an earpiece of an external ear canal pressure regulation device.
Figure 17:
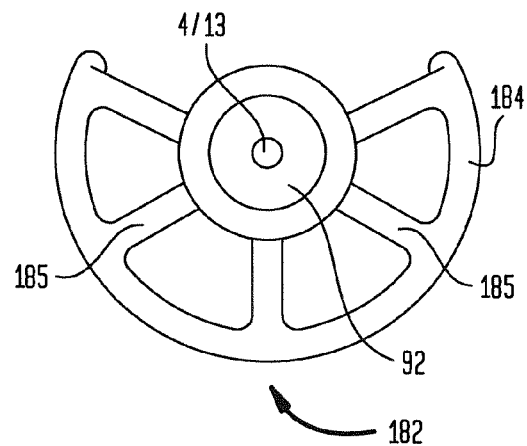
FIG. 17 is a second end view of a particular embodiment of an earpiece of an external ear canal pressure regulation device.
Figure 18:
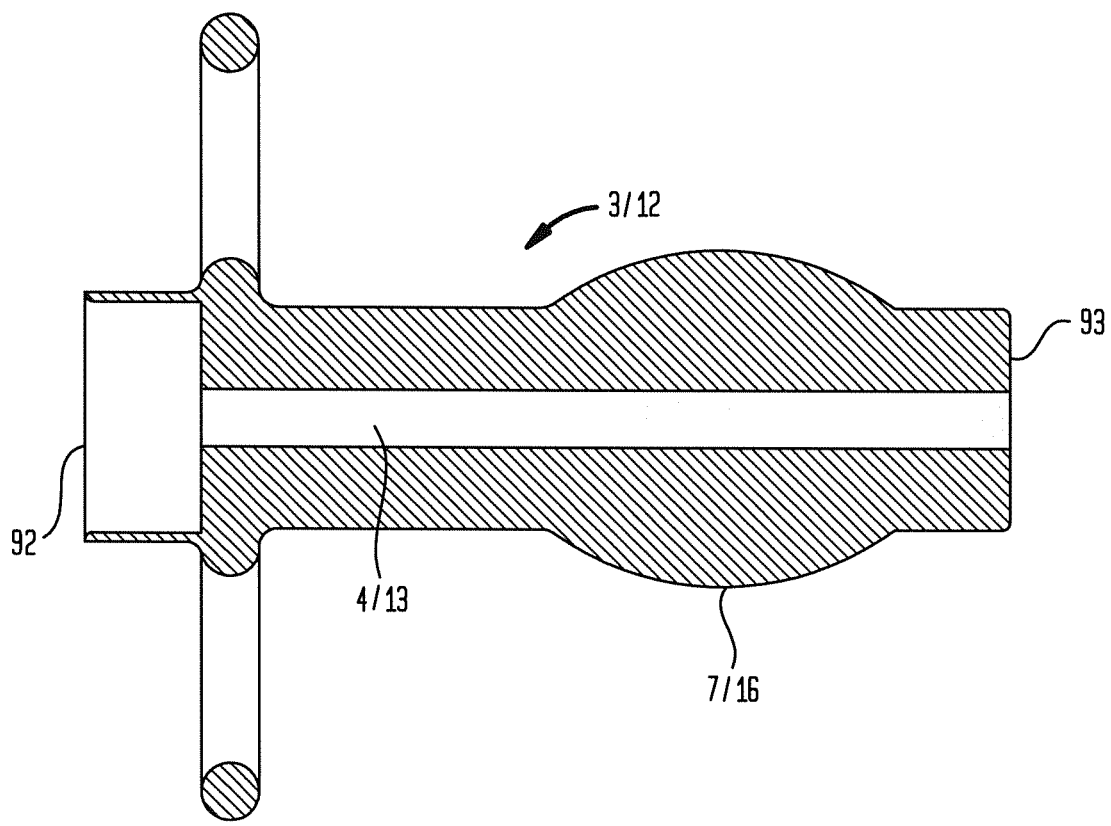
FIG. 18 is a cross section view 18-18 shown in FIG. 13 of a particular earpiece of an external ear canal pressure regulation device.
Figure 27:
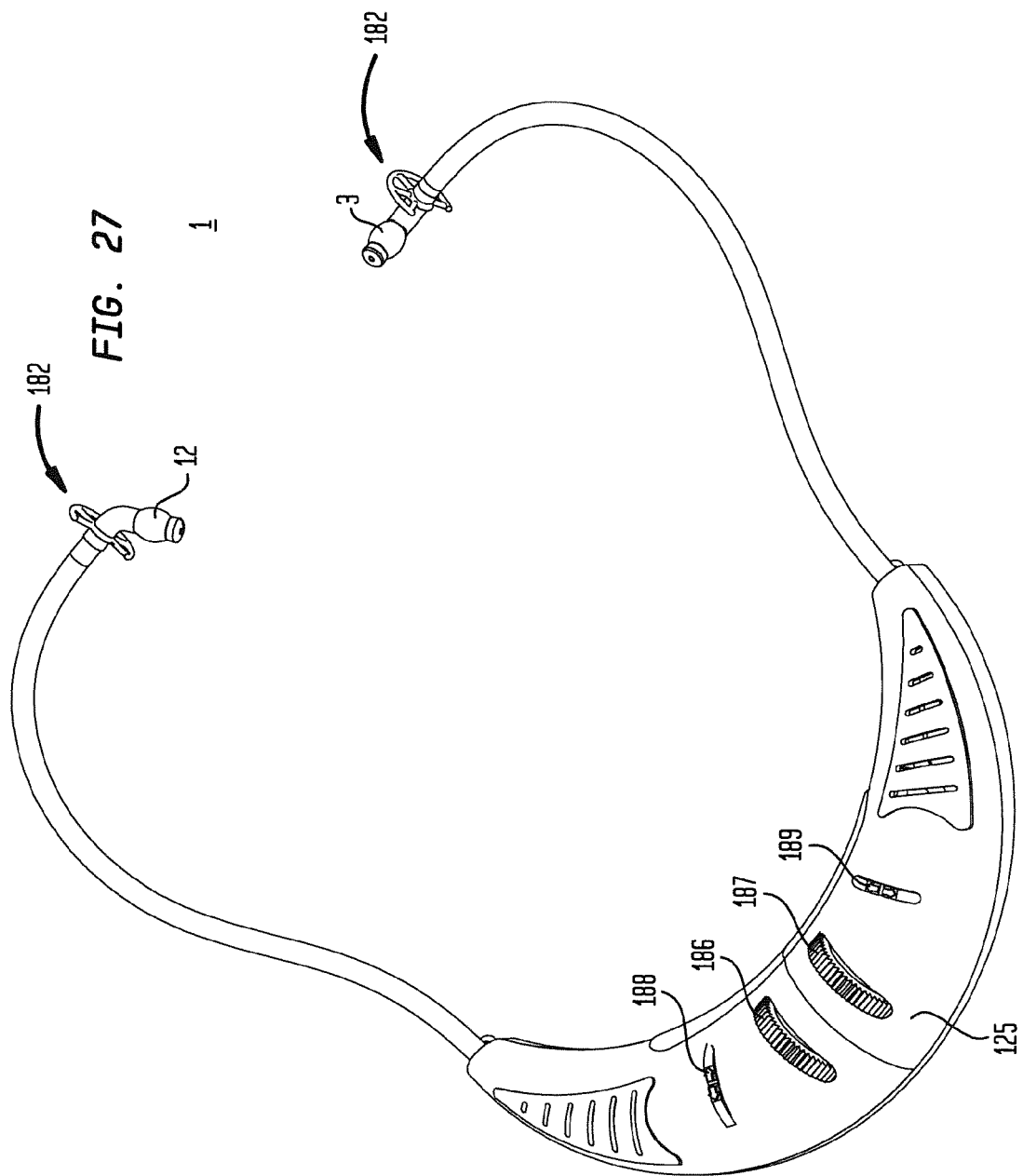
FIG. 27 is a perspective view of a particular embodiment of an external ear canal pressure regulation device.

Now referring primarily to FIG. 8 through FIG. 10, the second axial earpiece conduit (13) can be fluidicly coupled in common to the first fluid flow generator (2). Accordingly, the first fluid flow generator (2) can be capable of generating a second pressure differential (17) between the second external ear canal pressure (18) and the ambient pressure (11) which can have a second pressure differential amplitude (63) and a second pressure differential oscillation frequency (64) which can be substantially similar to or substantially correspond to the first pressure differential amplitude (36) and the first pressure differential oscillation frequency (48), as above described. As an illustrative example, the first fluid flow generator (2) can generate a first pressure differential (9) and a second pressure differential (17), both having a pressure differential amplitude (36)(63) of about 25 kilopascals, and both having a pressure differential amplitude oscillation frequency (48)(64) of about 5 Hertz. Accordingly, operation of the first fluid flow generator (2) can generate a first fluid flow (8) between the first fluid flow generator (2) and the first axial earpiece conduit (4) and between the first fluid flow generator (2) and the second axial earpiece conduit (13). As to particular embodiments, the first earpiece external surface (7) can be sealably engaged with the first external ear canal (5) and the second earpiece external surface (16) can be sealably engaged with the second external ear canal (14). The first fluid flow generator (2) can operate to generate a first fluid flow (8) which egresses from the first axial earpiece conduit (4) toward the first external ear canal (5) and from the second axial earpiece conduit (13) toward the second external ear canal (14), thereby generating a first pressure differential (9) having a first external ear canal pressure (10) greater than the ambient pressure (11) and a second pressure differential (17) having a second external ear canal pressure (18) greater than the ambient pressure (11). Similarly, the first fluid flow generator (2) can be operable to generate a first fluid flow (8) which ingresses to the first axial earpiece conduit (4) from the first external ear canal (5) and ingresses to the second axial earpiece conduit (13) from the second external ear canal (14), thereby generating a first pressure differential (9) having a first external ear canal pressure (10) lesser than the ambient pressure (11) and a second pressure differential (17) having a second external ear canal pressure (18) lesser than the ambient pressure (11).

As to particular embodiments having a first and second axial earpiece conduit (4)(13) fluidicly coupled in common to the first fluid flow generator (2), the first fluid flow generator (2) can be capable of generating a second pressure differential amplitude oscillation frequency (64) substantially similar to the first pressure differential amplitude oscillation frequency (48), as above described.

Now referring primarily to FIG. 27 through FIG. 35, as to particular embodiments, the external ear canal pressure regulation device (1) can include independent first and second fluid flow generators (2)(19) capable of generating discrete first and second fluid flows (8)(20). The second fluid flow generator (19) can be configured and fluidicly coupled to a second axial earpiece conduit (13) of a second earpiece (12) in substantially similar configuration as above described for first fluid flow generator (1) fluidicly coupled to the first axial earpiece conduit (4). Accordingly, the second fluid flow generator (19) can be capable of generating a corresponding discrete second fluid flow (20) independently regulated to generate a second pressure differential (17) having a second pressure differential amplitude (63) and having a second pressure differential amplitude oscillation frequency (64), all of which can have substantially similar ranges as for the first fluid flow (8), above described. Additionally, the second fluid flow generator (19) can be operatively regulated by a second pressure differential amplitude selection element (53) and a second pressure differential amplitude oscillation frequency selection element (54), both of which can be of substantially similar configuration to the corresponding first pressure differential amplitude selection element (40) and first pressure differential amplitude oscillation frequency selection element (50) which operatively regulate the first fluid flow generator (2), as described above.

As to particular embodiments having a second fluid flow generator (19), the external ear canal pressure regulation device (1) can further include a second pressure relief valve (66), which can be of substantially similar configuration to the first pressure relief valve (55), above described. The second pressure relief valve (66) can be fluidicly coupled to the second axial earpiece conduit (13) to relieve the second pressure differential (17) in excess of a second pre-selected pressure differential amplitude (67) of between 0 kilopascals to about 50 kilopascals.

As to particular embodiments having a second fluid flow generator (19), the external ear canal pressure regulation device (1) can further include a second pressure sensor (68), which can be of substantially similar configuration to the first pressure sensor (56), above described. The second pressure sensor (68) can generate a second pressure sensor signal (69) which can vary based upon change in the second external ear canal pressure differential amplitude (63). A second pressure sensor signal analyzer (70), which can be of substantially similar configuration to the first pressure sensor signal analyzer (58), as above described, can include a second pressure differential comparator (71) which functions to compare the second pre-selected pressure differential amplitude (67) to the sensed second pressure differential amplitude (63). The second pressure sensor signal analyzer (70) can generate a second pressure differential amplitude compensation signal (72), whereby a second fluid flow generator controller (73) can be responsive to the second pressure differential compensation signal (72) to control the second fluid flow generator (19) to achieve the second pre-selected pressure differential amplitude (63).

As to particular embodiments, the first fluid flow generator controller (41) and the second fluid flow generator controller (73) can be responsive to signals generated by a plurality of selection elements to control the corresponding first fluid flow generator (2) and the second fluid flow generator (19). As shown in the illustrative examples of FIG. 27 and FIG. 28, an external ear canal pressure regulation device (1) having a first fluid flow generator (2) and a second fluid flow generator (19) can be configured such that the first fluid flow generator controller (41) can be responsive to signals generated by a first selection element (187) and a second selection element (189) and the second fluid flow generator controller (73) can be responsive to signals generated by a third selection element (186) and a fourth selection element (188).

As to particular embodiments, the second pressure sensor signal analyzer (70) can further include a second pressure differential amplitude oscillation frequency comparator (135) which can function to compare a second pre-selected pressure differential amplitude oscillation frequency (180) to the second pressure differential amplitude oscillation frequency (64). The second pressure sensor signal analyzer (70) can generate a second pressure differential amplitude oscillation frequency compensation signal (181), whereby the second fluid flow generator controller (73) can be responsive to the second pressure differential amplitude oscillation frequency compensation signal (181) to control the second fluid flow generator (19) to achieve the second pre-selected pressure differential amplitude oscillation frequency (180).

Now referring primarily to FIG. 28, the external ear canal pressure regulation device (1) including a first fluid flow generator (2), a first earpiece (3) having a first axial earpiece conduit (4) fluidicly coupled to the first fluid flow generator (2) and a second earpiece (12) having a second axial earpiece conduit (13) fluidicly coupled to the second fluid flow generator (19) can be operable to generate a first pressure differential (9) in a first external ear canal (5) and a second pressure differential (17) in a second external ear canal (14) by generating corresponding discrete first and second fluid flows (8)(20), the first fluid flow (8) between the first fluid flow generator (2) and the first axial earpiece conduit (4) and the second fluid flow (20) between the second fluid flow generator (19) and the second axial earpiece conduit (13).

Now referring primarily to FIG. 28 and FIG. 40, as to particular embodiments of the external ear canal pressure regulation device (1) having the configuration shown in FIG. 27 through FIG. 35, to generate a first pressure differential (9) and a second pressure differential (17), valves V1, V2, V3L, V3R, V4, and V5 can be in the open condition and valves V6, 1L, and 1R can be in the closed condition. As to other particular embodiments, to only generate a first pressure differential (9) in the first external ear canal (5), valves V1, V3L, and V4 can be in the open condition and valves V2, V3R, V5, V6, 1L, and 1R can be in the closed condition. As to other particular embodiments, to only generate a second ear canal pressure differential (17) in the second external ear canal (14), valves V2, V3R, and V5 can be in the open condition and valves V1, V3L, V4, V6, 1L, and 1R can be in the closed condition.

As to particular embodiments having a first fluid flow generator (2) and a second fluid flow generator (19), each of the first and second fluid flow generators (2)(19) can include a corresponding first and second pair of fluid flow generators (74)(75) correspondingly fluidicly coupled to the first and second axial earpiece conduits (4)(13). Each of the first and second pair of fluid flow generators (74)(75) can include one positive pressure fluid flow generator (76) and one negative pressure fluid flow generator (77). The positive pressure fluid flow generators (76) can generate first and second fluid flows (8)(20) which egress from the corresponding first and second axial earpiece conduits (4)(13) toward the corresponding first and second external ear canals (5)(14). Accordingly, the first and second fluid flows (8)(20) can flow into the corresponding first and second external ear canals (5)(14), generating corresponding first and second pressure differentials (9)(17) whereby the corresponding first and second external ear canal pressures (10)(18) can be greater than the ambient pressure (11). The negative pressure fluid flow generators (77) can generate first and second fluid flows (8)(20) which ingress to the corresponding first and second axial earpiece conduits (4)(13) from the corresponding first and second external ear canals (5)(14). Accordingly, the first and second fluid flows (8)(19) can flow away from the corresponding first and second external ear canals (5)(14), generating corresponding first and second pressure differentials (9)(17) whereby the corresponding first and second external ear canal pressures (10)(18) can be lesser than the ambient pressure (11).

Now referring primarily to FIG. 8 and FIG. 9B, as to particular embodiments, a fluid flow temperature regulator (78) can be fluidicly coupled to the first fluid flow generator (2). The fluid flow temperature regulator (78) can be operated to generate a first fluid flow (8) or a second fluid flow (19) having a fluid flow temperature (79) greater than a body temperature (80). The first fluid flow (8) having a fluid flow temperature (79) greater than a body temperature (80) can flow through the first axial earpiece conduit (4) or the second axial earpiece conduit (13), egressing from the first axial earpiece conduit (4) or the second axial earpiece conduit (13) toward the corresponding first or second external ear canal (5)(14). Accordingly, the first fluid flow (8) having a fluid flow temperature (79) greater than a body temperature (80) can flow into the first external ear canal (5) or the second external ear canal (14).

Figure 29A:
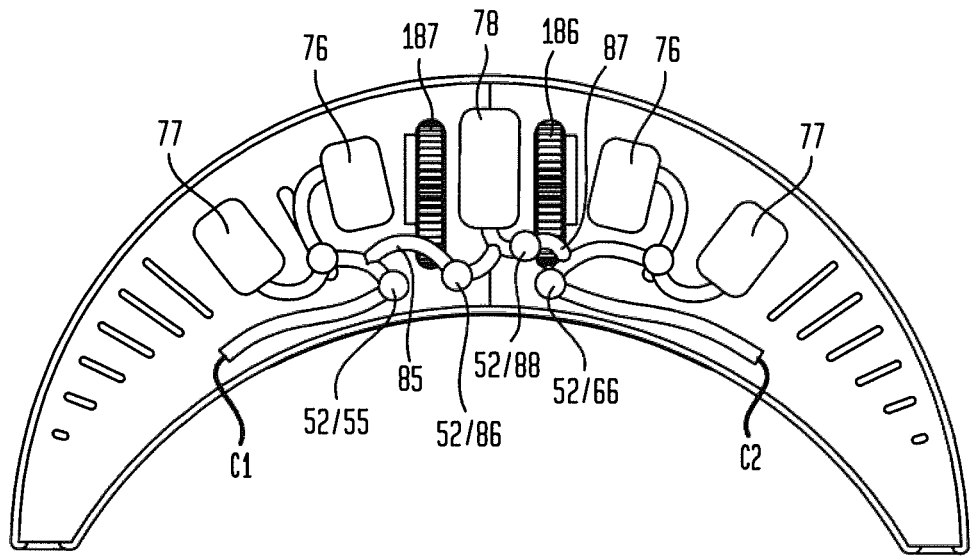
FIG. 29A is a first interior plan view of a particular embodiment of an external ear canal pressure regulation device.

Now referring primarily to FIG. 28 and FIG. 29A, the external ear canal pressure regulation device (1) can further include a fluid flow temperature regulator (78) fluidicly coupled to the first fluid flow (8) and the second fluid flow (20). The fluid flow temperature regulator (78) can be operable to regulate a fluid flow temperature (79) of the first fluid flow (8) or the second fluid flow (19), adjusting the fluid flow temperature (79) of the first fluid flow (8) or adjusting the fluid flow temperature (79) of the second fluid flow (20) to lesser or greater than a body temperature (80). Typically, the fluid flow temperature (79) can be in a range of between 10 degrees Celsius to about 50 degrees Celsius; however, embodiments can have a lesser or greater fluid flow temperature (79) depending upon the application.

Now referring primarily to FIG. 28 and FIG. 40, as to particular embodiments of the external ear canal pressure regulation device (1) having the configuration shown in FIG. 27 through FIG. 35, to generate a first pressure differential (9) in the first external ear canal (5) and regulate a fluid flow temperature (79) of the second fluid flow (20) in the second external ear canal (14), valves V1, V3L, V3R, V4, and 1R can be in the open condition and valves V2, V5, V6, and 1L can be in the closed condition. As to other particular embodiments, to generate a second pressure differential (17) in the second external ear canal (14) and regulate a first fluid flow temperature (79) of the first fluid flow (8) in the first external ear canal (5), valves V2, V3R, V3L, V5, and 1L can be in the open condition and valves V1, V4, V6, and 1R can be in the closed condition.

Now referring primarily to FIG. 28, the external ear canal pressure regulation device (1) can further include a third fluid flow generator (81) capable of generating a third fluid flow (82) having a third fluid flow rate (83) in a range of between 0 to about 10 liters per minute. As to particular embodiments, the third fluid flow generator (81) can be similar to the first and second fluid flow generators (2)(19) described above. As to particular embodiments, the fluid flow temperature regulator (78) can be fluidicly coupled to the third fluid flow generator (81), which can operate to regulate a third fluid flow temperature (84) of the third fluid flow (82). The third fluid flow generator (81) can be fluidicly coupled to the first and second axial earpiece conduits (4)(13), allowing the third fluid flow generator (81) to generate a third fluid flow (82) having a third fluid flow temperature (84) which can be delivered to the first and second external ear canals (5)(14) by the corresponding first and second axial earpiece conduits (4)(13).

Typically, the third fluid flow temperature (84) can be in a range of between 10 degrees Celsius to about 50 degrees Celsius; however, embodiments can have a lesser or greater third fluid flow temperature (84) depending upon the application. As to particular embodiments, the third fluid flow temperature (84) (or a third pre-selected fluid flow temperature) can be selected from one or more of the group including or consisting of: between about 10 degrees Celsius to about 20 degrees Celsius, between about 15 degrees Celsius to about 25 degrees Celsius, between about 20 degrees Celsius to about 30 degrees Celsius, between about 25 degrees Celsius to about 35 degrees Celsius, between about 30 degrees Celsius to about 40 degrees Celsius, between about 35 degrees Celsius to about 45 degrees Celsius, and between about 40 degrees Celsius to about 50 degrees Celsius.

One or a plurality of third fluid flow temperatures (84) (or third pre-selected fluid flow temperatures) can be generated with the external ear canal pressure regulation device (1) depending upon the method of use, which can be further influenced by factors such as user (33) anatomy, physiology, or biochemistry of the auditory meatus (34); disorder symptom targeted for alleviation; disorder targeted for treatment; observable effect(s) of using one or a plurality of third fluid flow temperatures (84) (or third pre-selected fluid flow temperatures) in a particular method of using the external ear canal pressure regulation device (1); or the like; or combinations thereof; whereby the one or the plurality of third fluid flow temperatures (84) (or third pre-selected fluid flow temperatures) can be effective to alleviate one or more disorder symptoms or treat one or more disorders, but not so much as to cause discomfort to the user (33) or injury to the auditory meatus (34) or the tympanic membrane (35).

Typically, the third fluid flow rate (83) can be in a range of between 0 liters per minute to about 10 liters per minute; however, embodiments can have a lesser or greater third fluid flow rate (83) depending upon the application. As to particular embodiments, the third fluid flow rate (83) (or a third pre-selected fluid flow rate) can be selected from one or more of the group including or consisting of: between about 0 liters per minute to about 2 liters per minute, between about 1 liter per minute to about 3 liters per minute, between about 2 liters per minute to about 4 liters per minute, between about 3 liters per minute to about 5 liters per minute, between about 4 liters per minute to about 6 liters per minute, between about 5 liters per minute to about 7 liters per minute, between about 6 liters per minute to about 8 liters per minute, between about 7 liters per minute to about 9 liters per minute, and between about 8 liters per minute to about 10 liters per minute.

One or a plurality of third fluid flow rates (83) (or third pre-selected fluid flow rates) can be generated with the external ear canal pressure regulation device (1) depending upon the method of use, which can be further influenced by factors such as user (33) anatomy, physiology, or biochemistry of the auditory meatus (34); disorder symptom targeted for alleviation; disorder targeted for treatment; observable effect(s) of using one or a plurality of third fluid flow rates (83) (or third pre-selected fluid flow rates) in a particular method of using the external ear canal pressure regulation device (1); or the like; or combinations thereof; whereby the one or the plurality of third fluid flow rates (83) can be in an amount effective to alleviate one or more disorder symptoms or treat one or more disorders, but not so much as to cause discomfort to the user (33) or injury to the auditory meatus (34) or the tympanic membrane (35).

Now referring primarily to FIG. 28 and FIG. 29A, particular embodiments of the external ear canal pressure regulation device (1) having a third fluid flow generator (81) can further include a first valved conduit (85) having a first valved conduit valve (86) which operably interrupts the third fluid flow (82) to the first axial earpiece conduit (4). In the open condition, the first valved conduit valve (86) allows the third fluid flow (82) to flow from the third fluid flow generator (81) toward the first axial earpiece conduit (4) and, accordingly, toward the first external ear canal (5). In the closed condition, the first valved conduit valve (86) precludes the third fluid flow (82) from flowing from the third fluid flow generator (81) toward the first axial earpiece conduit (4).

Again referring primarily to FIG. 28 and FIG. 29A, particular embodiments of the external ear canal pressure regulation device (1) having a third fluid flow generator (81) can further include a second valved conduit (87) having a second valved conduit valve (88) which operably interrupts the third fluid flow (82) to the second axial earpiece conduit (13). In the open condition, the second valved conduit valve (88) allows the third fluid flow (82) to flow from the third fluid flow generator (81) toward the second axial earpiece conduit (13) and, accordingly, toward the second external ear canal (14). In the closed condition, the second valved conduit valve (88) precludes the third fluid flow (82) from flowing from the third fluid flow generator (81) toward the second axial earpiece conduit (13).

Now referring primarily to FIG. 28 and FIG. 40, as to particular embodiments of the external ear canal pressure regulation device (1) having the configuration shown in FIG. 27 through FIG. 35, to generate a third fluid flow (82) having a third flow temperature (84) and a third fluid flow rate (83) in the first external ear canal (5) and the second external ear canal (14), valves V3L, V3R, 1L, 1R, and V6 can be in the open condition and valves V1, V2, V4, and V5 can be in the closed condition. As to other particular embodiments, to only generate a third fluid flow (82) having a third flow temperature (84) and a third fluid flow rate (82) in the first external ear canal (5), valves V3L, 1L, and V6 can be in the open condition and valves V1, V2, V3R, V4, V5, and 1R can be in the closed condition. As to other particular embodiments, to only generate a third fluid flow (82) having a third flow temperature (84) and a third fluid flow rate (83) in the second external ear canal (14), valves V3R, IR, and V6 can be in the open condition and valves V1, V2, V3L, V4, V5, and 1L can be in the closed condition.

Now referring primarily to FIG. 8, FIG. 9A, FIG. 28, and FIG. 29B, particular embodiments of the external ear canal pressure regulation device (1) can further include a manifold exhaust valve (89), which in the open condition, can allow the first fluid flow (8) or the second fluid flow (20) to egress from the fluid flow manifold (51) to the ambient pressure (11), thereby relieving the first or the second pressure differentials (9)(17).

Now referring primarily to FIG. 28 and FIG. 40, as to particular embodiments of the external ear canal pressure regulation device (1) having the configuration shown in FIG. 27 through FIG. 35, to exhaust the fluid flow manifold (51), valve V6 can be in the open condition and valves V1, V2, V3L, V3R, V4, V5, 1L, and 1R can be in the closed condition.

Now referring generally to FIG. 1 through FIG. 8 and FIG. 11 through FIG. 28, embodiments of the external ear canal pressure regulation device (1) can include a first or a second earpiece (3)(12) having compliant corresponding first or second earpiece external surface (7)(16) configured to correspondingly sealably engage a first or second external ear canal (5)(14), thus acting as a corresponding first or second barrier (102)(103) between the corresponding first or second external ear canal pressure (10)(18) and the ambient pressure (11). Embodiments of the first or second earpiece (3)(12) can be configured to sufficiently sealably engage with the first or second external ear canal (5)(14) to resist axial or lateral displacement in view of normal anatomical variations of the first or second external ear canal (5)(14) over a normal range of operating temperatures of between about 20° C. (about 68° F.) to about 50° C. (about 122° F.) and allow generation and maintenance of a normal range of operating pressures of between about −50 kilopascals below the ambient pressure (11) to about +50 kilopascals above the ambient pressure (11).

Now referring primarily to FIG. 11 through FIG. 18, as to particular embodiments, the first or second earpieces (3)(12) of the external ear canal pressure regulation device (1) can be formed from a compliant material which can correspondingly compressibly deform upon engagement with the corresponding first or second external ear canals (5)(14), thereby allowing the first or second earpieces (3)(12) to sealably conform to the corresponding first or second external ear canals (5)(14). As to these particular embodiments, the first or second earpieces (3)(12) can be formed, molded, three-dimensionally printed, or otherwise fabricated from any of a numerous and wide variety of materials capable of sealable engagement with the corresponding first or second external ear canals (5)(14), including or consisting of: a silicone, a foam (including polyurethane foam), a polyvinylsiloxane, a low durometer elastomer, or the like, or combinations thereof.

As to particular embodiments, the first or second earpieces (3)(12) can be generally uniform, formed from one material, for example a lesser durometer elastomer. As to other particular embodiments, the first or second earpieces (3)(12) can be formed from a plurality of layers, for example an inner core layer having a greater durometer surrounded by an outer layer having a lesser durometer or an inner core layer having a lesser durometer surrounded by an outer layer having a greater durometer.

As to particular embodiments, a portion of the first or second earpiece external surfaces (7)(16) can inwardly taper from an earpiece first end (92) approaching an earpiece second end (93). As an illustrative example of particular embodiments of this configuration, the first or second earpiece external surfaces (7)(16) can be configured in the general form of a truncated cone inwardly tapering approaching the earpiece second end (93). As to particular embodiments, the first or second earpiece external surfaces (7)(16) can further include a plurality of circumferential ribs disposed in spaced apart relation between the earpiece first end (92) and the earpiece second end (93).

The first or second earpiece external surfaces (7)(16) can remain sealably engaged with the corresponding first or second external ear canals (5)(14) by frictional forces between the first or second earpiece external surfaces (7)(16) and the corresponding first or second external ear canals (5)(14). As to particular embodiments, the first or second earpiece external surfaces (7)(16) can remain engaged with the corresponding first or second external ear canals (5)(14) by forcible urging against the external ear canal pressure regulation device (1) during normal operation. As to other particular embodiments, a retention element (182) can be coupled to the earpiece (3)(12) or the external ear canal pressure regulation device (1), which can be worn within the ear (6)(15), about the ear (6), about the head (95), or about the neck (183) to assist with retention of the earpiece (3)(14) within the external ear canal (5)(14).

Now referring primarily to FIG. 11 through FIG. 18, a retention element (182) can be provided as a resiliently flexible member (182) coupled about the earpiece (3)(14). As to particular embodiments, the resiliently flexible member (182) can be configured to be disposed within a concha area (183) of the ear (6)(15), which upon forcible urging into the concha area (183), can assist in retaining the earpiece (3)(14) within the external ear canal (5)(14). As to particular embodiments, the resiliently flexible member (182) can be configured as an arcuate annular member (184) having a plurality of radially disposed spokes (185).

Now referring primarily to FIG. 8, FIG. 9B, FIG. 10, FIG. 19 through FIG. 26, FIG. 28, and FIG. 29B, as to particular embodiments, the external ear canal pressure regulation device (1) can further include a fourth fluid flow generator (96) capable of generating a fourth fluid flow (99). The fourth fluid flow generator (96) can be configured substantially in the same manner as the first fluid flow generator (2) or the second fluid flow generator (19), as described above. A first coaxial earpiece conduit (97) can be disposed about the first axial earpiece conduit (4) and a second coaxial earpiece conduit (98) can be disposed about the second axial earpiece conduit (13) (as to those embodiments which include a second axial earpiece conduit (13)). The first and second coaxial earpiece conduits (4)(13) can be fluidicly coupled to the fourth fluid flow generator (96). A first elastomer sleeve (100) and a second elastomer sleeve (101) can be correspondingly disposed about the first and second axial earpiece conduits (4)(13) to provide the corresponding first and second earpiece external surfaces (7)(16) configured to correspondingly sealably engage the first and second external ear canals (5)(14) to provide the corresponding first and second barriers (102) (103) between the corresponding first and second external ear canal pressures (10)(18) and the ambient pressure (11). The first and second elastomer sleeves (100)(101) can be fluidicly coupled to the first and second coaxial earpiece conduits (97)(98). The fourth fluid flow (99) in the first and second coaxial earpiece conduits (97)(98) can generate corresponding first and second coaxial earpiece conduit pressure differentials (104)(105) between corresponding first and second coaxial earpiece conduit pressures (106)(107) and the ambient pressure (11). The first and second coaxial earpiece conduit pressure differentials (106)(107) can be capable of correspondingly expanding the first and second elastomer sleeves (100)(101) to correspondingly sealably engage the first and second external ear canals (5)(14).

Figure 29B:
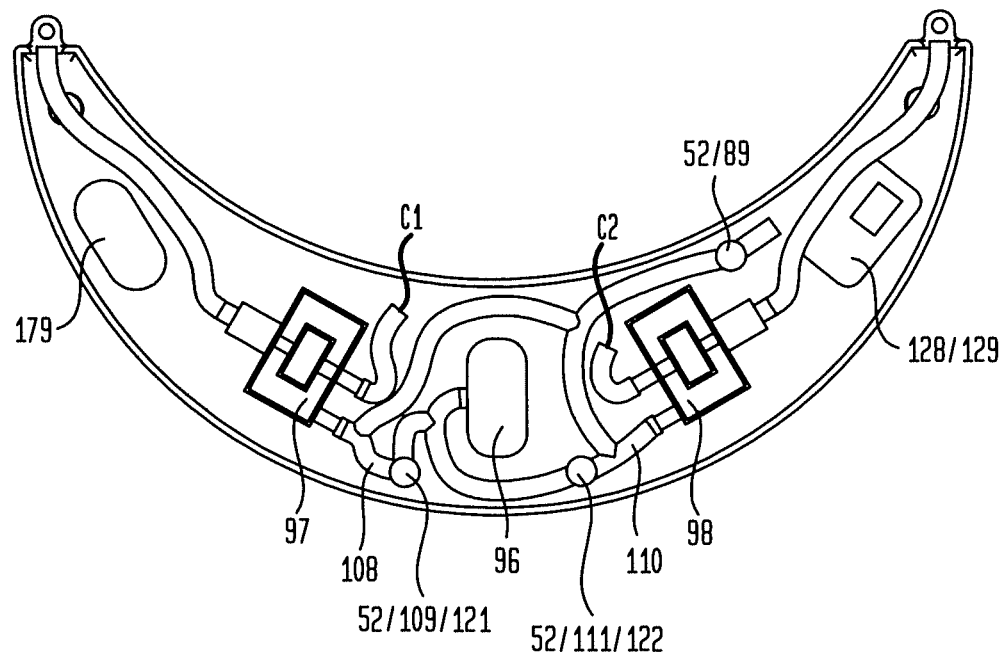
FIG. 29B is a second interior plan view of the particular embodiment of the external ear canal pressure regulation device shown in FIG. 29A.
Figure 30:
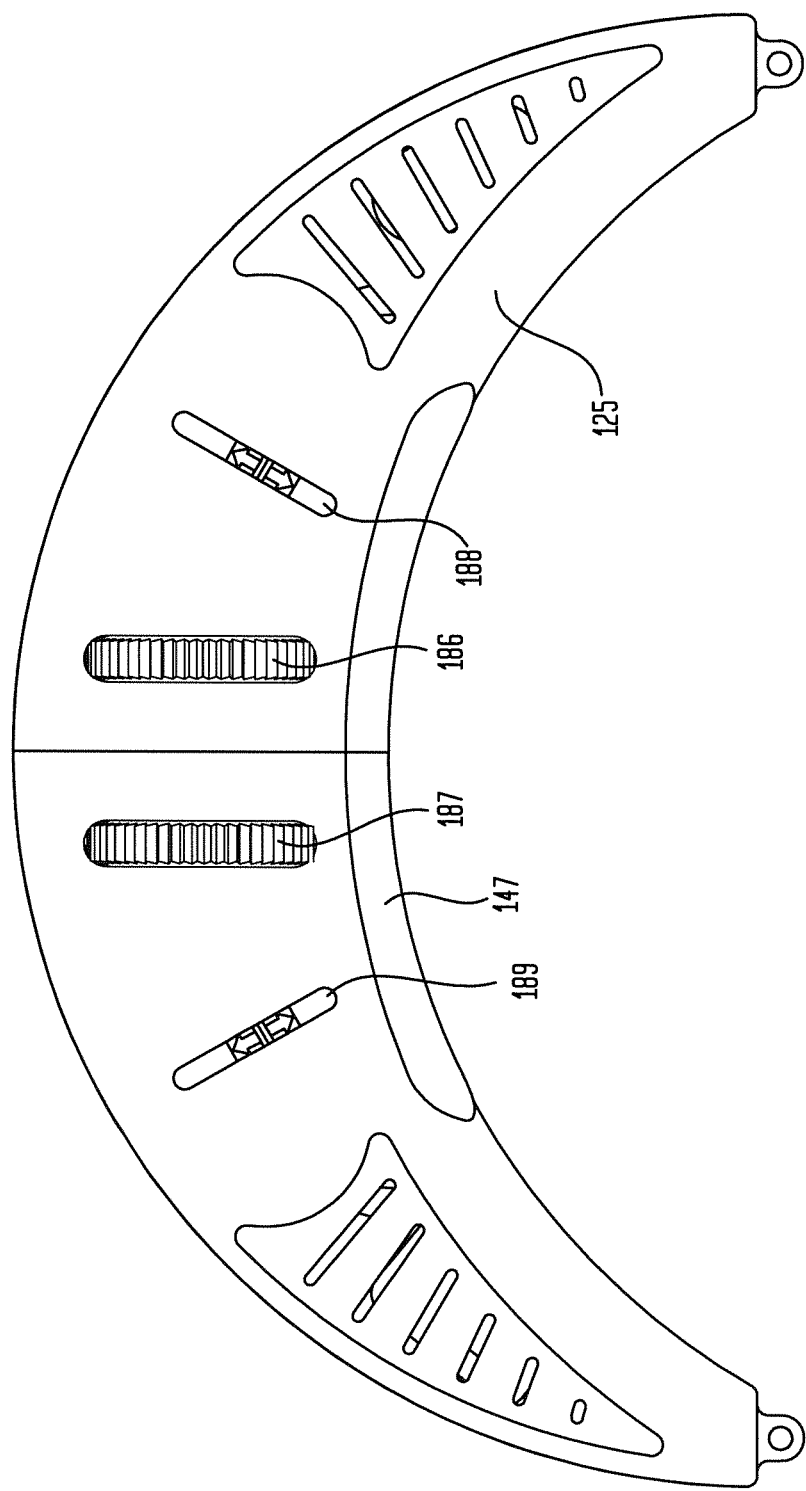
FIG. 30 is a top view of a particular embodiment of an external ear canal pressure regulation device.
Figure 31:
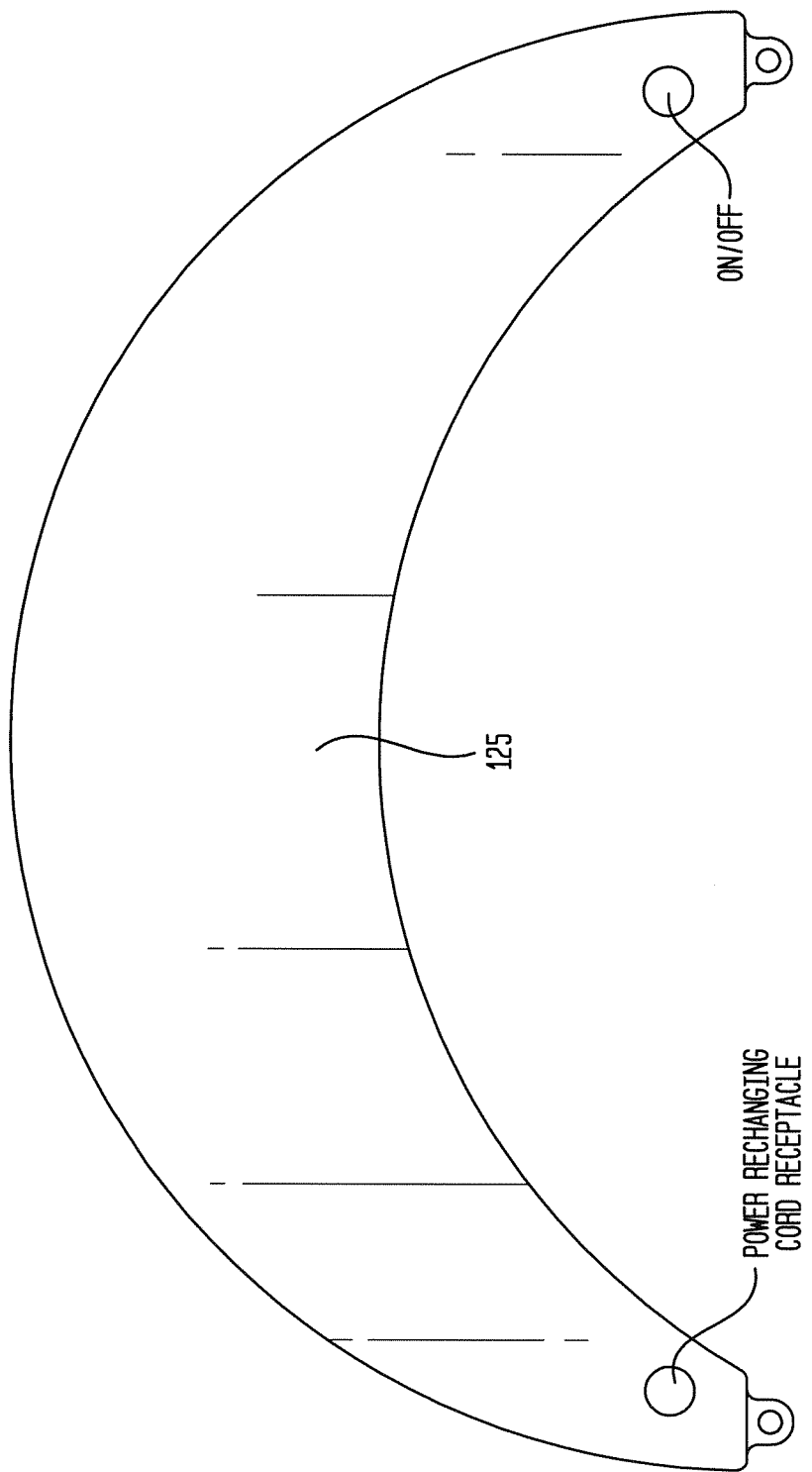
FIG. 31 is a bottom view of a particular embodiment of an external ear canal pressure regulation device.
Figure 34:
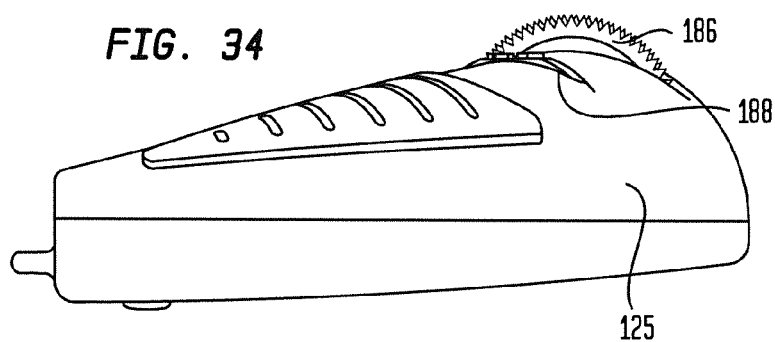
FIG. 34 is a first end view of a particular embodiment of an external ear canal pressure regulation device.
Figure 35:
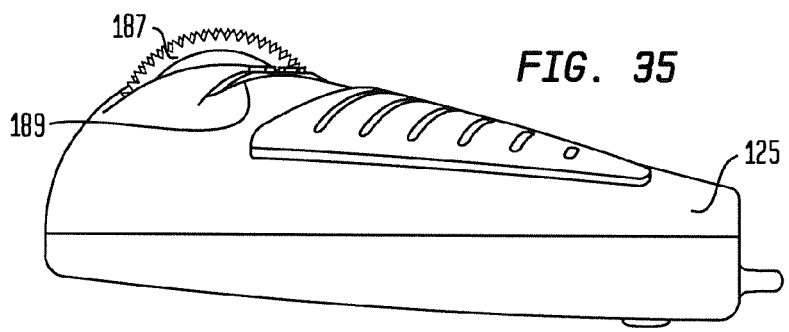
FIG. 35 is a second end view of a particular embodiment of an external ear canal pressure regulation device.

Now referring primarily to FIG. 28 and FIG. 29B, particular embodiments of the external ear canal pressure regulation device (1) having a fourth fluid flow generator (96) can further include a third valved conduit (108) having a third valved conduit valve (109) which operably interrupts the fourth fluid flow (99) to the first coaxial earpiece conduit (97). In the open condition, the third valved conduit valve (109) allows the fourth fluid flow (99) to flow from the fourth fluid flow generator (96) toward the first coaxial earpiece conduit (97) and, accordingly, toward the first elastomer sleeve (100). In the closed condition, the third valved conduit valve (109) precludes the fourth fluid flow (99) from flowing from the fourth fluid flow generator (96) toward the first elastomer sleeve (100).

Again referring primarily to FIG. 28 and FIG. 29B, particular embodiments of the external ear canal pressure regulation device (1) having a fourth fluid flow generator (96) can further include a fourth valved conduit (110) having a fourth valved conduit valve (111) which operably interrupts the fourth fluid flow (99) to the second coaxial earpiece conduit (98). In the open condition, the fourth valved conduit valve (111) allows the fourth fluid flow (99) to flow from the fourth fluid flow generator (96) toward the second coaxial earpiece conduit (98) and, accordingly, toward the second elastomer sleeve (101). In the closed condition, the fourth valved conduit valve (111) precludes the fourth fluid flow (99) from flowing from the fourth fluid flow generator (96) toward the second elastomer sleeve (101).

Now referring primarily to FIG. 28, the external ear canal pressure regulation device (1) can further include a fourth fluid flow generator controller (112) which can control operation of the fourth fluid flow generator (96) to generate the first and second coaxial earpiece conduit pressure differentials (104)(105) between the corresponding first and second coaxial earpiece conduit pressures (106)(107) and the ambient pressure (11) to expand the corresponding first and second elastomer sleeves (100)(101) to sealably engage the corresponding first and second external ear canals (5)(14), thereby providing the corresponding first and second barriers (102)(103) between the corresponding first and second external ear canal pressures (10)(18) and the ambient pressure (11).

Again referring primarily to FIG. 28, the external ear canal pressure regulation device (1) can further include a third pressure sensor (113) fluidicly coupled to the first coaxial earpiece conduit (97). The third pressure sensor (113) can generate a third pressure sensor signal (114) which varies based upon change in the first coaxial earpiece conduit pressure differential (104) between the first coaxial earpiece conduit pressure (106) and the ambient pressure (11).

Again referring primarily to FIG. 28, the external ear canal pressure regulation device (1) can further include a fourth pressure sensor (115) fluidicly coupled to the second coaxial earpiece conduit (98). The fourth pressure sensor (115) can generate a fourth pressure sensor signal (116) which varies based upon change in the second coaxial earpiece conduit pressure differential (105) between the second coaxial earpiece conduit pressure (107) and the ambient pressure (11).

Now referring primarily to FIG. 28, the external ear canal pressure regulation device (1) can further include a coaxial earpiece conduit pressure sensor signal analyzer (117) which functions to identify stable first and second coaxial earpiece conduit pressure differentials (104)(105) between the corresponding first and second coaxial earpiece conduit pressures (106)(107) and the ambient pressure (11). The coaxial earpiece conduit pressure sensor signal analyzer (117) can generate a seal signal (118) upon occurrence of the stable first and second coaxial earpiece conduit pressure differentials (104)(105).

Now referring primarily to FIG. 6, FIG. 8, FIG. 9A, and FIG. 28, particular embodiments of the external ear canal pressure regulation device (1) can further include an elastomer sleeve seal indicator (119) responsive to the seal signal (118). The elastomer sleeve seal indicator (119) can generate a sensorial perceivable indicia (120) upon receiving the seal signal (118). The sensorial perceivable indicia (120) can include one or more of a sound indicia, a light indicia, a tactile indicia, or the like, or combinations thereof.

Now referring primarily to FIG. 28 and FIG. 29B, the external ear canal pressure regulation device (1) can further include third and fourth pressure relief valves (121)(122) correspondingly fluidicly coupled to the first and second coaxial earpiece conduits (97)(98). In the open condition, the third and fourth pressure relief valves (121)(122) can correspondingly relieve the first and second coaxial earpiece conduit pressure differentials (104)(105) between the corresponding first and second coaxial earpiece conduit pressures (106)(107) and the ambient pressure (11).

Now referring primarily to FIG. 8, the external ear canal pressure regulation device (1) can further include a pressure release selection element (123). The fourth fluid flow generator controller (112) can be responsive to operation of the pressure release selection element (123) to curtail operation of the fourth fluid flow generator (96) and operate the third and fourth pressure relief valves (121)(122) to correspondingly return the first and second coaxial earpiece conduit pressure differentials (104)(105) between the corresponding first and second coaxial earpiece conduit pressures (106)(107) and the ambient pressure (11) toward the ambient pressure (11) to contract the corresponding first and second elastomer sleeves (100)(101).

Now referring primarily to FIG. 37A through FIG. 39E, which provide graphs of pressure regulation profiles (136) which can be administered by embodiments of the external ear canal pressure regulation device (1) effective to alleviate one or more disorder symptoms or treat one or more disorders. Each graph shows a pressure differential (9)(17) between the external ear canal pressure (10)(18) and the ambient pressure (11) achieved over a time period (39). As to particular embodiments, a fluid flow generator (2)(19) can be operated to generate a fluid flow (8)(20) which egresses from an axial earpiece conduit (4)(13) toward an external ear canal (5)(14) over a time period (39), resulting in a positive external ear canal pressure (10)(18) relative to the ambient pressure (11) (as shown in the examples of FIG. 37A through FIG. 37G). As to other particular embodiments, a fluid flow generator (2)(19) can be operated to generate a fluid flow (8)(20) which ingresses to an axial earpiece conduit (4)(13) from an external ear canal (5)(14) toward the fluid flow generator (2)(19) over a time period (39), resulting in a negative external ear canal pressure (10)(18) relative to the ambient pressure (11) (as shown in the examples of FIG. 38A through FIG. 38G).

Now referring primarily to FIG. 37A and FIG. 38A, the fluid flow generator (2)(19) can be operated to maintain a constant external ear canal pressure (10)(18) over a time period (39). As to particular embodiments, a constant external ear canal pressure (10)(18) can be maintained as a fluid volume (21) within the external ear canal (5)(14) over the time period (39) without (or substantially without) a fluid flow (8)(20). As an illustrative example, the external ear canal pressure regulation device (1) having an earpiece external surface (7)(16) sealably engaged within an external ear canal (5)(14), as described above, can be operated by control of the fluid flow generator (2)(19) to generate a fluid flow (2)(19) having a fluid volume (21) or a pre-selected fluid volume (22)

between the fluid flow generator (2)(19) and the external ear canal (5)(14) through the axial earpiece conduit (4)(13) of the earpiece (3)(12) to achieve a pressure differential (9)(17) between the external ear canal pressure (10)(18) and the ambient pressure (11). Once the desired fluid volume (21) or pre-selected fluid volume (22) establishes a pressure differential (9)(17), the pressure differential (9)(17) can be maintained for a time period (39) without or substantially without additional fluid flow (8)(20) due to sealable engagement of the earpiece external surface (7)(16) with the external ear canal (5)(14). As to other embodiments, once the desired pressure differential (9)(17) has been achieved, the pressure differential (9)(17) can be maintained for a time period (39) by additional fluid flow (8)(20) to or from the external ear canal (5)(14) to offset leakage about engagement of the earpiece external surface (7)(16) with the external ear canal (5)(14). As to other embodiments, the external ear canal pressure (10)(18) can be maintained for a time period (39) by continuous fluid flow (8)(20) to the external ear canal (5)(14).

Regardless of the method, the external ear canal pressure (10)(18) can be maintained constant over a time period (39) in a range of between about +50 kilopascals above the ambient pressure (11) to about −50 kilopascals below the ambient pressure (11) to alleviate one or more disorders symptom or treat one or more disorders. A positive external ear canal pressure (10)(18) relative to the ambient pressure (11) can be achieved by maintaining the external ear canal pressure (10)(18) in a range of between about 0 kilopascals to about +50 kilopascals above the ambient pressure (11). Alternatively, a negative external ear canal pressure (10)(18) relative to the ambient pressure (11) can be achieved by maintaining the external ear canal pressure (10)(18) in a range of between about −50 kilopascals to about 0 kilopascals below the ambient pressure (11).

Now referring primarily to FIG. 37B through FIG. 37G, FIG. 38B through FIG. 38G, and FIG. 39A through FIG. 39E, the fluid flow generator (2)(19) can be configured to generate a fluid flow (8)(20) having a pressure differential wave (124) defining for each instant in the time period (39) a pre-selected pressure differential amplitude (37)(67) and a pre-selected pressure differential amplitude oscillation frequency (49)(180). As to particular embodiments, the fluid flow generator (2)(19) can be operated to generate a fluid flow (8)(20) which egresses from the axial earpiece conduit (4)(13) toward the external ear canal (5)(14) over a time period (39) having a pressure differential wave (124) including a pre-selected pressure differential amplitude (37)(67) and a pre-selected pressure differential amplitude oscillation frequency (49)(180) which results in a positive external ear canal pressure (10)(18) relative to the ambient pressure (11) (as shown in the examples of FIG. 37B through FIG. 37G).

As to other particular embodiments, the fluid flow generator (2)(19) can be operated to generate a fluid flow (8)(20) which ingresses to the axial earpiece conduit (4)(13) from the external ear canal (5)(14) toward the fluid flow generator (2)(19) over a time period (29) having a pressure differential wave (124) including a pre-selected pressure differential amplitude (37)(67) and a pre-selected pressure differential amplitude oscillation frequency (49)(180) which results in a negative external ear canal pressure (10)(18) relative to the ambient pressure (11) (as shown in the examples of FIG. 38B through FIG. 38G).

As to other particular embodiments, a fluid flow generator (2)(19) can be operated to generate a fluid flow (8)(20) which can alternate between egress from the axial earpiece conduit (4)(13) toward the external ear canal (5)(14) and ingress to the axial earpiece conduit (4)(13) from the external ear canal (5)(14) toward the fluid flow generator (2)(19) over a time period (39) having a pressure differential wave (124) including a pre-selected pressure differential amplitude (37)(67) and a pre-selected pressure differential amplitude oscillation frequency (49)(180) which results in generating an external ear canal pressure (10)(18) which alternates between positive and a negative external ear canal pressure (10)(18) relative to the ambient pressure (11) (as shown in the examples of FIG. 39A through FIG. 39E).

As to other particular embodiments, the pressure differential wave (124) can oscillate with a pre-selected pressure differential amplitude oscillation frequency (49)(180) within a pre-selected pressure differential amplitude (37)(67) in a range of between 0 kilopascals to about +50 kilopascals above the ambient pressure (11) (as shown in the examples of FIG. 37B through FIG. 37G).

As to yet other particular embodiments, the pressure differential wave (124) can oscillate with a pre-selected pressure differential amplitude oscillation frequency (49)(180) in a range of between about −50 kilopascals to 0 kilopascals below the ambient pressure (11)(as shown in the examples of FIG. 38B through FIG. 38G).

Again referring primarily to FIG. 37B through FIG. 37G, FIG. 38B through FIG. 38G, and FIG. 39A through FIG. 39E, the pressure differential wave (124) can have a numerous and wide variety of waveforms, depending upon the application, corresponding to the numerous and wide variety of disorder symptoms which can be alleviated or disorders which can be treated by operation of the external ear canal pressure regulation device (1). As illustrative examples, the pressure differential wave (124) can be sine wave having smooth repetitive periodic oscillations (as shown in the example of FIG. 37B, FIG. 38B, and FIG. 39A), a square wave in which the pressure differential wave (124) alternates at a steady frequency between fixed minimum and maximum values, a rectangular wave, a trapezoidal wave or a truncated wave in which the apex of the pressure differential wave (124) has a constant pre-selected pressure differential amplitude (37)(67) over a time period (39) (as shown in the example of FIG. 37C, FIG. 37F, FIG. 38C, FIG. 38F, and FIG. 39B), a triangle wave having linear leading and trailing edges (as shown in the example of FIG. 37D, FIG. 38D, and FIG. 39C), a sawtooth wave in which the leading edge has a pre-selected pressure differential amplitude (37)(67) which changes over a greater time period (39) as compared to the trailing edge (as shown in the example of FIG. 37E and FIG. 39D), a reverse sawtooth wave in which the leading edge changes pre-selected pressure differential amplitude (37)(67) over a lesser time period (39) as compared to the trailing edge (as shown in the example of FIG. 37E and FIG. 39E), or combinations thereof (as shown in the example of FIG. 37G and FIG. 38G).

Now referring primarily to FIG. 6, FIG. 7, FIG. 9A, FIG. 9B, and FIG. 29A through FIG. 35, as to particular embodiments, the external ear canal pressure regulation device (1) can further include a housing (125) having a housing internal surface (126) defining a hollow internal space (127) in which components of the external ear canal pressure regulation device (1) can be housed.

While the fluid flow generators (2)(19) of the external ear canal pressure regulation device (1) above described typically deliver a fluid flow (8)(20) of air to the external ear canal (5)(14) to achieve the pressure differential (9)(17) between the external ear canal pressure (10)(18) and the ambient pressure (11), this is not intended to be limiting with respect to the wide variety of fluids which can be delivered to the external ear canal (5)(14) by embodiments of the external ear canal pressure regulation device (1). As illustrative examples, the wide variety of fluids can include: a purified gas, such as oxygen, nitrogen, argon, or the like; a mixture of partial pressures of gases; a liquid, such as water, oil, alcohol, or the like; or combinations thereof.

Additionally, while the fluid flow (8)(20)(82)(99) (or other fluid flows) or the transfer of a fluid volume (21)(22) between components of the external ear canal pressure regulation device (1), between components of the external ear canal pressure regulation device (1) and the external ear canal (5)(14), or between components of the external ear canal pressure regulation device (1) and the ambient pressure (11) can be above described as typically between a first point and a second point for the purpose of brevity, the fluid flow (8)(20)(82)(99) (or other fluid flows) or the transfer of a fluid volume (21)(22) includes all points within the manifold fluid flow path (54) between the first point and the second point.

Now referring primarily to FIG. 8 and FIG. 28, embodiment of the external ear canal pressure regulation device (1) can further include a controller (128). The controller (128), as to particular embodiments, can take the form of a single integrated circuit (129) containing a processor (130) in communication with a memory element (131). The memory element (131) can be in the form of a non-volatile computer storage medium that can be erased and reprogrammed and as to particular embodiments a random access memory for data storage. The memory element (131) can contain a computer code (132) executable to provide specified functions or combinations of steps for performing the specified functions to operate the various components of the external ear canal pressure regulation device (1) in accordance with embodiments of the invention above described.

The block diagrams and flowchart illustrations shown in FIG. 8 and FIG. 28 support combinations of elements for performing the specified functions, combinations of steps for performing the specified functions, and executable program elements for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions.

Now referring primarily to FIG. 8, the computer code (132) can include a first fluid flow generator controller (41) which can be executed to transform a pressure differential amplitude selection signal (133) received from the first fluid pressure differential amplitude selection element (40) to correspondingly control the first fluid flow generator (2) to produce the first fluid flow (8) which egresses from the first axial earpiece conduit (4). As to particular embodiments, the first fluid flow generator controller (41) increases or decreases the first fluid flow (8) based on variation in the pressure differential amplitude selection signal (133). As to other embodiments, the first fluid pressure differential amplitude selection element (40) can be used to select a pre-selected fluid volume (22) and the first fluid flow generator controller (41) can correspondingly control the first fluid flow generator (2) to deliver the pre-selected fluid volume (22), as above described.

As to particular embodiments of the external ear canal pressure regulation device (1), which include a first pressure sensor (56), the computer code (132) can further include a first pressure sensor signal analyzer (58) executable to provide a first pressure differential amplitude comparator (59) which functions to compare a first pre-selected pressure differential amplitude (37) selected by user interaction with the pressure differential amplitude selection element (40) to the first pressure differential amplitude (36) sensed in the first axial earpiece conduit (4). The first pressure sensor signal analyzer (58) can be further executed to provide a first pressure differential amplitude compensation signal (60) which varies based upon the difference between the first pre-selected pressure differential amplitude (37) and the sensed first pressure differential amplitude (36). The first fluid flow generator controller (41) can be responsive to the first pressure differential amplitude compensation signal (60) to control the first fluid flow generator (2) to achieve the first pre-selected pressure differential amplitude (37).

Again referring primarily to FIG. 8, the first fluid flow generator controller (41) can be further executed to transform a pressure differential amplitude oscillation frequency selection signal (134) received from the first pressure differential amplitude oscillation frequency selection element (50) to correspondingly control the first fluid flow generator (2) to produce a first pressure differential amplitude oscillation (45) which reciprocally drives the first fluid flow (8) between a first fluid flow first direction (46) and a first fluid flow second direction (47) in the first axial earpiece conduit (4).

As to particular embodiments, the first fluid flow generator controller (41) varies a first pressure differential amplitude oscillation frequency (48) based on variation in the pressure differential amplitude oscillation frequency selection signal (134). As to other embodiments, the first pressure differential amplitude oscillation frequency selection element (50) can be used select a first pre-selected pressure differential amplitude oscillation frequency (49) and the first fluid flow generator controller (41) can correspondingly control the first fluid flow generator (2) to deliver the first pre-selected pressure differential amplitude oscillation frequency (49) in the ranges as above described.

As to particular embodiments of the external ear canal pressure regulation device (1), which include the first pressure sensor (56), the first pressure sensor signal analyzer (58) can be further executable to provide a first pressure differential amplitude oscillation frequency comparator (61) which functions to compare a first pre-selected pressure differential amplitude frequency (49) selected by user interaction with the first pressure differential amplitude oscillation frequency selection element (50) to the first pressure differential amplitude oscillation frequency (48) sensed in the first axial earpiece conduit (4). The first pressure sensor signal analyzer (58) can be further executed to provide a first pressure differential amplitude oscillation frequency compensation signal (62) which varies based upon the difference between the first pre-selected pressure differential amplitude oscillation frequency (49) and the sensed first pressure differential amplitude oscillation frequency (48). The first fluid flow generator controller (41) can be responsive to the first pressure differential amplitude compensation signal (62) to control the first fluid flow generator (2) to achieve the first pre-selected pressure differential frequency (49).

With respect to particular embodiments of the first fluid flow generator (2) as shown by the illustrative examples of FIG. 8 and FIG. 9B, the first fluid flow generator controller (41) can indirectly control the function of first fluid flow generator (2) by controlling the movement of a linear actuator (30) coupled to a piston (26) movable within a barrel (27), as above described.

With respect to particular embodiments as shown the illustrative examples of FIG. 28, FIG. 29A, and FIG. 29B, the external ear canal pressure regulation device (1) can include a first fluid flow generator (2) which operates to deliver a first fluid flow (8) to the first axial earpiece conduit (4) and a second fluid flow generator (19) which operates to deliver a discrete second fluid flow (20) to the second axial earpiece conduit (13) sensed by a second pressure sensor (68), as above described. Correspondingly, the computer code (132) can further include a second fluid flow generator controller (73) and a second pressure sensor signal analyzer (70) including a second pressure differential amplitude comparator (71) and a second pressure differential amplitude oscillation frequency comparator (135), each of which can function to control operation of the second fluid flow generator (19), as above described for the first fluid flow generator (2), which allows independent control of a second pressure differential amplitude (63) and second pressure differential amplitude oscillation frequency (64) in the second axial earpiece conduit (13).

Again referring primarily to FIG. 28, FIG. 29A, and FIG. 29B, the first fluid flow generator (2) and the second fluid flow generator (19) can each include a positive fluid flow generator (76) and a negative fluid flow generator (77) each discretely controllable to achieve the a first and second pressure differential amplitudes (36)(63) and first and second pressure differential amplitude oscillation frequencies (48)(64). Accordingly, the first and second fluid flow generator controllers (41)(73) can be executed to discretely control each positive fluid flow generator (76) and each negative fluid flow generator (77) of the first and second fluid flow generators (2)(19) to achieve the first and second pressure differential amplitudes (36)(63) and first and second pressure differential amplitude oscillation frequencies (48)(64).

Now referring primarily to FIG. 28, FIG. 37A through FIG. 37G, FIG. 38A through FIG. 38G, and FIG. 39A through FIG. 39E, particular embodiments of the computer code (132) further include a timer module (137) responsive to a time period selection element (190) and a pressure regulation profile administration module (138) responsive to a pressure regulation profile selection element (139) which allows selection of one of a plurality of pressure regulation profiles (136) contained in the memory element (131), as above described and as shown in the Figures, or as otherwise programmed and contained in the memory element (131). The pressure regulation profile administration module (138) functions to coordinate operation of the first and second fluid flow generators (2)(19) to achieve the first or second pre-selected pressure differential amplitudes (37)(67) corresponding to each time point within a time period (39) of the selected one of the plurality of pressure regulation profiles (136).

Now referring primarily to FIG. 8 and FIG. 28, as to particular embodiments, the computer code (132) can further include a fluid flow temperature regulator controller (140) which functions to control the fluid temperature regulator (78) to adjust fluid flow temperature (79) of the first or second fluid flows (8)(20). As to the illustrative embodiment shown in FIG. 8, the fluid flow temperature regulator controller (140) actuates the fluid flow temperature regulator (78) to increase fluid flow temperature (78) of the first fluid flow (8) for a time period (39) upon actuation of the first fluid flow generator (2).

As to the illustrative embodiment shown in FIG. 28, the fluid flow temperature regulator controller (140) can be executed to transform a fluid flow temperature selection signal (141) received from a fluid flow temperature selection element (142) to correspondingly control the fluid flow temperature regulator (78) to adjust the fluid flow temperature (79) of a third fluid flow (82) within a range of about a range of 10° C. and 50° C., as above described. As to these embodiments, the computer code (132) can further include a third fluid flow controller (143) which functions to control the third fluid flow (82) from a third fluid flow generator (81) to a third fluid flow rate (83) of between 0 and about 10 liters per minute, as above described.

Now referring primarily to FIG. 8 and FIG. 28, the computer code (132) can further include a fourth fluid flow generator controller (112) executable to control the fourth fluid flow generator (96), as above described, to expand a first elastomer sleeve (100) or a second elastomer sleeve (101) correspondingly fluidicly coupled to the first or second coaxial earpiece conduit (97)(98) to correspondingly sealably engage the first or second external ear canal (5)(14) to provide the corresponding first or second barrier (102)(103) between the corresponding first or second external ear canal pressure (10)(18) and the ambient pressure (11). As to these embodiments, the computer code (132) can further include a coaxial earpiece conduit pressure sensor signal analyzer (117) executable to identify stable first and second coaxial earpiece conduit pressure differentials (104)(105) between the corresponding first and second coaxial earpiece conduit pressures (106)(107) and the ambient pressure (11). The third pressure sensor signal analyzer (117) can generate a seal signal (118) upon occurrence of the stable first and second coaxial earpiece conduit pressure differentials (104)(105) to generate the sensorial perceivable indicia (120), as above described. As to these embodiments, the computer code (132) can further include a seal release module (144) executable in response to operation of a seal release selection element (145) to operate the pressure relief valve (121)(122), as above described.

Now referring primarily to FIG. 40, the computer code (132) further includes a valve control module (146) executable to actuate one or more of the valves (52) depending on a selected method of administering fluid flow (8)(20)(82)(99) within embodiments of the external ear canal pressure regulation device (1), as above described.

Now referring primarily to FIGS. 28 and 32, particular embodiments further include a graphical display surface (147) and the computer program (132) can further include a graphical user interface module (148) which can be executed to depict a graphical user interface (149) on the graphical display surface (147). The graphical user interface (149) by user interaction can execute functions of the computer code (132) to operate the external ear canal pressure regulation device (1). While user interaction will typically be in the form of a touch by the user (33) on a control image (150) depicted the graphical display surface (147), this illustrative example is not intended to preclude any command by a user (33) by which a function of the computer code (132) can be activated, executed or performed whether through selection of one or a plurality of control image(s) (150), or by user voice command, keyboard stroke, mouse button, or otherwise.

Figure 2:
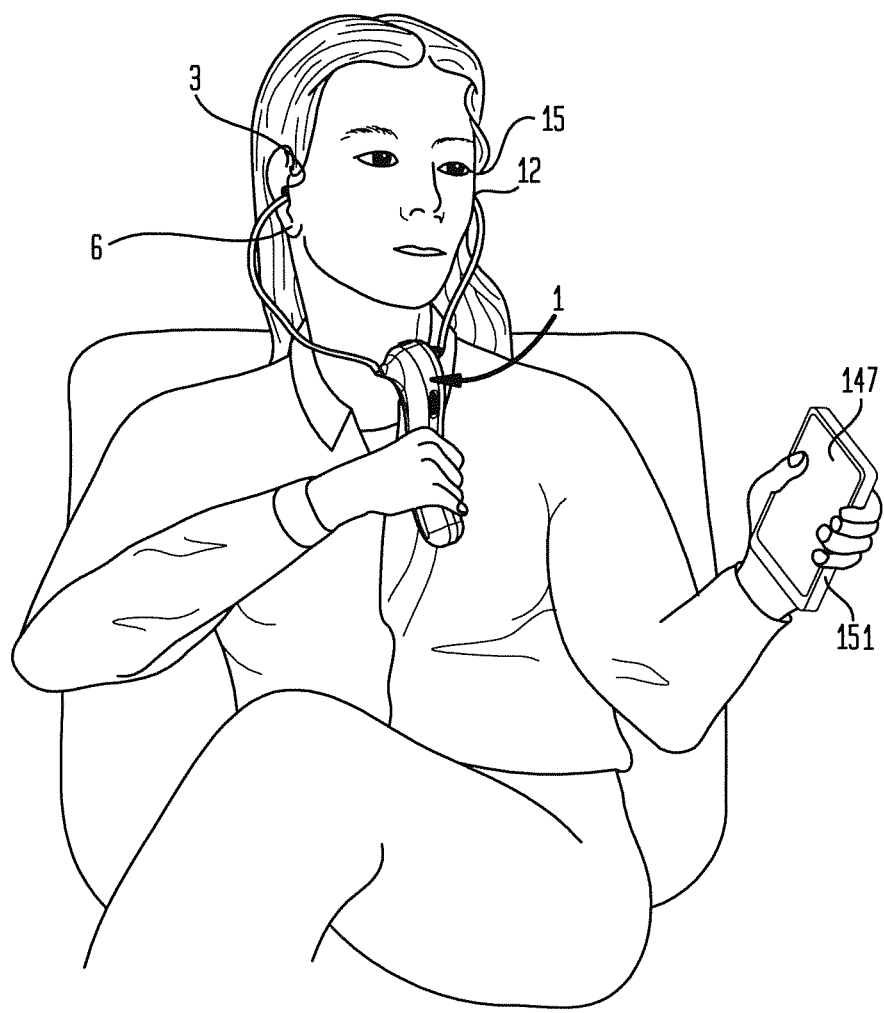
FIG. 2 is an illustration of a method of using a particular embodiment of the external ear canal pressure regulation device.
Figure 3:
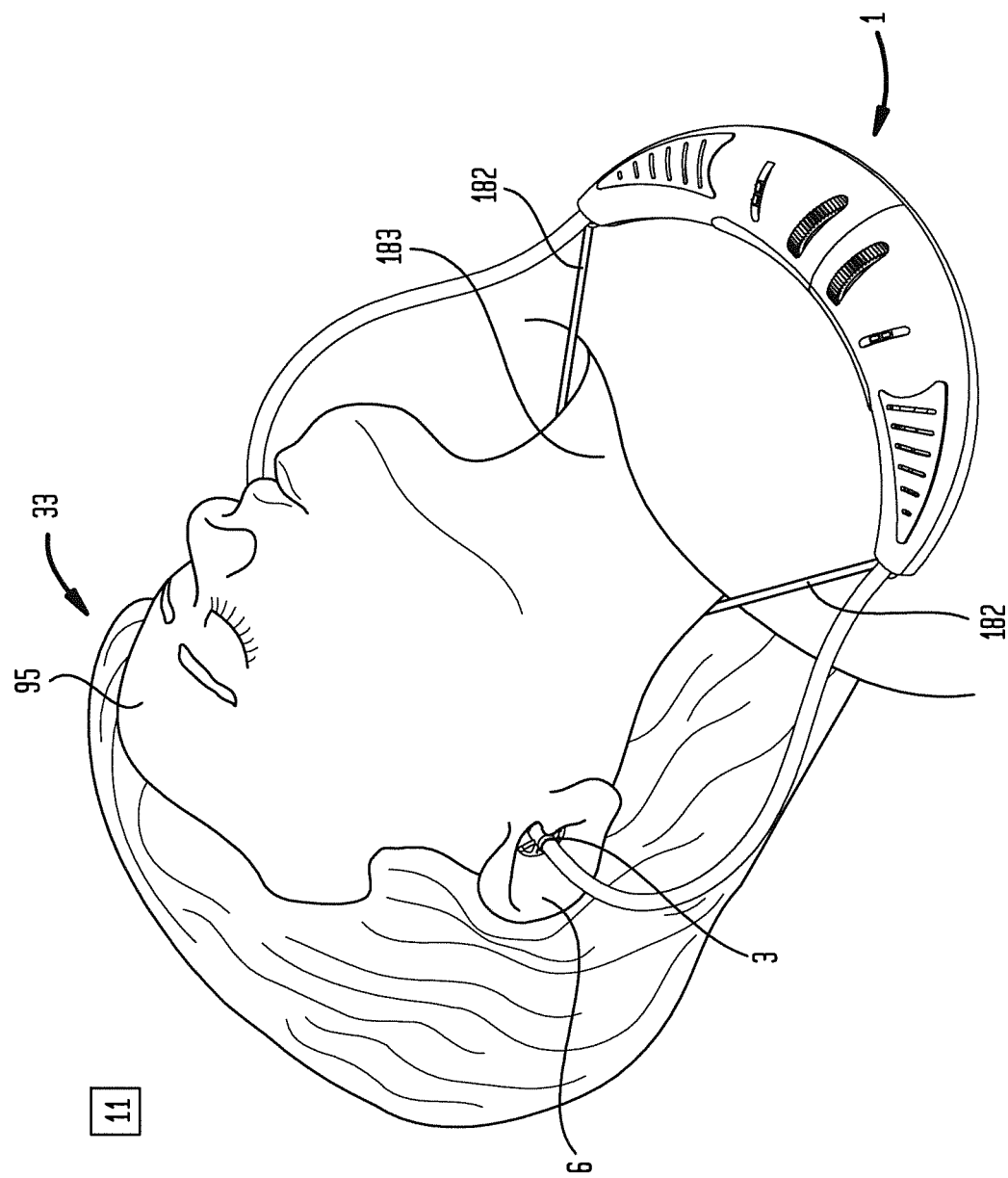
FIG. 3 is an illustration of a method of using a particular embodiment of the external ear canal pressure regulation device.

Now referring primarily to FIG. 1 and FIG. 2, particular embodiments can further include a computer device (151) discrete from the external ear canal pressure regulation device (1). The term "computer device (151)" means for the purpose of this invention any device adapted to receive the computer code (132) or receive a machine readable medium (152) containing the computer code (132), or includes a computer processor (153) in communication with a computer memory element (154) adapted to communicate with the external ear canal pressure regulation device (1), or downloads the computer code (132) through a wide area network (155), such as the Internet (156), or one or more local area networks (157) into a computer memory element (154) in communication with the computer processor (153). The computer device (151) can, as to particular embodiments, take the form of a limited-capability computer designed specifically for receiving the machine readable medium (152) in the form of a computer memory element (154) containing the computer code (132); however, other embodiments can take the form of set-top boxes, intelligent televisions connected to receive data through an entertainment medium such as a cable television network or a digital satellite broadcast, hand-held devices such as smart phones, slate or pad computers, personal digital assistants or camera/cell telephones, or multiprocessor systems, microprocessor-based or programmable consumer electronics, network personal computers, minicomputers, mainframe computers, or the like.

Again referring primarily to FIGS. 1 and 2, the computer device (151) can encompass one computer device or a plurality of computer devices, each of which can be operated by a user (33) to control one or a plurality of external ear canal pressure regulation devices (1). The user (33) can be a person, a plurality of persons, a business entity, or otherwise, can access to the computer device (151) to retrieve in a common format for display the graphic user interface (149) on computer graphical display surface (147).

As to particular embodiments, the controller (128) of the external ear canal pressure regulation device (1) can further include a communication controller (158) which can include a transceiver (159) associated with an antenna (160) to send and receive communication signals (161) to and from the computer device (151). As to particular embodiments the communication controller (158) can be a BLUETOOTH controller (for example a Texas Instruments CC2540 BLUETOOTH System-on-Chip) including the associated BLUETOOTH transceiver and BLUETOOTH antenna. As to particular embodiments, the communication controller (158) can be a Wi-Fi controller and the associated Wi-Fi receiver and Wi-Fi antenna.

Figure 36A:
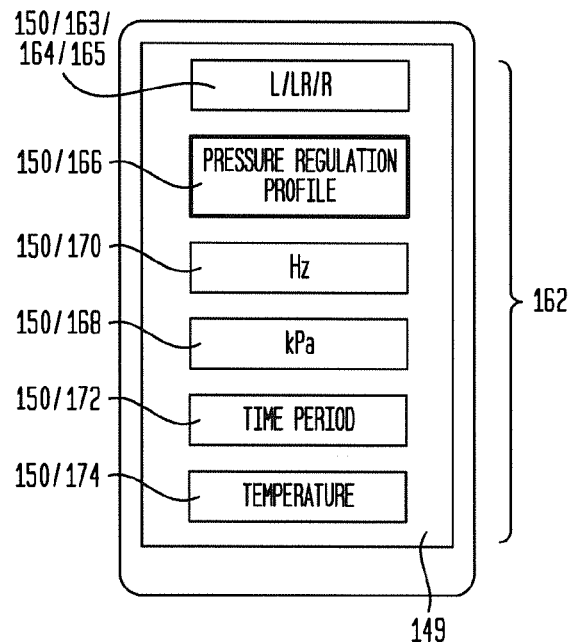
FIG. 36A is an illustration of a particular embodiment of a graphical user interface depicted on the display surface of a computer device and a method of using the graphical user interface to control operation of embodiments of the external ear canal pressure regulation device.
Figure 36B:
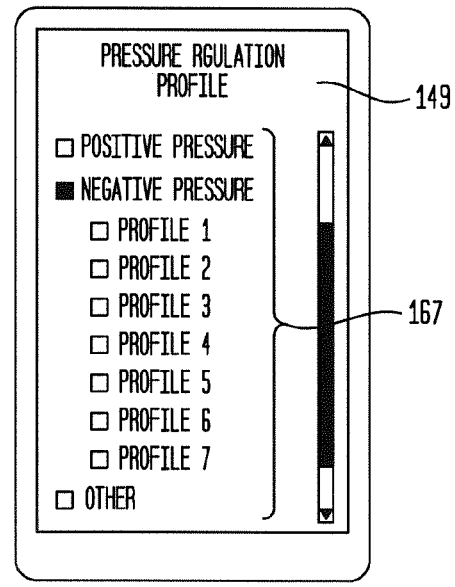
FIG. 36B is an illustration of a particular embodiment of the graphical user interface depicted on the display surface of a computer device and a method of using the graphical user interface to control operation of embodiments of the external ear canal pressure regulation device.

Now referring primarily to FIGS. 36A and 36B, an illustrative example of a graphical user interface (149) can include a mode selection list (162) which by user interaction allows selection of one or a plurality of: a first ear control image (163), a second ear control image (164), or both a first and second ear control image (165) which by user interaction selects administration of a first fluid flow (8) or a second fluid flow (20) or both a first and second fluid flow (8)(20) to the corresponding first and second axial earpiece conduits (4)(13); a pressure regulation profile control image (166) which by user interaction causes depiction of a list of selectable pressure regulation profile icons (167)(as shown in the example of FIG. 36B) which by user interaction allows selection of one of a plurality of pressure regulation profiles (136) to be administered, an external ear canal pressure differential amplitude control image (168) which by user interaction causes depiction of a list of selectable pressure differential amplitude control images which by user interaction allows selection of a pre-selected pressure differential amplitude (37), an external ear canal pressure differential frequency control image (170) which by user interaction causes depiction of a list of selectable pressure differential amplitude oscillation frequency control images which by user interaction allows selection of an pre-selected pressure differential amplitude oscillation frequency (49), a time period control image (172) which by user interaction causes depiction of a list of selectable time period control images which by user interaction allows selection of a time period (39) for administration or treatment, or a temperature regulation control icon (174) which by user interaction causes depiction of a list of selectable fluid flow temperatures and temperature-regulated flow rates which by user interaction selects administration of a fluid flow temperature (79) at a fluid flow rate (83).

Now referring primarily to FIGS. 8 and 28, embodiments of the external ear canal pressure regulation device (1) can further include a power source (177) which can be one or a combination of a transformed power (178) such as 110 volt alternating current transformed to 12 volt direct current or a power cell (179) such as a 12 volt direct current battery.

A method of producing particular embodiments of the external ear canal pressure regulation device (1) can include providing a first fluid flow generator (2) capable of generating a first fluid flow (8); and providing a first earpiece (3) having a first axial earpiece conduit (4) which communicates between a first earpiece first end (92) and a first earpiece second end (93). The first axial earpiece conduit (4) can be capable of fluidicly coupling to the first fluid flow generator (2). The first earpiece (3) can have a first compliant earpiece external surface (7) configured to sealably engage a first external ear canal (5) of a first ear (6) as a first barrier (102) between a first external ear canal pressure (10) and an ambient pressure (11).

The method of producing particular embodiments of the external ear canal pressure regulation device (1) can further include providing additional components of the external ear canal pressure regulation device (1) as above described.

As can be easily understood from the foregoing, the basic concepts of the present invention may be embodied in a variety of ways. The invention involves numerous and varied embodiments of an external ear canal pressure regulation device and methods for making and using such external ear canal pressure regulation devices including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "fluid flow" should be understood to encompass disclosure of the act of "flowing fluid"—whether explicitly discussed or not—and, conversely, were there effectively disclosure of the act of "flowing fluid", such a disclosure should be understood to encompass disclosure of a "fluid flow" and even a "means for flowing fluid." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the external ear canal pressure regulation devices herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. An external ear canal pressure regulation device, comprising:
    a first fluid flow generator capable of generating a first fluid flow;
    a first earpiece having a first axial earpiece conduit which communicates between a first earpiece first and second ends earpiece second ends, said first axial earpiece conduit fluidicly coupled to said first fluid flow generator, said first earpiece having a first compliant earpiece external surface configured to sealably engage a first external ear canal of a first ear as a first barrier between a first external ear canal pressure and an ambient pressure;
    said first fluid flow generator capable of generating a first pressure differential between said first external ear canal pressure and said ambient pressure, said first pressure differential having a first pressure differential amplitude and a first pressure differential amplitude oscillation frequency;
    a first pressure sensor which generates a first pressure sensor signal which varies based upon change in said first pressure differential; and
    a first pressure sensor signal analyzer comprising:
        a first pressure differential amplitude comparator which compares a first pre-selected pressure differential amplitude to said first pressure differential amplitude, said first pressure sensor signal analyzer generating a first pressure differential amplitude compensation signal to which a first fluid flow generator controller is responsive to control said first fluid flow generator to achieve said first pre-selected pressure differential amplitude; and
        a first pressure differential amplitude oscillation frequency comparator which compares a first pre-selected pressure differential amplitude oscillation frequency to said first pressure differential amplitude oscillation frequency, said first pressure sensor signal analyzer generating a first pressure differential amplitude oscillation frequency compensation signal to which said first fluid flow generator controller is responsive to control said first fluid flow generator to achieve said first pre-selected pressure differential amplitude oscillation frequency.

2. The device of claim 1, wherein said first pressure differential amplitude is in a range of between 0 kilopascals to about 50 kilopascals.

3. The device of claim 2, wherein said first pre-selected pressure differential amplitude is in said range of between 0 kilopascals to about 50 kilopascals.

4. The device of claim 3, further comprising:
a first pressure differential amplitude selection element; and
a first fluid flow generator controller responsive to operation of said first pressure differential amplitude selection element to regulate operation of said first fluid flow generator to achieve said first pre-selected pressure differential amplitude.

5. The device of claim 1, wherein said first pressure differential amplitude oscillation frequency is in a range of between 0 Hertz to about 10 Hertz.

6. The device of claim 5, wherein said first pre-selected pressure differential amplitude oscillation frequency is in said range of between 0 Hertz to about 10 Hertz.

7. The device of claim 6, further comprising a first pressure differential amplitude oscillation frequency selection element, said first fluid flow generator controller responsive to operation of said first pressure differential amplitude oscillation frequency selection element to regulate operation of said first fluid flow generator to achieve said first pre-selected pressure differential amplitude oscillation frequency.

8. The device of claim 6, further comprising a first pressure relief valve fluidicly coupled to said first axial earpiece conduit which relieves said first pressure differential in excess of a first pre-determined pressure differential having a first pre-determined pressure differential amplitude of between 0 kilopascals to about 50 kilopascals.

9. The device of claim 1, further comprising a first fluid flow temperature regulator fluidicly coupled to said first fluid flow, said first fluid flow temperature regulator operable to regulate a first fluid flow temperature of said first fluid flow.

10. The device of claim 1, further comprising a second earpiece having a second axial earpiece conduit which communicates between a second earpiece first end and a second earpiece second end, said second axial earpiece conduit fluidicly coupled to said first fluid flow generator, said second earpiece having a second compliant earpiece external surface configured to sealably engage a second external ear canal of a second ear as a second barrier between a second external ear canal pressure and said ambient pressure.

11. The device of claim 10, said first fluid flow generator capable of generating a second pressure differential between said second external ear canal pressure and said ambient pressure, said second pressure differential having a second pressure differential amplitude, said second pressure differential similar to said first pressure differential, said second pressure differential amplitude similar to said first pressure differential amplitude.

12. The device of claim 10, said first fluid flow generator capable of generating a second pressure differential amplitude oscillation having a second pressure differential amplitude oscillation frequency, said second pressure differential amplitude oscillation similar to said first pressure differential amplitude oscillation, said second pressure differential amplitude oscillation frequency similar to said first pressure differential amplitude oscillation frequency.

13. The device of claim 1, further comprising:
a second fluid flow generator capable of generating a second fluid flow; and
a second earpiece having a second axial earpiece conduit which communicates between second earpiece first and second ends, said second axial earpiece conduit fluidicly coupled to said second fluid flow generator, said second earpiece having a second compliant earpiece external surface configured to sealably engage a second external ear canal of a second ear as a second barrier between a second external ear canal pressure and said ambient pressure;
said second fluid flow generator capable of generating a second pressure differential between said second external ear canal pressure and said ambient pressure, said second pressure differential having a second pressure differential amplitude and a second pressure differential amplitude oscillation frequency;
a second pressure sensor which generates a second pressure sensor signal which varies based upon change in said second pressure differential; and
a second pressure sensor signal analyzer comprising:
a second pressure differential amplitude comparator which compares a second pre-selected pressure differential amplitude to said second pressure differential amplitude, said second pressure sensor signal analyzer generating a second pressure differential amplitude compensation signal to which a second fluid flow generator controller is responsive to control said second fluid flow generator to achieve said second pre-selected pressure differential amplitude; and
a second pressure differential amplitude oscillation frequency comparator which compares a second pre-selected pressure differential amplitude oscillation frequency to said second pressure differential amplitude oscillation frequency, said second pressure sensor signal analyzer generating a second pressure differential amplitude oscillation frequency compensation signal to which said second fluid flow generator controller is responsive to control said second fluid flow generator to achieve said second pre-selected pressure differential amplitude oscillation frequency.

14. The device of claim 13, wherein said second pressure differential amplitude is in a range of between 0 kilopascals to about 50 kilopascals.

15. The device of claim 14, wherein said second pre-selected pressure differential amplitude is in said range of between 0 kilopascals to about 50 kilopascals.

16. The device of claim 15, further comprising:
a second pressure differential amplitude selection element; and
a second fluid flow generator controller responsive to operation of said second pressure differential amplitude selection element to regulate operation of said second fluid flow generator to achieve said second pre-selected pressure differential amplitude.

17. The device of claim 15, wherein said second pressure differential amplitude oscillation frequency is in a range of between 0 Hertz to about 10 Hertz.

18. The device of claim 17, wherein said second pre-selected pressure differential amplitude oscillation frequency is in said range of between 0 Hertz to about 10 Hertz.

19. The device of claim 18, further comprising a second pressure differential amplitude oscillation frequency selection element, said second fluid flow generator controller responsive to operation of said second pressure differential amplitude oscillation frequency selection element to regulate operation of said second fluid flow generator to achieve said second pre-selected pressure differential amplitude oscillation frequency.

20. The device of claim 18, further comprising a second pressure relief valve fluidicly coupled to said second axial earpiece conduit which relieves said second pressure differential in excess of a second pre-determined pressure differential having a second pre-determined pressure differential amplitude of between 0 kilopascals to about 50 kilopascals.

21. The device of claim 13, further comprising a second fluid flow temperature regulator fluidicly coupled to said second fluid flow, said second fluid flow temperature regulator operable to regulate a second fluid flow temperature of said second fluid flow.

22. The device of claim 13, wherein each of said first and second fluid flow generators comprises a corresponding first and second pair of fluid flow generators correspondingly fluidicly coupled to said first and second axial earpiece conduits, each of said first and second pair of fluid flow generators including one positive pressure fluid flow generator which correspondingly generates a first or second fluid flow which egresses from said corresponding first or second axial earpiece conduit and one negative pressure fluid flow generator which correspondingly generates a first or second fluid flow which ingresses to said corresponding first or second axial earpiece conduit.

* * * * *